United States Patent [19]
Manahan et al.

[11] Patent Number: 4,567,774
[45] Date of Patent: Feb. 4, 1986

[54] DETERMINING MECHANICAL BEHAVIOR OF SOLID MATERIALS USING MINIATURE SPECIMENS

[75] Inventors: Michael P. Manahan, Columbus, Ohio; Ali S. Argon, Belmont; Otto K. Harling, Hingham, both of Mass.

[73] Assignee: Battelle Development Corporation, Columbus, Ohio

[21] Appl. No.: 489,597

[22] Filed: Apr. 28, 1983

[51] Int. Cl.⁴ .............................................. G01N 3/08
[52] U.S. Cl. ........................................ 73/826; 73/808; 73/818; 73/825; 73/849; 374/49
[58] Field of Search ................ 73/849, 799, 838, 839, 73/826, 834, 808, 818, 825; 364/508; 374/49

[56] References Cited
PUBLICATIONS

Laugier, M., Measurement of the Intrinsic . . . Technique from Thin Solid Films, vol. 75, No. 3, Jan. 1981, pp. 213-219.

Fan Hsiung Huang, Margaret L. Hamilton, and Gary L. Wire, "Bend Testing for Miniature Disks", Nuclear Technology 57, May 1982, 234-242.

Manahan, M. P., and Argon, A. S., "Design of Mechanical Property Tests and Establishment of Associated Testing Systems", in Annual Report on Alloy Development for Irradiation Performance in Fusion Reactors, Sep. 1979-Sep. 1980, Report No. MITNRL-006 and DOE/ER-10107-1, Dec. 1980, pp. 22-30.

M. P. Manahan, A. S. Argon and O. K. Harling, "The Development of a Miniaturized Disk Bend Test for the Determination of Postirradiation Mechanical Properties", Journal of Nuclear Materials 103 & 104 (1981) 1545-1550.

M. P. Manahan, A. S. Argon, and O. K. Harling, "Mechanical Behavior Evaluation Using the Miniaturized Disk Bend Test", Published in the 16th Quarterly Technical Progress Report on Damage and Fundamental Studies, Oct.-Dec. 1981 DOE/ER-0046/8.

*Primary Examiner*—Jerry W. Myracle
*Attorney, Agent, or Firm*—Philip M. Dunson; Robert B. Watkins

[57] ABSTRACT

A Miniaturized Bend Test (MBT) capable of extracting and determining mechanical behavior information from specimens only so large as to have at least a volume or smallest dimension sufficient to satisfy continuum behavior in all directions. The mechanical behavior of the material is determined from the measurements taken during the bending of the specimen and is processed according to the principles of linear or nonlinear material mechanics or both. In a preferred embodiment the determination is carried out by a code which is constructed according to the finite element method, and the specimen used for the determinations is a miniature disk simply supported for central loading at the axis on the center of the disk.

64 Claims, 51 Drawing Figures

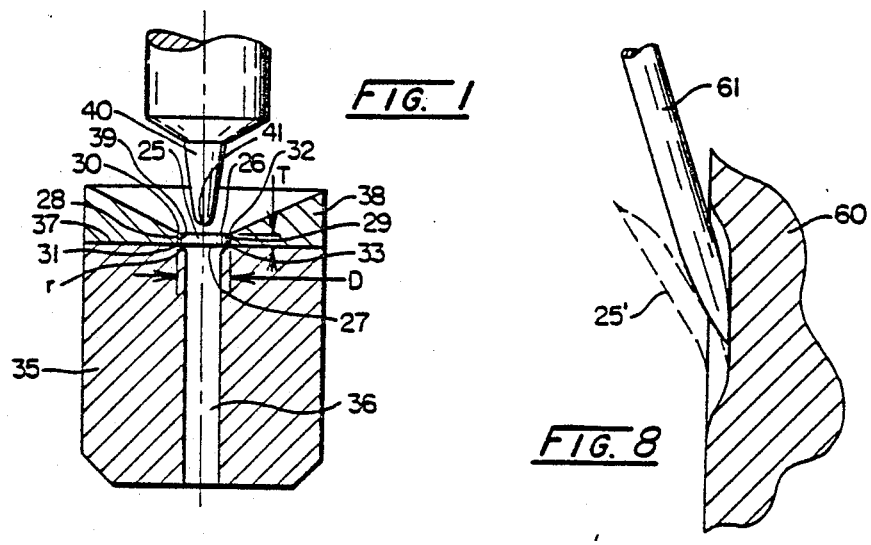
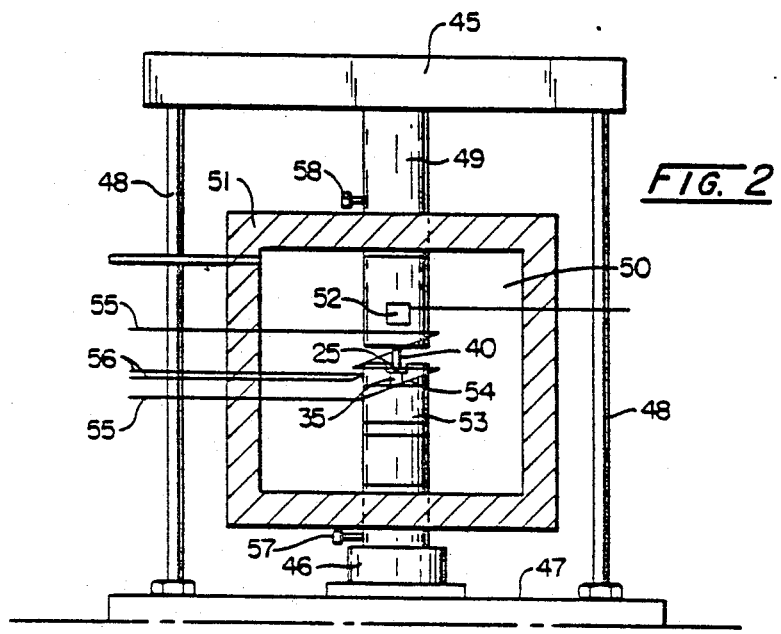
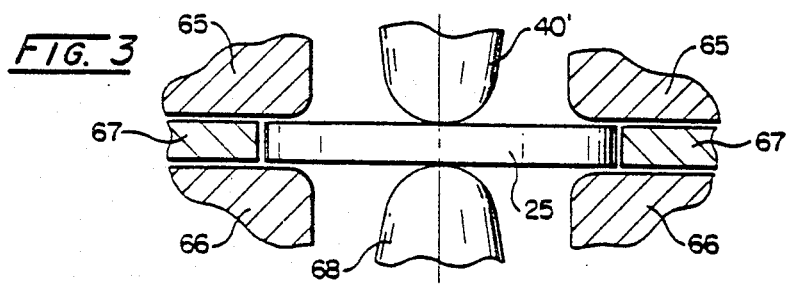

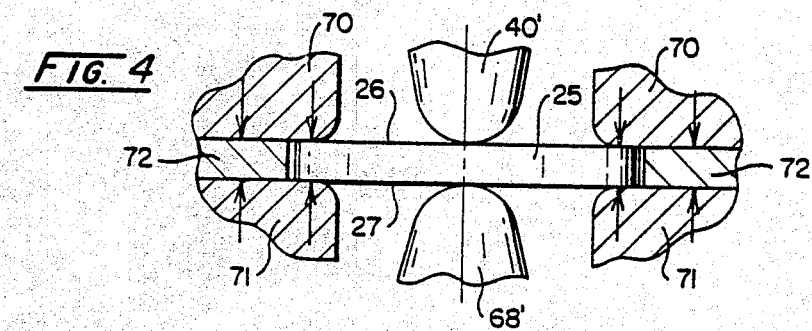
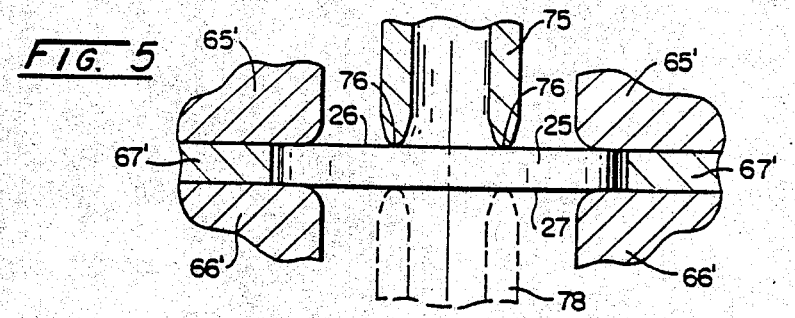
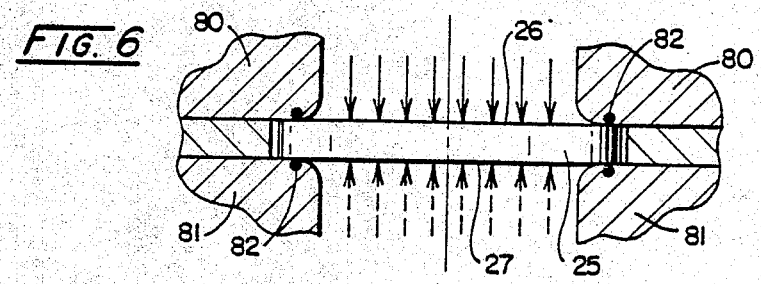
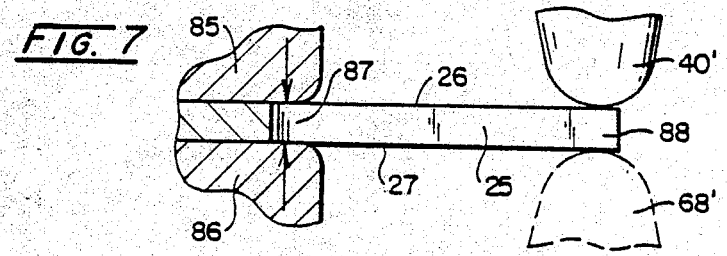

POST-IRRADIATION RESULTS FOR PATH A-1/
RAPIDLY SOLIDIFIED/20% CW MATERIAL

POST-IRRADIATION RESULTS FOR PATH A-1/
RAPIDLY SOLIDIFIED/ANNEALED MATERIAL.

FIG. 24 OUTER FIBER RADIAL STRESS RATIO AS A FUNCTION OF PUNCH DEFLECTION FOR RADIAL COORDINATES OF 0.60mm AND 0.95mm RESPECTIVELY.

FIG. 25 RESULTS OF FRACTURE INITIATION INVESTIGATION FOR 316 SS 20% CW (HEDL N-LOT)

FIG. 26 SCHEMATIC REPRESENTATION OF ABAQUS CODE UNIDIRECTIONAL GAP GEOMETRY FOR TWO BODY DUAL NODE FRICTION MODEL

FIG. 27 SCHEMATIC REPRESENTATION OF MINIATURIZED DISK BEND TEST BOUNDARY VALUE PROBLEM. THREE DIMENSIONAL PROBLEM IS IDEALIZED AS TWO DIMENSIONAL AXISYMETRIC PROBLEM.

FIG. 28  FRICTION-GAP BOUNDARY CONDITION MODEL SCHEMATIC FOR MINIATURIZED DISK BEND TEST SUPPORT. POTENTIAL PHYSICAL FRICTION NODES IN TWO DIMENSIONAL CYLINDRICAL SPACE ARE MODELLED USING SHADOW NODE PAIRS IN TWO DIMENSIONAL CARTESIAN SPACE.

FIG. 29 SCHEMATIC ILLUSTRATION OF SIGN CONVENTION AND ANGLE DEFINITIONS USED IN MULTI-POINT CONSTRAINT EQUATION DERIVATIONS

FIG. 30 FRICTION-GAP BOUNDARY CONDITION MODEL SCHEMATIC FOR MINIATURIZED DISK BEND TEST PUNCH. VELOCITY BOUNDARY CONDITION IS MODELLED BY INTRODUCING DYNAMIC CENTROID.

FIG. 33 MINIATURIZED DISK BEND TEST ROOM TEMPERATURE EXPERIMENTAL RESULTS FOR A VARIETY OF MATERIALS AND PROCESSING CONDITIONS

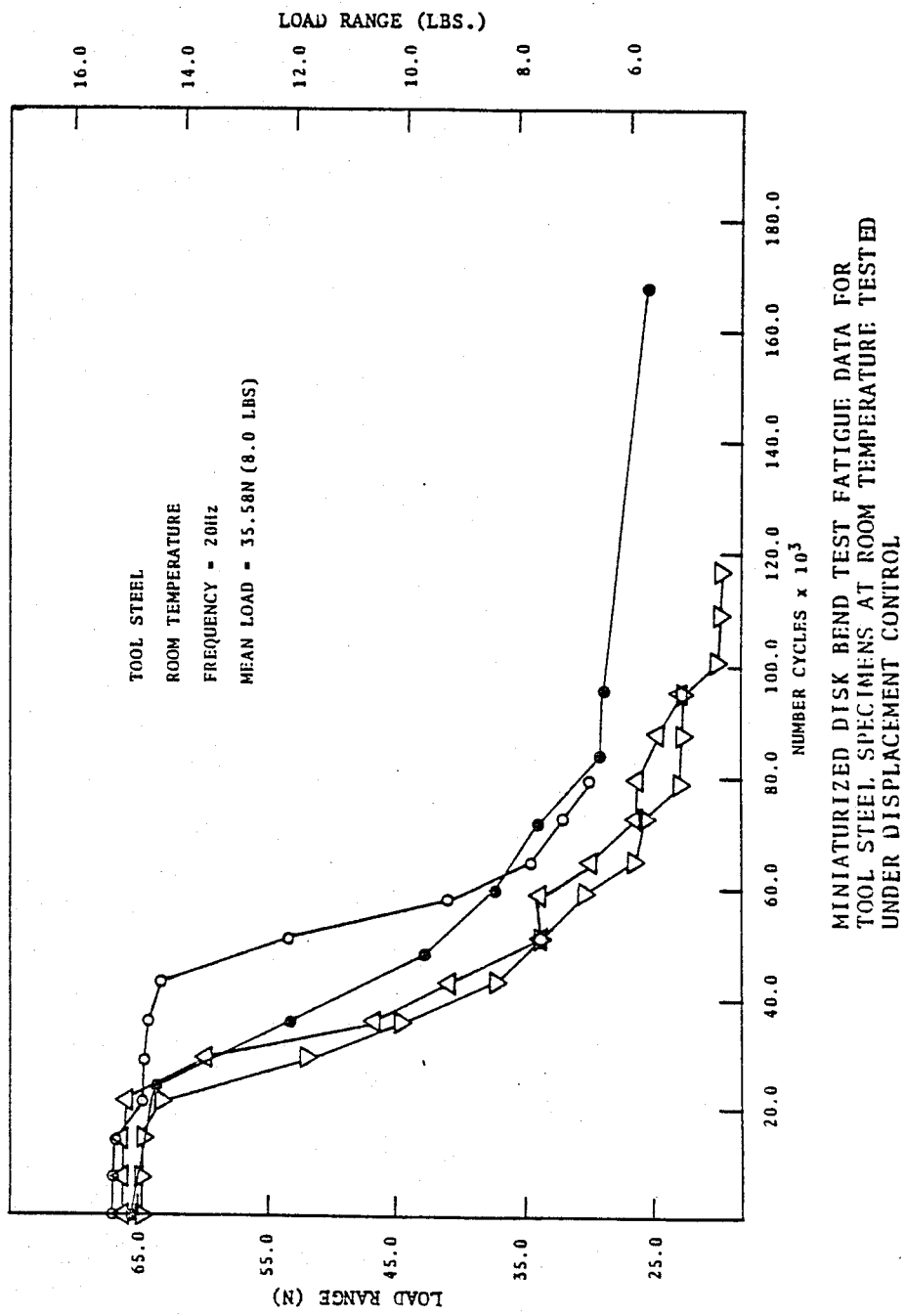

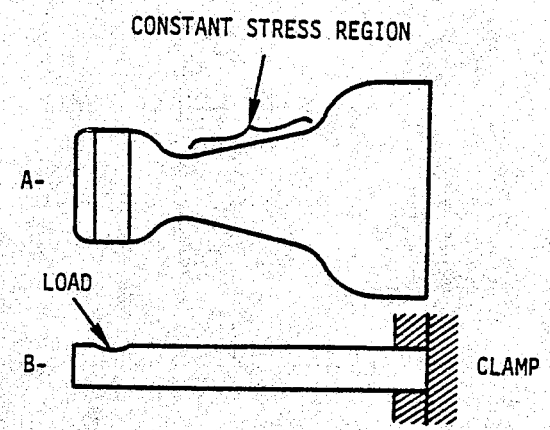
FIGURE 36. MINIATURIZED CONSTANT STRESS CANTILEVER BEAM SAMPLE
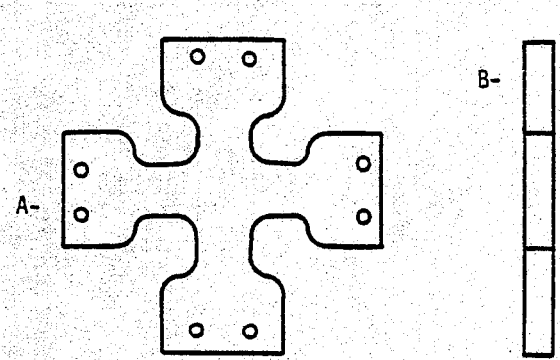
FIGURE 37. UNEQUAL MAGNITUDE BIAXIAL CRUCIFORM SAMPLE
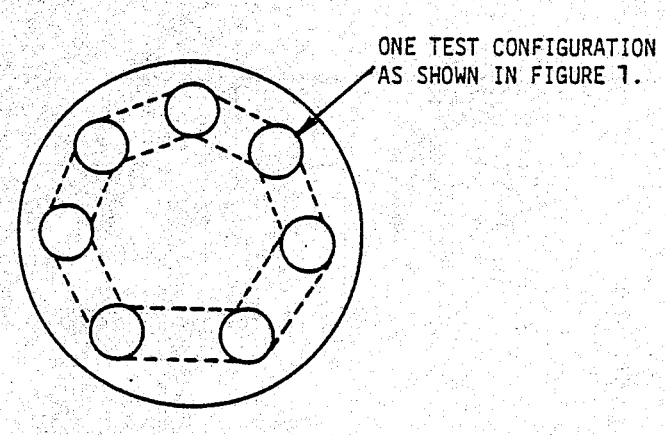
FIGURE 38. SCHEMATIC OF MULTI-SPECIMEN FATIGUE TEST APPARATUS FOR MINIATURE DISKS

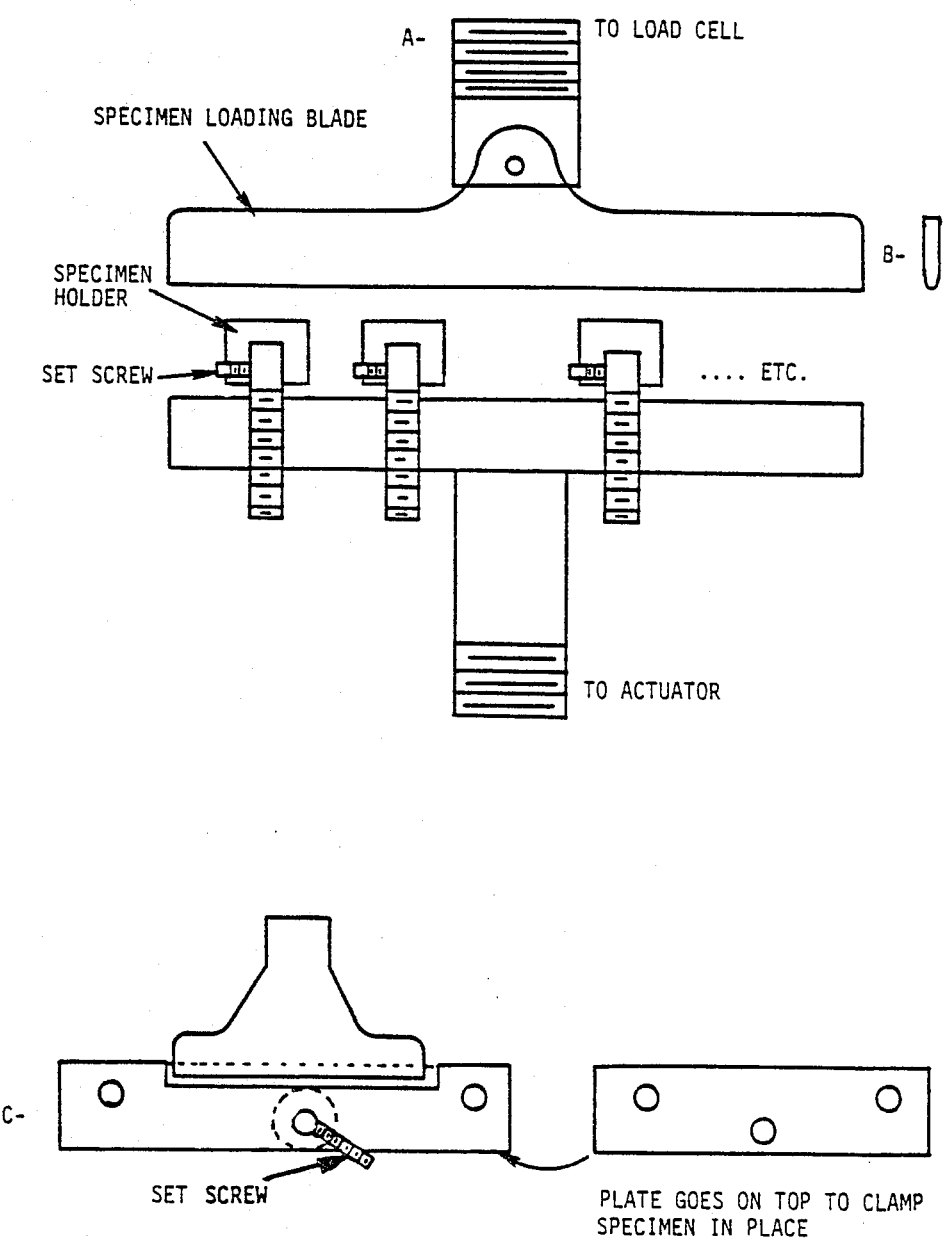
FIGURE 39. CONSTANT STRESS CANTILEVER SAMPLE MULTI-SPECIMEN TEST RIG

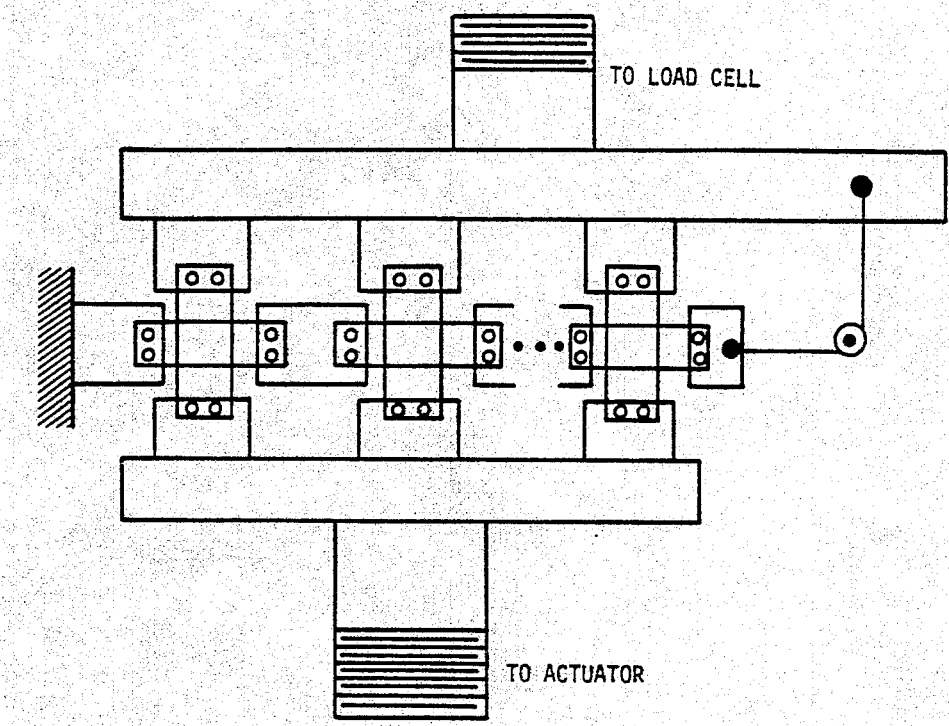
FIGURE 40. UNEQUAL BIAXIAL STRESS MULTI-SPECIMEN TEST RIG

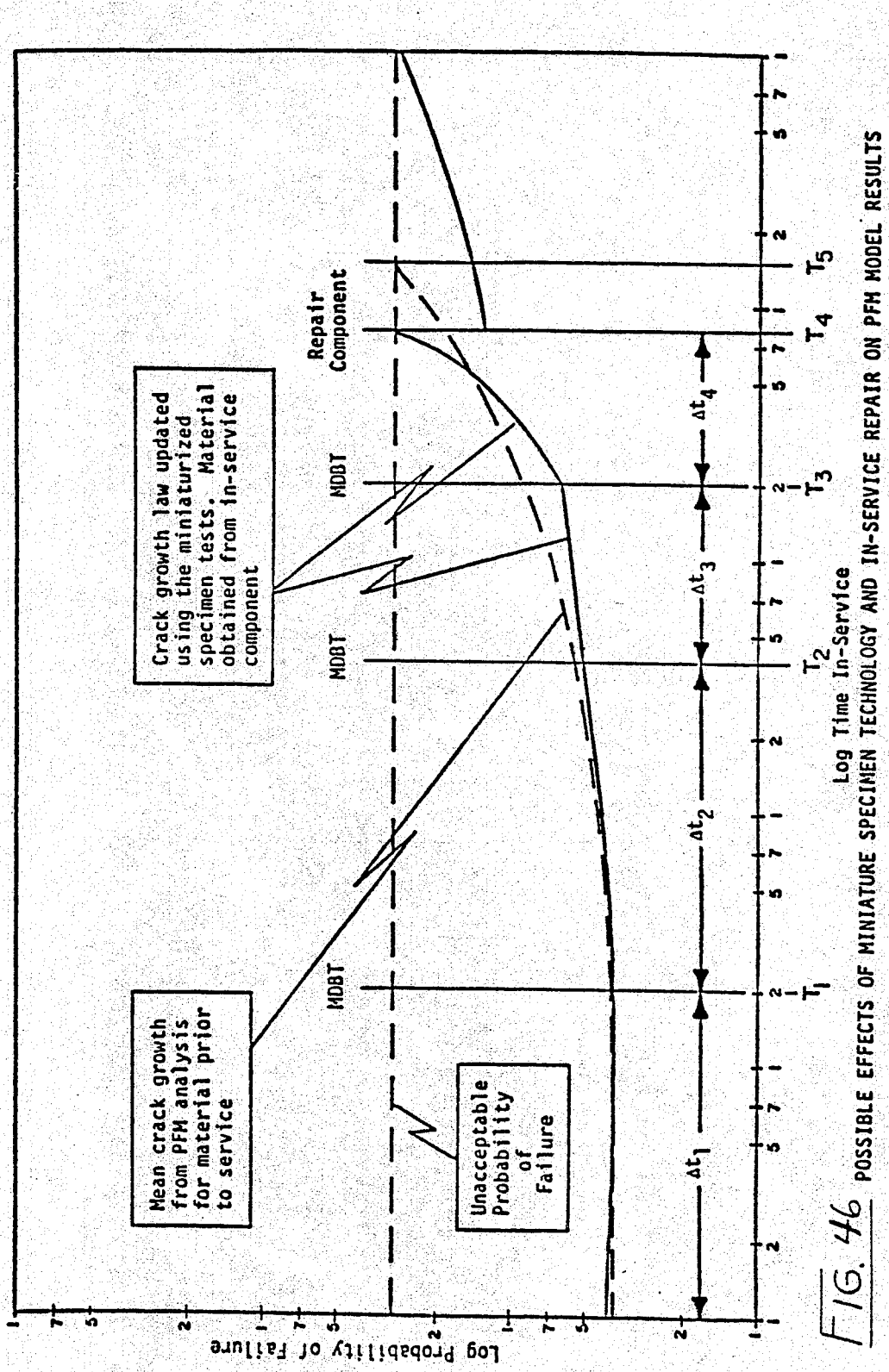
FIG. 46 POSSIBLE EFFECTS OF MINIATURE SPECIMEN TECHNOLOGY AND IN-SERVICE REPAIR ON PFM MODEL RESULTS

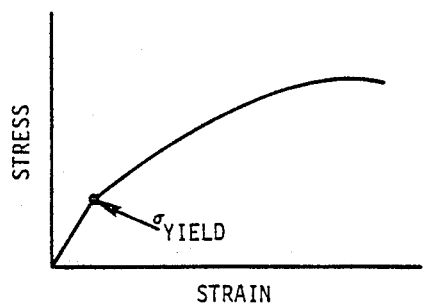
FIGURE 47. STRESS/STRAIN BEHAVIOR OF THE MATERIAL BEING TESTED
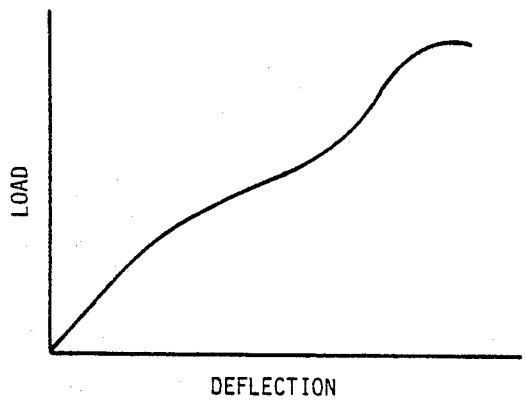
FIGURE 48. CALCULATED LOAD/DEFLECTION RESPONSE OF THE DISK
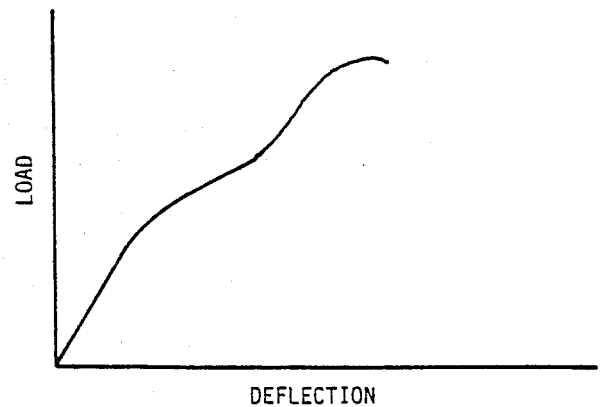
FIGURE 49. MEASURED LOAD/DEFLECTION RESPONSE OF THE DISK

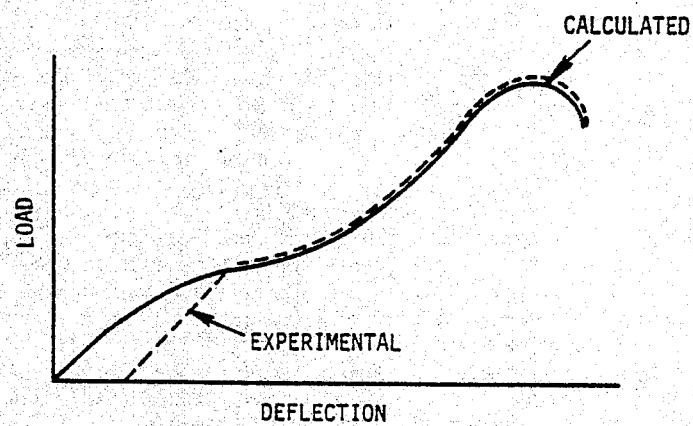
FIGURE 50. SUPERIMPOSED CURVES
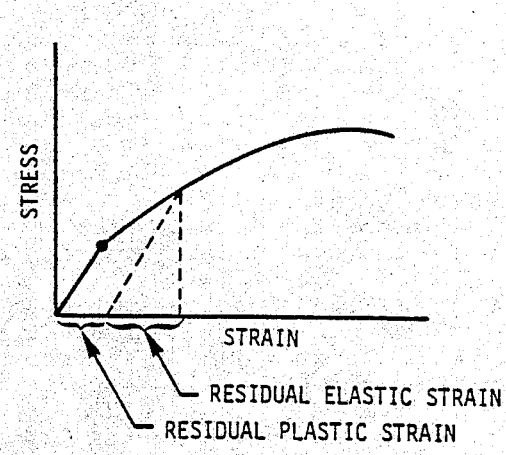
FIGURE 51. CORRESPONDING POINT ON STRESS/STRAIN CURVE

DETERMINING MECHANICAL BEHAVIOR OF SOLID MATERIALS USING MINIATURE SPECIMENS

The Government has rights in this invention pursuant to Contract No. DE-AC02-78ER10107 awarded by the U.S. Department of Energy.

FIELD

This invention relates to methods and apparatus for determining the mechanical behavior of solid material, and is especially useful for determining and measuring the behavior of materials when loaded, for the purpose of establishing the design, use, and safe life criteria of the material.

Although the term "miniature" is relative, as are all size descriptive terms, it is a fair characterization to define the field of this invention as the determination of the mechanical behavior of materials from miniature specimens; i.e., specimens noticeably smaller than prior conventional specimens in the materials testing field.

BACKGROUND

While not limited to the field of determining the effect of nuclear irradiation on the mechanical properties of materials, the impetus for the invention originated with the needs and necessities of this activity. The invention is fully applicable to the determination of mechanical behavior of materials not subjected to radiation, and the validity of the invention was demonstrated for materials not subjected to radiation.

Determination of the mechanical behavioral physical properties of materials is very necessary so that the materials may be selected for use and evaluated when in use. From these determinations, decisions are made as to which materials to use, the conditions under which they can be used, and whether materials in use can be continued with safety.

In the past, the most common procedure has been to determine the mechanical behavior of a material by testing large samples that are created more or less simultaneously or "side by side" with the product that is intended to be used. In the determination of the mechanical behavior of solid materials, and particularly metals, the practice is to make tensile, S-N fatigue, creep, stress relaxation, ductile/brittle transition, compact tension, fatigue crack initiation/propagation, fracture modes, fracture stress/strain, multilayered specimens, residual plastic stress/strain, ion irradiated, etc. specimens, and these are then subjected to forces while measurements are taken of the force, time, displacement, impact energy decrement, velocity, etc. of the specimen. Information on stress and strain, which can be thought of as normalized load and deflection respectively, are then obtained by simple mathematical operations. For example, in a uniaxial tensile test, the stress is determined by dividing the measured load by the specimen cross sectional area.

While this may be satisfactory in most instances, there are other circumstances, such as the post-irradiation testing of materials used in nuclear reactors, where samples are unavailable in sufficient size and quantity to carry out these destructive tests during the life of the materials in use. In general, neutron irradiation space for materials investigation is limited and costly. It is therefore desirable to use specimens of minimum volume. Since neutron irradiation costs scale with specimen volume, miniaturized mechanical behavior testing can provide significant savings in irradiation testing costs for nuclear materials investigations. In addition, it is possible to provide mechanical behavior information which is not ordinarily obtainable due to space limitations in irradiation experiments, and thus expedite alloy development investigations. Of course, miniature specimen testing is applicable to materials investigations for other nuclear technologies as well as non-nuclear technologies requiring mechanical behavior characterization from a small volume of material.

While the phenomenon of nuclear radiation on materials is complex, it is well known that materials change in various properties, often drastically, when irradiated. The materials used in nuclear reactors must be pretested under simulated inservice conditions, developed to an optinium design state, and often further tested while in service.

The tensile behavior of a material as the term is used herein is determined from the stress/strain curve measured on the material when subjected to various processes of loadings. The stress/strain curve for a material is most often determined by gripping a large specimen at opposite ends and subjecting the specimen to tension while measuring the load and displacement as a function of time. Since the forces can be high, there is a practical minimum limit to the size of the specimen, as there must be material available for testing, gripping, and there must be room for the apparatus to perform the gripping function. These considerations also apply to other conventional mechanical behavior tests such as fatigue, creep, stress relaxation, ductile/brittle transition, compact tension, etc.

The present invention was conceived as a solution to the problem of determining mechanical behavior from specimens which are smaller in size than the conventional test specimens. There are three principal conceptual innovative aspects to the miniaturized bend test (MBT) of this invention. The first is the use of specimens that are significantly smaller than those currently in use or that are significantly smaller than the in-service components from which they are cut. The second is the use of the appropriate loading configuration to either accommodate the size scale involved or better represent the actual in-service loading. In practice, bending is used to extract mechanical behavior information from a very small sample as opposed to the more standard approach of using uniaxial tension/compression loading requiring gripping extensions. The third is the use of the finite element method to extract useful engineering information from the experimental data.

Others have made suggestions in this field and their publications are listed further in this specification. Their publications and the Thesis cited in the next paragraph are incorporated herein by reference as fully as if they were presented in complete text.

This invention is described in further complete detail in the Thesis entitled, "The Development of a Miniaturized Disk Bend Test for the Determination of Post-Irradiation Mechanical Behavior", by Michael Peter Manahan (an applicant herein),—submitted to the Department of Nuclear Engineering in Partial Fulfillment of the Requirements for the Degree of Doctor of Science at the Massachusetts Institute of Technology—May 1982 (1).

The determination of a stress/strain curve, using analytical expressions from a pure bending test with large specimens, was first reported by Herbert (2) for cast iron bars. More recently, Crocker (3) has obtained stress/strain information for large specimens with large deflections and small strains using a three point rotary bend test. He used the same analytical expressions as Herbert and implemented a progressive reconstruction technique to transfer the moment-angle measurements into a stress/strain relationship. Stelson et al. (4) have used an adaptive controller to measure force and displacement during brakeforming of large components to estimate workpiece parameters with a microcomputer, which are then used in an analytical elastic-plastic material model to predict correct final punch position. Although the earlier developments have been useful, particularly in the metals forming industry, they are not readily adaptable to miniaturized mechanical behavior testing because of large specimen size and awkward loading configuration. A coarse ductility screening test for miniature disks, with very small ductility, has also been developed (5) using elastic analytical equations. The earlier developments have not recognized or suggested the advantages of bend testing of miniature specimens of a size at or close to the limit of continuum behavior in the material in all directions. The advantage of the finite element method for data inversion in the MBT is that it permits the extraction of both plastic resistance and creep resistance from the raw data in addition to the information on ductility from irradiated samples exhibiting moderate to large levels of strain to fracture and with a minimum of material.

Finite element analysis is performed to convert the experimental central load/deflection curves into stress/strain and other useful engineering information. In order to accurately analyze the MBT using the finite element method, a new finite element frictional contact boundary condition model has been developed (1). The strain field present in MBT is, in general, highly non-uniform throughout the sample unlike the more conventional uniaxial tensile strain fields which are constant (in the gage section) for a given static load up to the point of plastic instability. Therefore, accurate three-dimensional boundary condition modeling is essential in simulating the actual strain gradients in the specimen during the experiment. The model accounts for this highly non-linear boundary value problem with shifting frictional contacts.

The MBT problem contains all three types of non-linearity that can be encountered in stress analysis; namely, material, geometric, and boundary. The first two classifications of non-linearity have been adequately addressed in several general purpose finite element codes (6, 7). The latter classification of non-linearity has not been adequately addressed to date, and therefore a new finite element friction-gap boundary condition model has been developed. Although the model has been applied to the MBT problem in particular, the method developed is of general applicability to a wide variety of boundary condition problems.

Various methods to deal with friction in the finite element method have been proposed during recent years, primarily for application in the metalforming industry. Nagamatsu et al. (8,9) have introduced a slip-factor which is used to modify surface nodal displacements. Gordon and Weinstein (10), Iwata et al. (11) and Odell (12) have imposed surface nodal forces which are oppositely directed to the nodal displacement direction. A similar technique for opposing surface nodal displacement has been proposed by Shah and Kobayashi (13) and Matsumoto et al. (14) by introducing a surface shear stress which is evaluated from an empirical constant. As formulated by these authors, both the force method and the surface shear stress method are only applicable to problems where the direction of nodal displacement is known prior to the start of the analysis. Sharman (15) and Zienkiewicz et al. (16) have proposed interfacial friction elements for very small deformations which do not require prior knowledge of the direction of nodal displacemented, and utilized them successfully for very small deformations. Hartly et al. (17) have extended this idea to include large deformations. They found that for relatively small deformations the interfacial element layer exhibits unstable deformation and subsequently collapses. They circumvented this difficulty by introducing an element layer stiffness modifying function which depends on the ratio of the yield stress of the surface layer to that of the bulk material. The technique was applied to ring compression and satisfactory results achieved. Although this method appears promising for simple geometries, the validity of this approach has yet to be demonstrated for complex loading geometries. Also, this method, as currently formulated, does not account for shifting contact during the deformation process.

Thus, it is obvious that a new finite element friction model development, which does not depend upon prior knowledge of the deformation kinematics and accounts for shifting contact, is necessary. The model developed herein satisfies these criteria and also requires no kinematic assumptions other than the external boundary condition constraints.

The ABAQUS (6) computer code was chosen for this modeling application because of its superior non-linear capabilities. Some of the more important capabilities necessary to adequately model the MBT non-linear boundary value problem are as follows:
 1. two dimensional axisymetric continuum elements
 2. multi-linear material hardening
 3. large rotations/large displacements
 4. finite strains At the time of the work described herein, ABAQUS had all of these capabilities with the exception of finite-strain theory. (This capability has since been added.) The code implemented small-strain theory with large rotations and large displacements. Rodal has compared finite-strain theory with small-strain theory (18). He compared these two formulations for thin structures (such as beams, rings and plates) and concluded that large differences between the finite-strain theory and small-strain theory results exist for strains greater than approximately 5.0% or larger. These differences were found primarily at regions where large strain gradients occur. However, for high fluence post-irradiation materials investigations at elevated temperatures the small-strain theory may prove adequate in many instances since the ductility of many materials under these conditions is reduced.

Another very important aspect of the ABAQUS code is the fact that it contains a simple two body dual node friction model applicable to cartesian space. The code uses classical Coulomb friction with a stiffness in stick method to aid convergence. This simple model can be used as a basic building block to accurately represent multiple node frictional contact boundary conditions for essentially any geometry by the introduction of the shadow node concept. This theory enables mapping of the region of contact between a support and a deforming structure in contact with it from two dimensional cylindrical space, for example, to two dimensional cartesian space where the code can solve the friction problem. The method is of general applicability.

In essence, two fictitious shadow nodes are introduced into the analysis, somehwere in cartesian space, for every real physical node in the plate that is a potential contact/friction node. One of the shadow nodes models the plate while the other models the deforming structure. Multi-point constraint equations are written to eliminate the plate shadow node degrees of freedom. In this fashion, the friction-gap problem is effectively mapped from two dimensional cylindrical space to two dimensional cartesian space where the code can model two body dual node friction. Since the method operates directly on the plate nodes, it can therefore be termed a direct boundary condition method as opposed to the indirect methods which use interfacial elements. The method is implemented in such a way that the friction forces always oppose the direction of nodal displacement since we map the slip displacements to cartesian space as well. Therefore, when a node changes direction, the nodal surface force automatically changes sign. Also there are no kinematic assumptions on the deformation. Therefore, a solution correct to within the limitations of continuum mechanics is obtained. Phenomena such as separation of the punch and plate near the center are automatically taken into account in this model.

Eight-noded two dimensional axisymetric continuum elements were used for analysis of the MBT experiment. Isotropic hardening with a von Mises yield function was used in all analyses. In the isotropic formulation, the code requires the tangent modulus. Therefore, the uniaxial work hardening curves were multi-linearized in such a way that the energy of the work hardening curves remains approximately constant. Since all elements in the plate are initially rectangular, advantage of superconvergence is taken by using reduced integration.

Limit analysis studies were performed to test out the friction-gap model. The support model was activated and an elastic solution performed for a point loaded plate. The 20 element mesh, which consists of 2 elements through the thickness and 10 elements along a radius, was used. The true plate response lies between two bounds: (1) a roller support which corresponds to a friction coefficient of zero; (2) a fixed node support which corresponds to an infinitely large coefficient of friction. The results using the friction-gap support model with zero and infinitely large friction coefficients were identical to the results obtained using roller support and fixed node support boundary conditions respectively. The friction-gap model limit analysis results using ABAQUS were also compared with the ADINA (7) code results for support boundary conditions with zero and infinitely large friction coefficients for a point loaded plate and were found to be essentially identical.

The friction coefficient for clean stainless steel on clean high density alumina lies between 0.2 and 0.6 (19), and a value of 0.4 was used in all MBT analyses. The mean coefficient of friction has been shown to be approximately temperature insensitive for temperature variations which merely affect the mechanical strengths of the two bodies (20). This is because the ratio of the shear strength to hardness of the weaker material in contact are affected to about the same degree. Since tht MBT testing can be done in inert atmosphere, to first order, the assumption of no temperature dependence of the friction coefficient is valid.

The next step in friction-gap boundary condition model verification was, of course, to activate both the punch and support models and run an elastic-plastic analysis and compare with the MBT data. This has been done and excellent agreement between finite element prediction and experimental data has been observed.

A mesh refinement study was performed to verify that the 20 element mesh is sufficiently refined. A 100 element mesh was run and the solution compared with the 20 element mesh solution. The 100 element mesh consisted of 4 elements through the thickness and 25 along a radius. The results were essentially identical away from the punch. Near the punch, the solution differed somewhat because the boundary conditions were different. The 100 element model is inherently less stiff and also has more potential friction nodes per unit surface length. This results, in general, in more punch surface contact with the plate. There were some slight differences in the central load/deflection response. The 20 element mesh was judged adequate from a mesh refinement standpoint and was used in all subsequent analyses.

SUMMARY OF THE INVENTION

This invention comprises a process of determining mechanical behavior of solid material comprising: (a) providing a specimen of the material having at least a volume and smallest dimension sufficient to satisfy continuum behavior in all directions and with the volume not more than $10^7$ times said sufficient volume; (b) bending or otherwise deforming the specimen by applying a load on the specimen; (c) measuring at least one key variable in step b, such as the applied load or the displacement of the specimen resulting from the load; and (d) determining the tensile behavior of the material from the measurements taken according to the principles of the finite element method, and/or determining other mechanical behavior of the material from the measurements taken according to the principles of linear or nonlinear material mechanics, or both.

The invention includes carrying out the process by a code which is constructed according to the finite element method.

An object of this invention is to provide a method of determining the mechanical behavior of solid materials from specimens with only sufficient volume and smallest dimension to satisfy continuum behavior in all directions. It is a feature of this invention to provide a method of determining the mechanical behavior of solid materials accurately by bending miniature specimens. Still a further feature is to determine the mechanical behavior accurately by the finite element method.

Another feature is to determine the mechanical behavior by the processes of continuum material mechanics carried out by a code which is applied according to a predetermined algorithm which has been determined to be statistically accurate.

An overall object of the invention is to provide the capability of determining mechanical behavior of material through a process requiring substantially less material than used with conventional techniques, and a process using specimen sizes so small that they may be trepanned from the elements of existing structures without significantly altering the overall characteristics of the structures.

Other objects and features of this invention will be apparent from the detailed description of the invention and the accompanying drawings which follow.

DESCRIPTION OF THE DRAWINGS

FIG. 1 is a sectional elevational view of a specimen of solid material in simply supported position for the practice of the process of this invention.

FIG. 2 is a schematic elevational view of typical apparatus in which a specimen is supported during the practice of this invention.

FIG. 3 is an elevational sectional view of a portion of the apparatus in which the process of this invention is carried out alternately and/or repetitively.

FIG. 4 is an elevational sectional view of means for practicing another embodiment of this invention.

FIG. 5 is an elevational partially sectional view of another means for the practice of this invention.

FIG. 6 is an elevational partially sectional view of still another means for the practice of another embodiment of this invention.

FIG. 7 is an elevational partially sectional view of a process of carrying out this invention in a cantilever mode embodiment.

FIG. 8 is a sectional view of a portion of an inservice material upon which a process of this invention may be carried out in still another embodiment.

FIG. 12 illustrates uniaxial tensile data for large specimens for 316 SS 20% CW (N-LOT Material) at 482° C. Also shown is the power law fit to the data as well as the multi-linear hardening approximation of the data for use in the finite element analysis.

FIG. 13 shows a demonstration of validity of miniaturized disk bend test methodology. The finite element solution generated using the known uniaxial stress/strain behavior shows excellent agreement with the miniaturized disk bend test data.

FIG. 14 illustrates a multi-linear hardening approximation of flow curve varied by 2% and 10%, respectively, to assess the miniaturized disk bend test stress/strain resolution capability.

FIG. 15 shows the calculated applied central load/deflection curves for the 2% and 10% change in flow curve compared to the experimental reproducibility band.

FIG. 16 illustrates the percent change in calculated applied central load for 2% and 10% change in flow curve input.

FIG. 17 shows an uncertainty mapping function from uniaxial tensile stress space to miniaturized disk bend test applied central load space.

FIG. 18 illustrates the post-irradiation results for the path A-1/rapidly solidified/annealed material.

FIG. 19 shows the post-irradiation results for the path A-1/rapidly solidified/20% CW material.

FIG. 20 illustrates a spectrum of parameterized flow curves used to invert post-irradiation data.

FIG. 21 shows a spectrum of applied central load/deflection curves generated from the finite element analysis using parameterized flow curves.

FIG. 22 illustrates the post-irradiation data inversion of rapidly solidified materials using the miniaturized disk bend test methodology.

FIG. 23 shows a fundamental interpretation of applied central load/deflection curves for 316 SS 20% CW.

FIG. 24 illustrates an outer fiber radial stress ratio as a function of punch deflection for radial coordinates of 0.60 mm and 0.95 mm respectively.

FIG. 25 shows the results of the fracture initiation investigation for 316 SS 20% CW.

FIG. 35 is a graph showing MBT fatigue data for tool steel at room temperature.

FIG. 36 is a plan view of a beam specimen showing a constant stress configuration.

FIG. 37 is a plan view of a biaxial cruciform specimen which can be used in another embodiment of this invention.

FIG. 38 is a schematic plan view of multi-specimen fatigue test apparatus for miniature disk determinations.

FIG. 39 is a schematic elevational view of a multi-specimen cantilever test fixture for use in another embodiment of MBT process.

FIG. 40 is a schematic elevational view of a multi-specimen biaxial cruciform specimen test fixture for use with the MBT process.

FIG. 46 is a graph showing possible effects of miniature specimen technology and in-service repair on PFM model results.

FIGS. 47-51 are graphs of results in progressive steps of residual plastic stress/strain determination in another embodiment of the process of this invention.

DETAILED DESCRIPTION OF THE INVENTION

Figure 9:
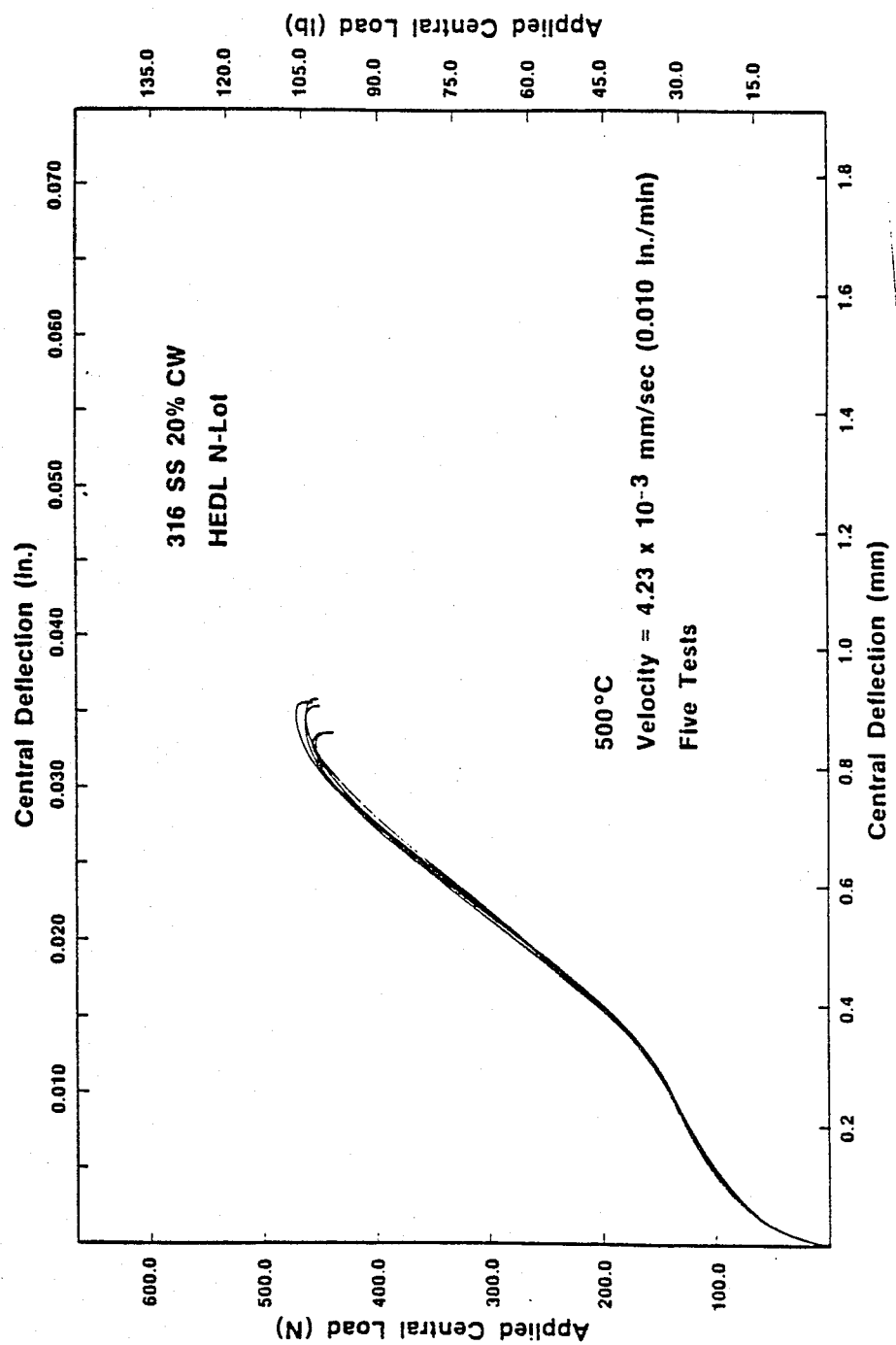
FIG. 9 is a graph showing miniaturized bend test reproducibility with total eccentricity of loading of 0.0178 mm for elevated temperature, five separate tests. All curves are within 3.2% of the mean along the entire curve to the point of fracture initiation.

Referring to FIG. 1 a typical process according to this invention is carried out on a specimen 25 in the shape of a disk having an upper face 26 and an opposite (lower) face 27, a (left) side 28 and an opposite (right) side 29. It will be understood that sides 28 and 29 are the representations of the continuous side surface of the disk 25 which has a circular periphery. Sides 28, 29 meet the faces 26, 27 at a left upper edge 30, a left lower edge 31, a right upper edge 32, and a right lower edge 33. The disk has a thickness or gage T between the faces 26 and 27.

The disk 25 is simply supported on a die 35 having a bore 36, and an upper surface 37 in planar contact with a positioning washer 38 which has an aperture 39 with a diameter only slightly larger than the diameter D of the disk 26.

A rounded nose punch 40 having an end 41 is positioned above the disk 25. Punch 40, the washer 38, bore 36, and the disk 26 are substantially coaxial to provide symmetrical positioning of the elements of the specimen during the operation of the process to be later described.

Tyically the junction of the bore 36 and the surface 37 is provided with a radius, where r is bounded by the limits r=zero and r=infinity.

In the preferred embodiment the punch 40 surface 41 is bounded by these limits $r_p$=zero and $r_p$=infinity, where $r_p$ is the punch radius of curvature.

In typical processes of this invention a load is applied to the face of the disk 26 by forcibly moving the punch vertically downward on the central axis of the apparatus and applying a load P to cause displacement and strain in the disk.

Included in typical practice of the invention is the measurement of key variables such as the time variation of the load P, the time variation of the displacement d, the velocity of the punch 40 and the temperature of the specimen 25 and its environment. Apparatus to control and measure these factors is shown in FIG. 2 in which a conventional compression loading test apparatus of the "Instron" type includes a cross head 45 oppositely disposed to an actuator 46 and connected thereto by tension members 48. The actuator 46 is operable upward from a frame/platform 47. Tension members 48 connect the cross head 45 and the frame 47.

A water cooled upper compression rod 49 extends into an environmentally controlled chamber 50, surrounded by an insulated wall 51, and supports a water cooled load cell 52 that carries the punch 40. The specimen 25 is supported beneath the punch 40 on the die 35 as shown in FIG. 1. The die 35 is carried on a thermally insulated water cooled compression rod 53 which is supported on the actuator 46. An induction heating coil 54 surrounds the area of the specimen 25, fed by inlet and outlet connections 55. Two thermocouples 56 are attached to the specimen support 35.

Axial extensometers 57 and 58 are connected to the compression rods 53, 49 respectively, so that the measurements may be made of key variables such as the distance traveled by the disk 25 and the displacement in the faces 26, 27 of the disk 25. The temperature of the specimen 25 and the surrounding area can be controlled by the induction heating coil 54 and the thermocouple 56. As necessary the environment in the chamber 50 can be controlled by the admission of inert or other gas. A stroke transducer is provided in the Instron equipment to measure the velocity of the punch 40 relative to the sample 25.

In the practice of the process of this invention, a specimen is provided of a solid material having at least a volume and smallest dimension sufficient to satisfy continuum behavior in all directions. In most ductile metal materials this volume and smallest dimension will be determined by the average grain size of the material and the fact that 10 to 15 grains usually represents a lower bound necessary to achieve continuum behavior.

The continuum behavior minimum size limit is the point where there is no variation in the average mechanical behavior response when a larger number of grains is used. The threshold limit of the successful practice of this invention, from a miniaturization standpoint, is that size below which continuum behavior in all directions is not certain to take place. To obtain the benefits of miniaturization it is not necessary to provide a specimen exactly at the minimum theoretical limit to satisfy continuum behavior. Specimens having at least a volume and smallest dimension to satisfy continuum behavior in all directions and with the volume not more than $10^7$ times that sufficient volume can be successfully practiced in processes of the invention.

The upper limit for the successful practice of the invention in a miniature bend test is not known to be a precise physical limit, and may depend more on obtaining the practical benefits from determining mechanical behavior by specimens of limited size. It is believed that $10^7$ times the minimum volume determined from continuum mechanics considerations is the practical threshold for the maximum size of a specimen when processes of the invention are to be carried out.

In a typical preferred embodiment of the practice of the invention, results have been obtained which demonstrate the efficacy and accuracy of the method. Using the apparatus of FIGS. 1 and 2, unirradiated as well as post-irradiated mechanical behavior information was obtained from such miniaturized samples.

Tensile Behavior—The determination of the tensile behavior of solid material will now be discussed. The methodology is generally applicable to the other mechanical behavior tests mentioned later in the text, and therefore will be discussed in some detail here.

Figure 32:
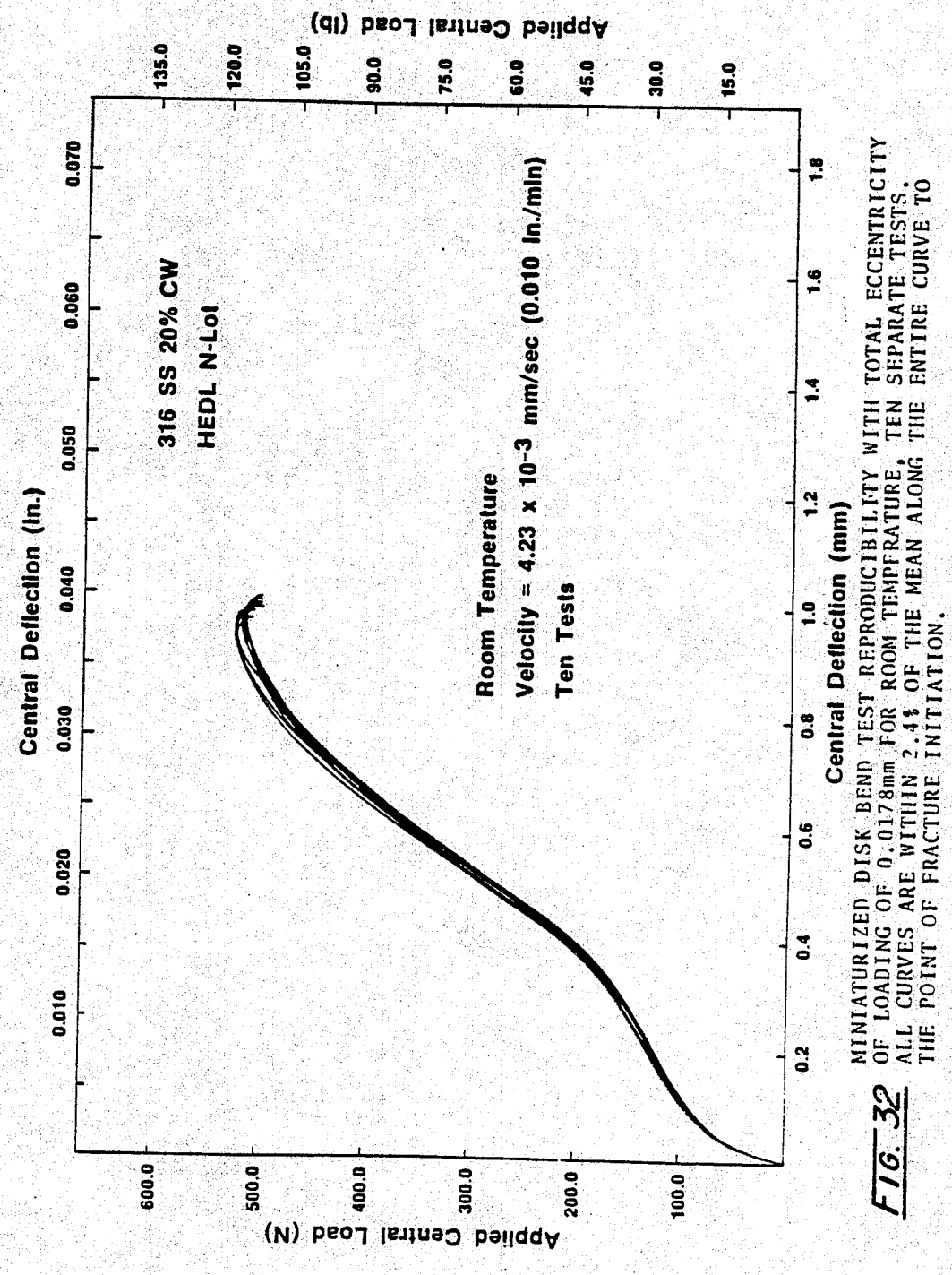
FIG. 32 is a graph showing the reproducibility of ten separate MBT tests at room temperature.
Figure 33:
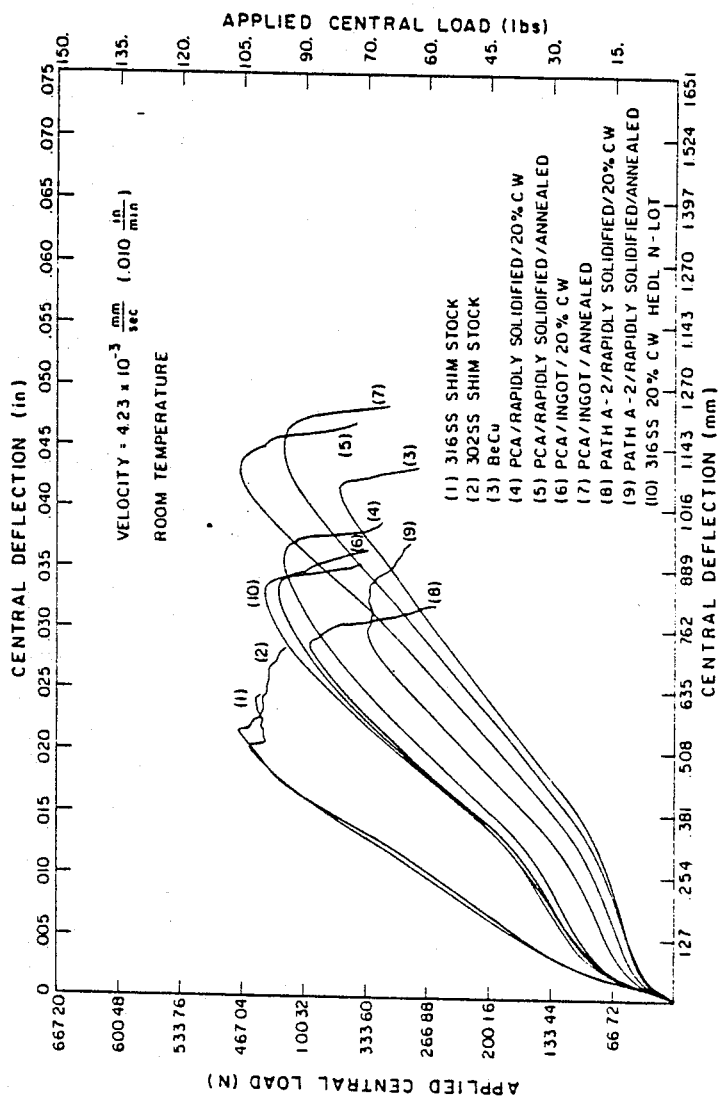
FIG. 33 is a graph showing the application of the MBT to various materials.

Experimental reproducibility for ten separate tests at room temperature is illustrated in FIG. 32. The material tested was 316 SS with 20% cold work (CW). This material was chosen because the mechanical behavior has been well characterized and should serve as a good validation of the MBT methodology.

Alignment of the punch and die as well as specimen centering are critical since disk stiffness increases with eccentricity of loading. There are two basic contributions to total eccentricity which are of prime importance: (1) punch axis of symmetry not coincident with die axis of symmetry, and (2) design tolerances for die positioning washer upper disk support structure and specimen outer diameter. The former eccentricity is controlled by using a precision alignment fixture; the latter, by careful experimentation and by accurate machining of key components. The total eccentricity of loading was measured and found to be approximately 0.0178 mm for all the curves in FIG. 32. For this eccentricity the central load/deflection curves for the ten tests fell within a band that is only 2.4% of the mean along the entire curve to the point of fracture initiation.

Another reproducibility investigation with a total eccentricity of approximately 0.0635 mm was also conducted. In this case the reproducibility band was within 4.0% of the mean along the entire curve to the point of fracture initiation.

In the experiments, specimen disks were provided having nominal dimensions D=3.0 mm×T=0.254 mm. This size specimen in 316 SS with 20% CW material has a volume and smallest dimension sufficient to satisfy continuum behavior in all directions and the smallest dimension is less than $10^7$ times the smallest sufficient dimension.

The reproducibility of the MBT was demonstrated at 500° C. on the typical material shown in FIG. 9. The material has been shown to have negligible strain rate dependence at this temperature with strain rates in the range of $10^{-5}$ sec $-1$ to 10 sec $-1$, and therefore a convenient punch velocity of $4.23\times10^{-3}$ mm per sec was used.

Specimens of this size were sectioned and metallographically studied at 116× magnification. It was determined that there were approximately six grains through the thickness T and approximately seventy grains across the diameter D for the 316 SS material. Considering that about ten grains probably represents a theoretical lower limit to achieve continuum behavior, it is clear that in the thickness direction continuum behavior is satisfied with six grains in this instance.

For materials with smaller grain sizes, such as those produced by rapid solidification, these considerations are of less concern since, in general, continuum behavior through the thickness is achieved there with a larger number of grains in a specimen of a given size.

The validity of the MBT methodology must be demonstrated for a material with well characterized mechanical behavior before it can be safely used in practice. The 316 SS 20% CW N-LOT material was chosen for this purpose. Of course, once this is accomplished, the MBT can be used to determine mechanical behavior. The problem at hand, therefore, is reduced to that of generating a central load/deflection curve using the finite element method that matches the experimental data presented in FIG. 9.

Figure 12:
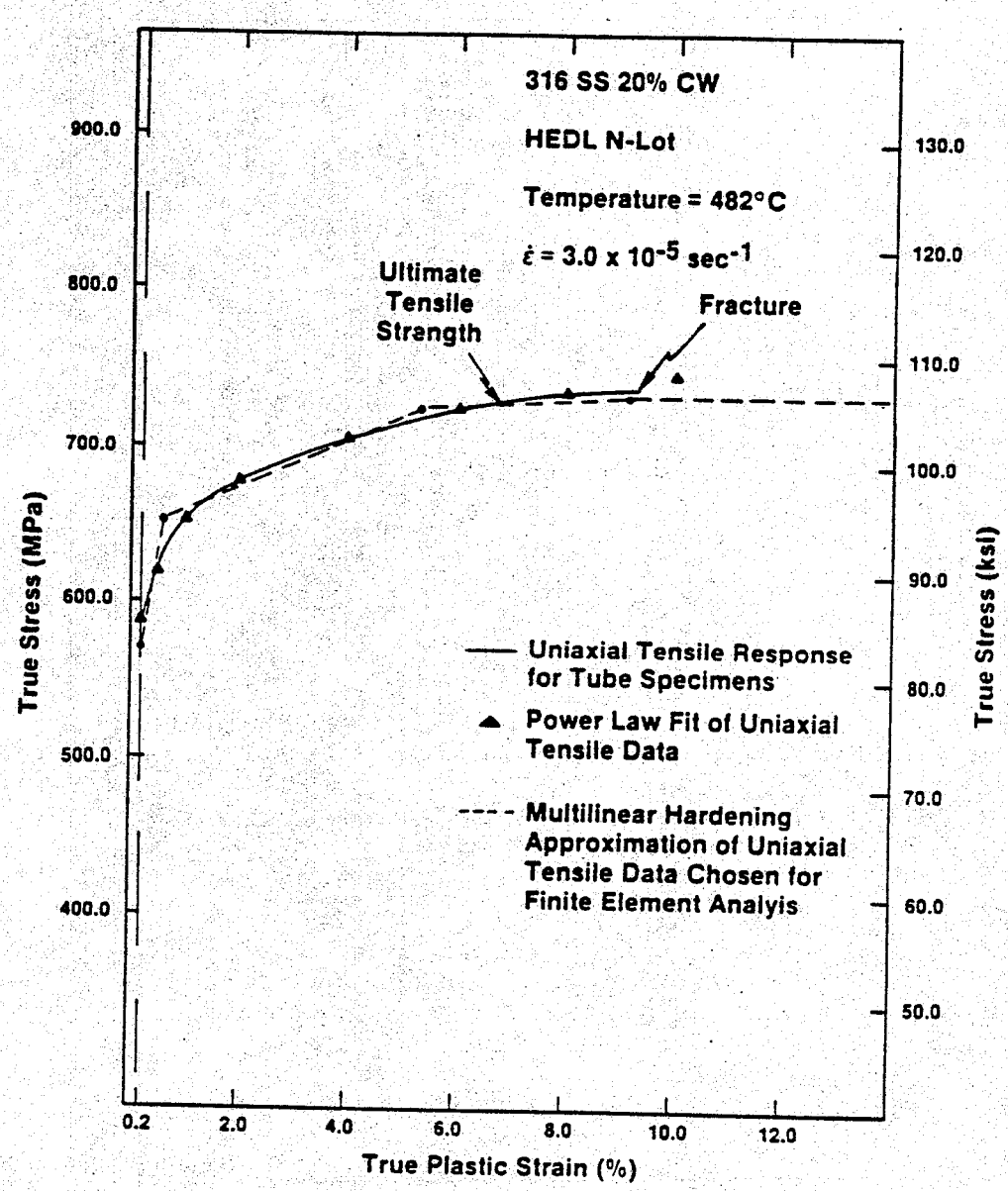
FIGS. 12–25 are graphs.
Figure 13:
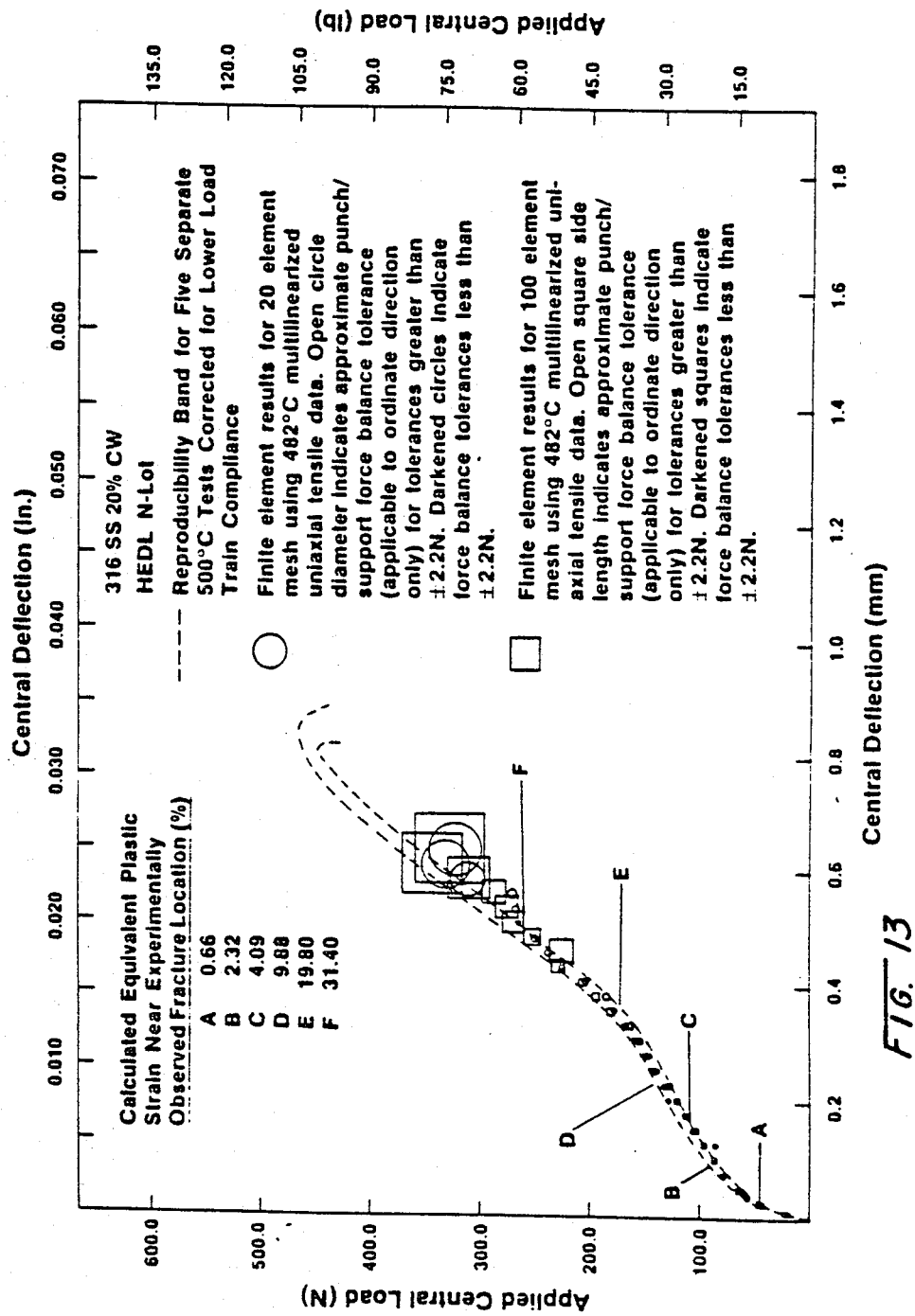

The known uniaxial tensile behavior at 482° C. of the N-LOT material (27, 28) was used as code input. The data were piecewise linearized as shown in FIG. 12. This was done in such a way as to keep the area (or energy) under the curve approximately constant. A 20 element and a 100 element mesh were run and the results of these analyses are presented in Appendices E and F, respectively, of reference (1). The applied central load and deflection output are listed in Table I, and also plotted with the FIG. 9 experimental reproducibility band in FIG. 13. The calculated equivalent plastic strain near the point on the bottom surface of the plate where fracture has been experimentally observed to occur is also shown in FIG. 13 at several places on the applied central load/deflection curve. The finite element prediction is quite accurate up to a central deflection of about 0.45 mm. The force balance tolerance provides an estimate of the central deflection beyond which small-strain theory is no longer valid. As show in FIG. 13, the convergence tolerance becomes sizeable after a central deflection of about 0.45 mm for the 100 element mesh. One of the bottom elements near the plate center actually turns in on itself at this deflection magnitude. This explains the large force balance tolerance for the 100 element mesh after central deflections of 0.45 mm. Since there are only two elements through the thickness for the 20 element mesh, this phenomenon occurs at a larger central deflection of this mesh as shown in FIG. 13. Therefore, as anticipated, for materials which exhibit large ductility, the large-strain theory must be implemented.

TABLE I

Finite Element Prediction of Central Load/Deflection Response for 316SS 20% CW N-LOT Material at 482° C.

| Central Deflection (mm) | 20 Element Mesh | | 100 Element Mesh | |
|---|---|---|---|---|
| | Central Load(N) | Convergence Tolerance(N) | Central Load(N) | Convergence Tolerance(N) |
| 0.0127 | 18.90 | 0.0 | 24.33 | 0.0 |
| 0.0254 | 46.88 | 0.0 | 44.61 | 0.0 |
| 0.0381 | 57.16 | 0.0 | 56.71 | 0.0 |
| 0.0508 | 59.87 | 0.0 | 66.10 | 0.0 |
| 0.0762 | 79.71 | 0.0 | 79.35 | 0.18 |
| 0.1016 | 85.00 | 0.49 | 86.38 | 0.18 |
| 0.1270 | 86.02 | 0.71 | 94.70 | 0.27 |
| 0.1524 | 103.86 | 1.69 | 102.66 | 0.0 |
| 0.1178 | 111.87 | 0.04 | 109.95 | 0.18 |
| 0.2032 | 128.50 | 0.67 | 119.83 | 1.29 |
| 0.2286 | 130.99 | 3.87 | 125.48 | 1.56 |
| 0.2540 | 139.00 | 3.96 | 144.07 | 1.73 |
| 0.2794 | 146.07 | 5.07 | 148.79 | 2.18 |
| 0.3048 | 161.28 | 4.67 | 153.01 | 1.96 |
| 0.3302 | 169.02 | 5.34 | 161.95 | 6.09 |
| 0.3556 | 178.68 | 5.20 | 186.46 | 7.16 |
| 0.3810 | 186.64 | 7.21 | 195.36 | 7.21 |
| 0.4064 | 205.76 | 6.04 | 206.52 | 7.03 |
| 0.4318 | 224.09 | 6.14 | 232.32 | 12.28 |
| 0.4572 | 237.70 | 6.41 | 224.13 | 22.75 |
| 0.4826 | 249.49 | 6.89 | 252.02 | 15.19 |
| 0.5080 | 261.72 | 3.47 | 268.48 | 19.39 |
| 0.5334 | 267.77 | 6.05 | 273.77 | 20.68 |
| 0.5588 | 270.79 | 9.39 | 287.47 | 21.84 |
| 0.5842 | 313.67 | 31.85 | 309.85 | 39.63 |
| 0.6096 | 331.11 | 45.68 | 346.10 | 36.22 |
| 0.6350 | 320.97 | 49.77 | 327.42 | 65.74 |

Figure 10:
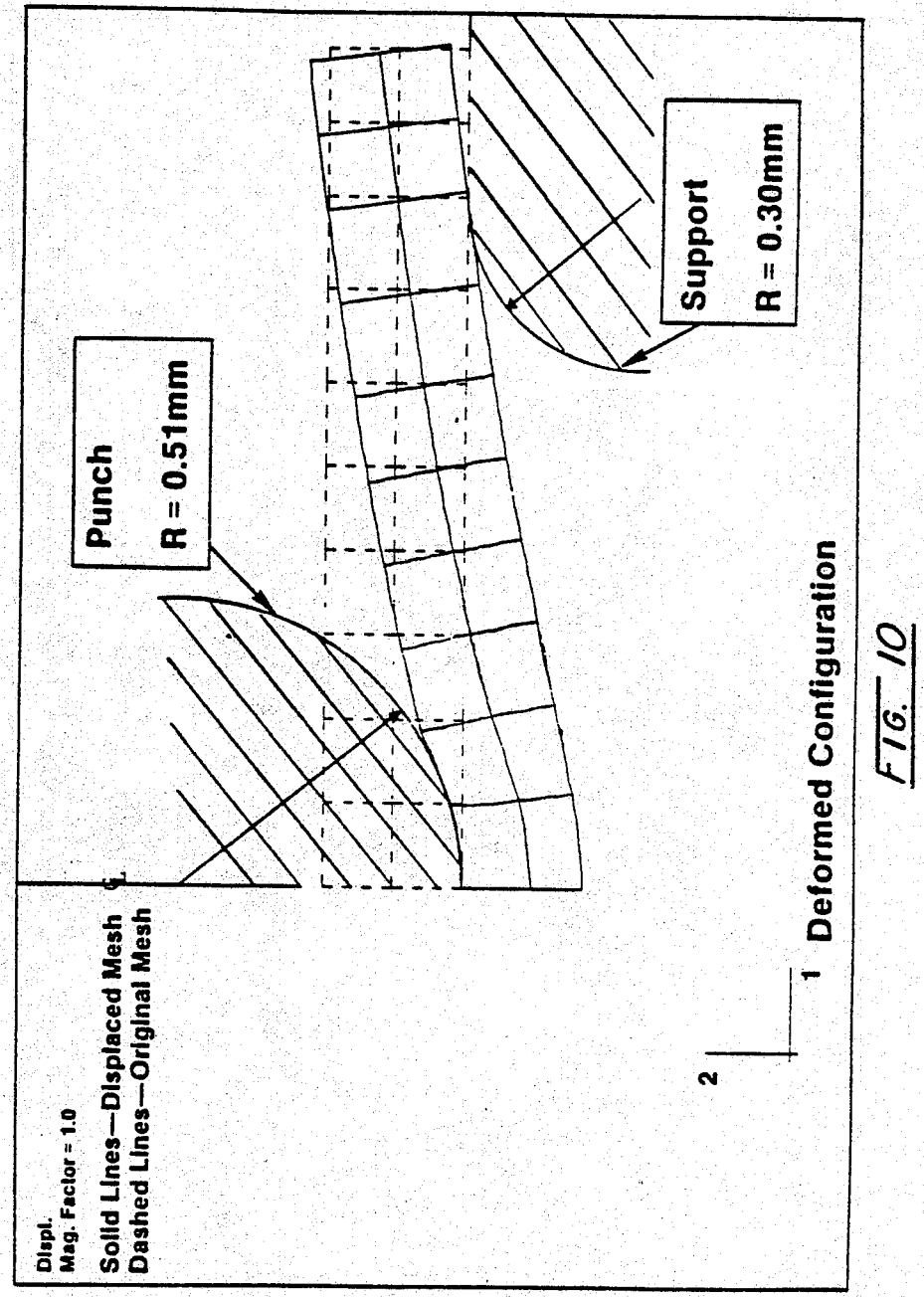
FIG. 10 is a schematic cross-sectional view of half a plate showing the finite element calculation of the deformed configuration for punch displacement of 0.254 mm.
Figure 11:
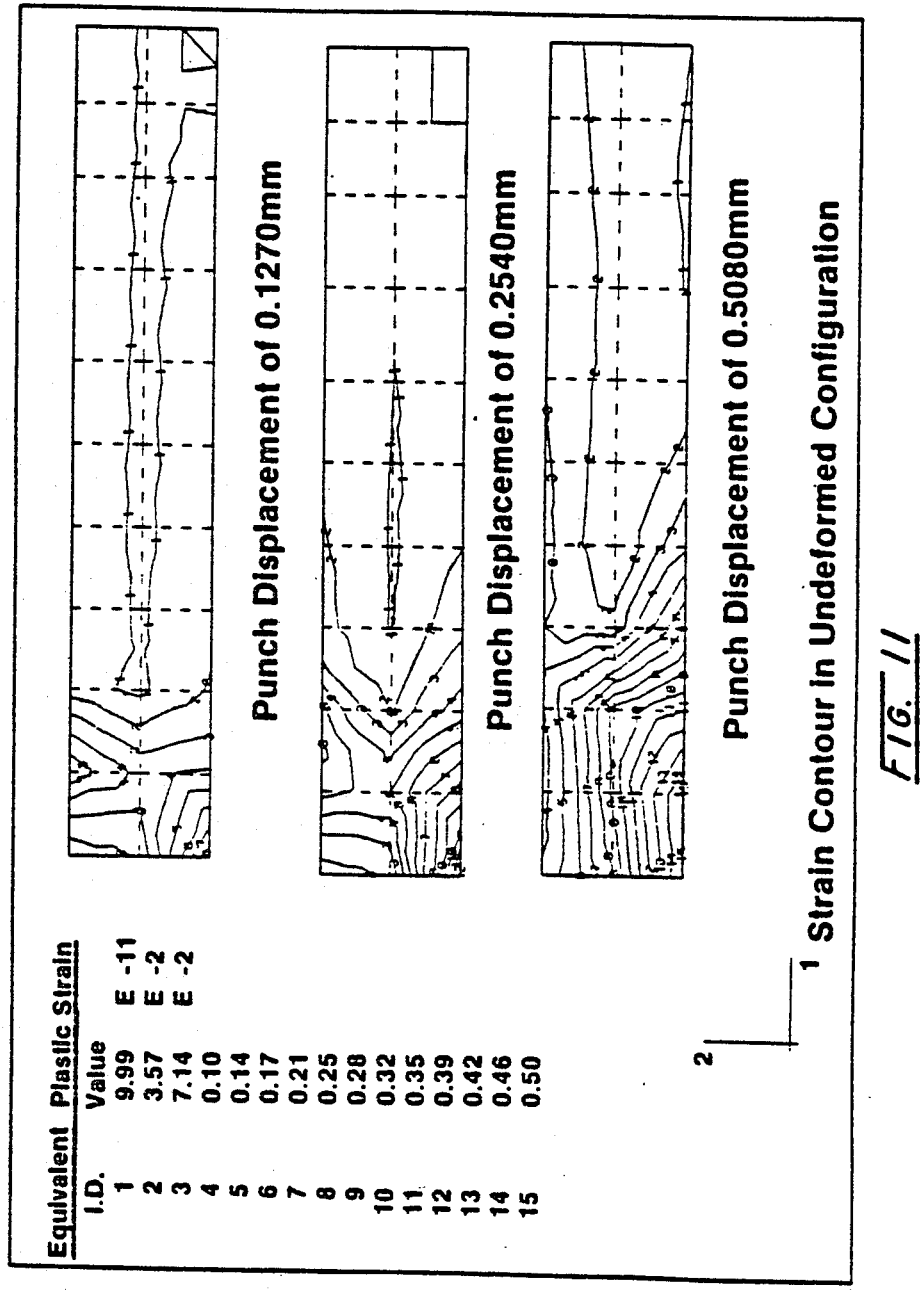
FIG. 11 is a schematic cross-sectional view of half plates showing the finite element calculation of the equivalent total plastic strain contours for various punch displacements.

A typical deformed plate configuration superimposed on the undeformed configuration is shown in FIG. 10 for a punch deflection of 0.254 mm. The equivalent plastic strain contour for this punch deflection is shown in FIG. 11.

The friction-gap model developed is a discrete model. This explains why the 100 element mesh gives a better load prediction at a central deflection of 0.13 mm as shown in FIG. 13. At a central deflection of 0.15 mm, the 20 element mesh solution agrees with the 100 element mesh solution because another plate node has come into contact with the punch. The 100 element mesh has more area in contact with the punch, in general, than the 20 element mesh and more accurately models the loading and propagation of the annular contact region along the punch surface as the deformation proceeds. The loading condition is obviously different in the two meshes which thus affects the strain distribution near the punch. However, the 20 element mesh strain distribution is similar to that calculated using the 100 element mesh away from the punch. Therefore, if uniaxial material behavior of an irradiated material is desired, the 20 element mesh is adequate and more cost effective than the 100 element mesh. However, if biaxial stress/strain information near the point in the plate where fracture initiation is experimentally observed is desired, then local mesh refinement near the punch tip is necessary for future analyses. The 100 element mesh requires approximately 5 times more running time than the 20 element mesh.

The through thickness fiber rotations near the support are initially larger than the tendency of the plate to draw into the die, which results in the bottom surface nodes displacing a small distances radially outward initially. At higher levels of deformation, these nodes reverse their directions and displace radially inward. The friction model automatically changes the sign of the surface friction force when node direction reversal occurs. Also, the finite element solution shows that all plate material points remain within a cylindrical space of diameter 3.0226 mm throughout the entire deformation for a disk of undeformed diameter 3.0 mm. This cylindrical region is adequate to ensure that the specimen will drop into place in the positioning washer. This information may be useful in future designs to minimize the tolerance between the specimen and positioning washer in the experiment to provide better alignment and also maintain the simply supported boundary condition. The model also predicts separation of the punch from the plate at the center leaving an annular section in contact for a punch displacement in excess of 0.15 mm. In general, excellent agreement between the finite element prediction and the experimental data has been observed.

Figure 14:
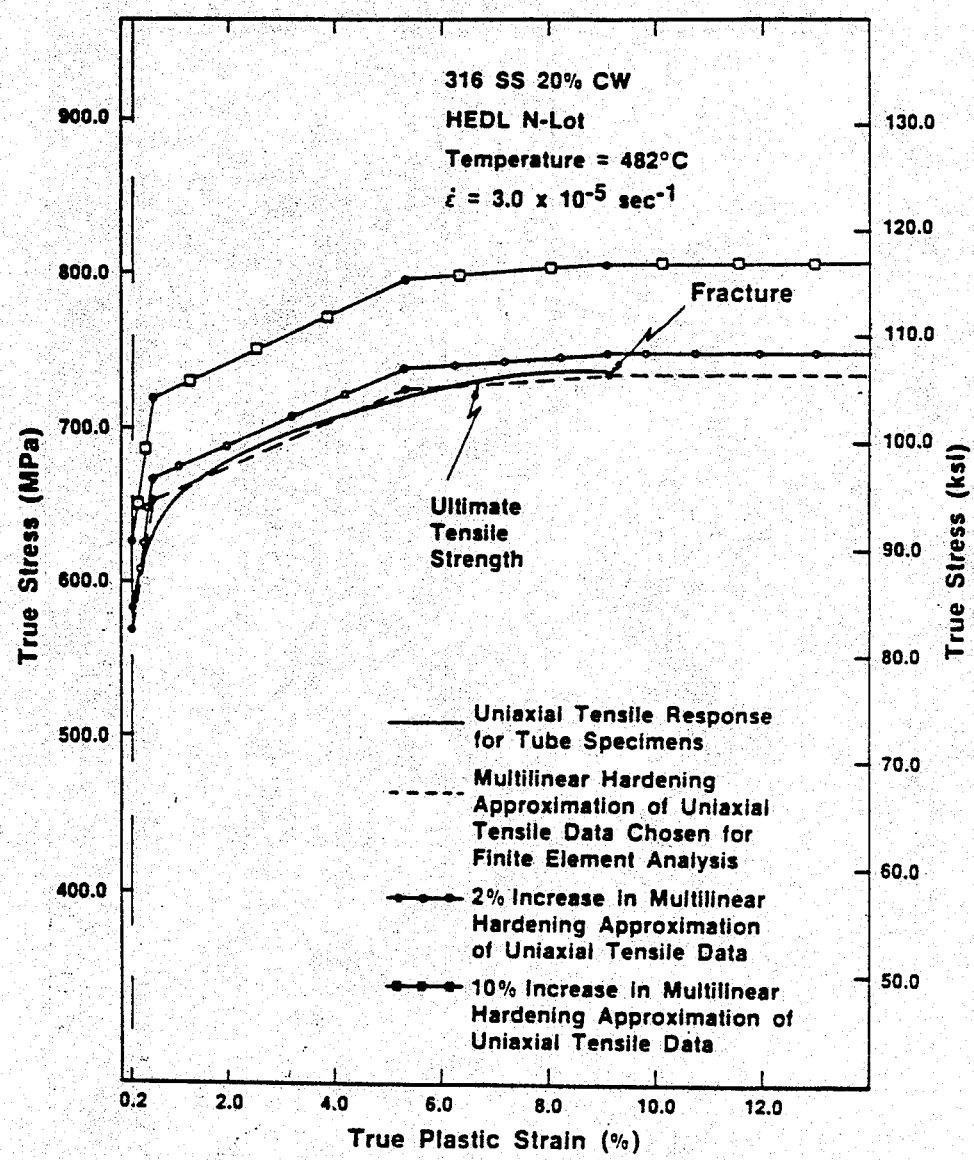
Figure 15:
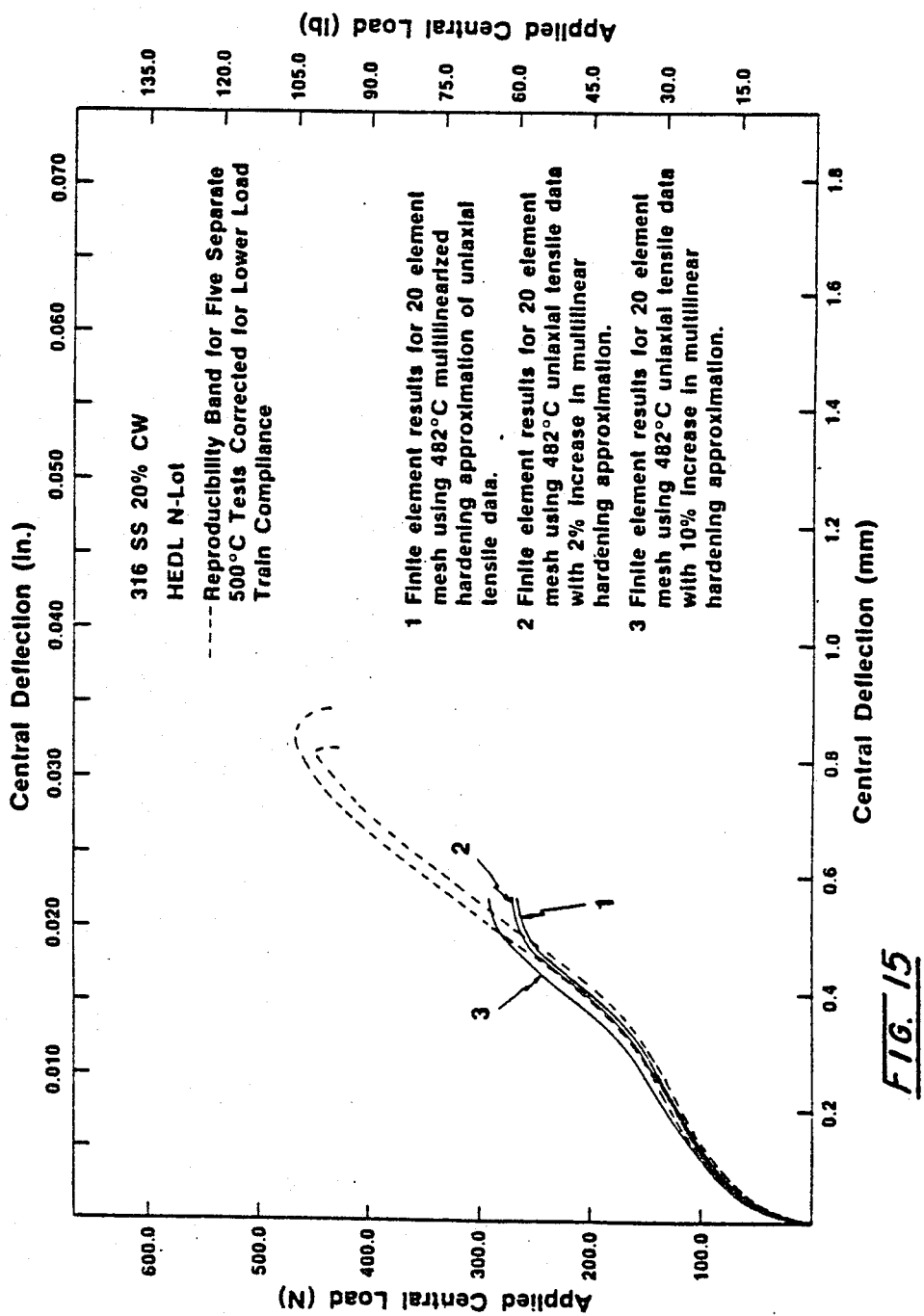

An analysis was performed to gain some understanding of the resolution capability of the MBT methodology as compared to the more conventional approach of uniaxial tensile testing to determine mechanical behavior. The multi-linearized work hardening curve for the N-LOT material at 482° C. shown in FIG. 12 was increased by 2% and 10%, respectively, for a given strain level, as shown in FIG. 14. For ease of discussion, these two cases will be loosely referred to as the 2% flow stress input change and the 10% flow stress input change. The 20 element mesh was used to determine central load and displacement information. The calculated central load/deflection curves are presented in FIG. 15. It is clear from the figure that curves 1 and 2, which are the results for the 0% stress input change and the 2% flow stress input change respectively, fall within the experimental reproducibility band. However, curve 3 in FIG. 15, which represents the 10% flow stress input change lies well above the experimental reproducibility band. Therefore, the stress/strain resolution capability of the MBT methodology lies somewhere between the two cases analyzed.

Figure 16:
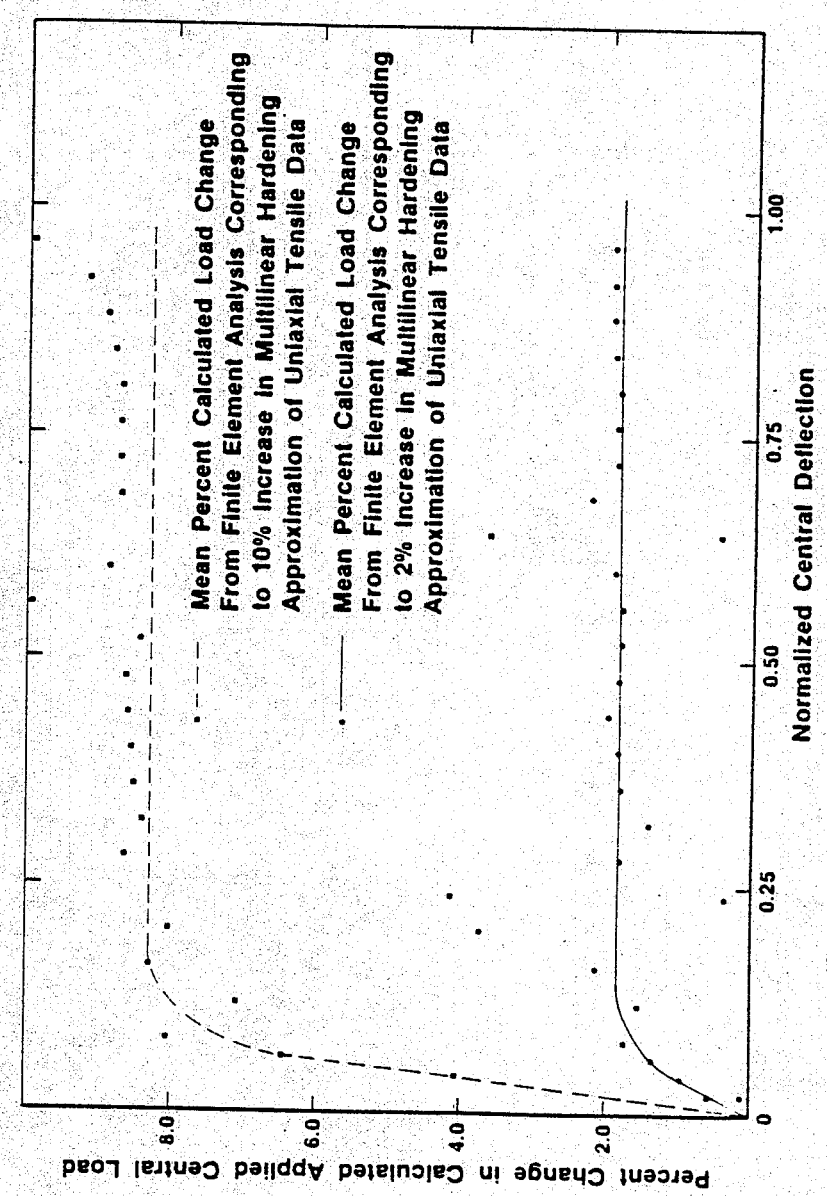

In order to gain a more quantitative understanding of MBT stress/strain determination accuracy, the percent change in calculated applied central load was plotted against the normalized central deflection for the 2% and 10% flow stress input changes as shown in FIG. 16. The reason for the large deviation from the mean percent calculated load shown in FIG. 16 at normalized central deflections of 0.20 and 0.60 are due to the fact that the friction-gap model is discrete and therefore the boundary conditions change significantly as additional nodes come into contact. A 2% change in flow stress input results in a mean percent calculated load change of approximately 1.8. Likewise, a 10% change in flow stress input results in a mean percent calculated load change of approximately 8.3. These results are plotted in FIG. 17. The resulting curve is approximately linear and is observed to lie very close to the unity slope line which obviously indicates good inherent resolution capability for the MBT methodology. This curve can be throught of as an uncertaintly mapping function from uniaxial tensile stress uncertainty space to the resulting MBT applied central load uncertainty space, or vice versa. In particular, reference (21) reported 95% confidence limits for the 0.2% yield stress and UTS of the N-LOT material at 482° C. for 9 separate uniaxial tensile tests on large tube specimens. The 95% confidence limit for the 0.2% yield stress was + or −8.13% of the mean and the 95% confidence limit for the UTS was + or −3.41% of the mean. Using FIG. 17, these 95% confidence limits in stress map into maximum calculated changes in MBT mean applied central loads of + or −6.8% and + or −2.75%, respectively. Conversely, 95% confidence limits for the MBT applied central load were calculated for the N-LOT material at 500° C. using the data shown in FIG. 9. The 95% confidence limit at the point of departure from linearity was found to be + or −6.69% of the mean. This point on the central load/deflection curve corresponds to the 0.2% yield stress. At a central deflection of 0.13 mm, the 95% confidence limit was found to be + or −4.07% of the mean. At a central deflection of 0.64 mm the 95% confidence limit was found to be + or −2.85% of the mean. This point on the central load/deflection curve corresponds to the UTS. Again, using FIG. 17, these confidence limits are found to map into stress uncertainties of + or −7.90%, + or −4.90%, and + or −2.50%, respectively. The confidence limit band width for uniaxial testing of large specimen is primarily determined by material variability and experimental errors such as those introduced in specimen machining, gripping extensions, column alignment which can result in bending and transducer accuracy. The confidence limit width for the MBT is primarily determined by material variability and experimental errors such as those introduced in specimen machining, friction coefficient variation, punch/die/specimen alignment, and transducer accuracy.

Figure 17:
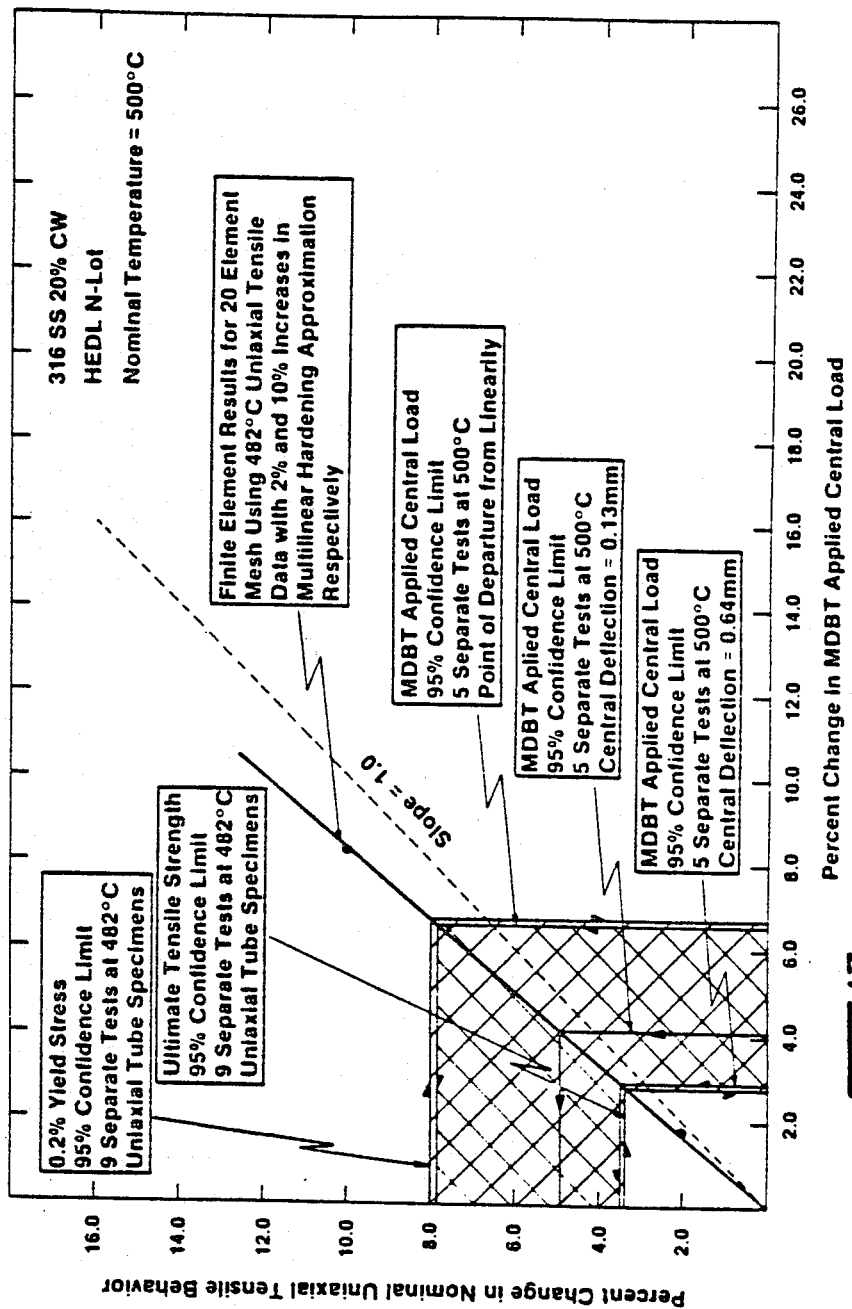

In summary, FIG. 17 indicates that the MBT methodology is capable of delivering uniaxial work hardening information with approximately the same level of accuracy as that present in the more conventional large specimen uniaxial tensile testing approach.

The basic data inversion strategy for the near term is as follows:

1. Assume several flow curves that bracket the flow curve of the material being investigated.

2. Implement the finite element code and generate central load/deflection curves for the various flow curves of step 1.

3. Compare finite element results with experimental data. Repeat steps 1 and 2 until a calculated central load/deflection curve falls within the experimental reproducibility band.

This is a near term strategy because in time the finite element data base will become sufficiently large, for a standardized specimen and loading geometry, that no further finite element runs will be necessary. Therefore, an alternative fourth step would be:

4. Interpolation of calculated load/deflection curves for a measured load/deflection curve to determine the stress/strain curve of the material being tested.

In order to implement this basic data inversion strategy effectively, a convenient method of parameterization of the flow curves is desired. In particular, the flow curves of many materials from initial yield to the end of the region of uniform plastic deformation, and often beyond, can be approximiated by a power law relation as follows:

$$\sigma = K\epsilon^n$$

where
n = strain-hardening exponent
K = strength coefficient

The strength coefficient can be written in terms of the uniform stress and strain as follows:

$$K = n^n/\sigma_{uts}$$

where
$\sigma_{uts}$ = true ultimate tensile strength

Figure 20:
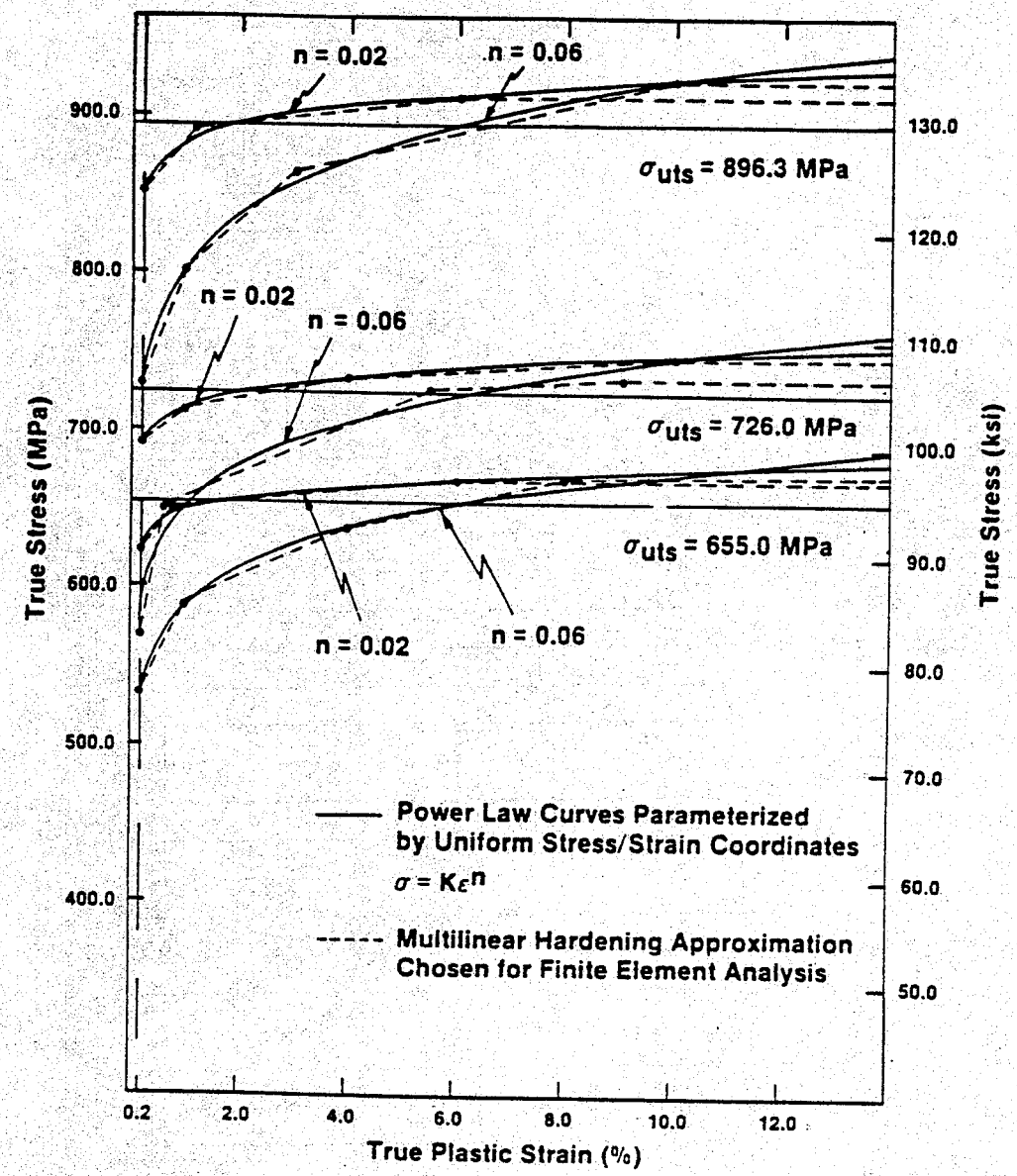

Therefore, the entire flow curve can be parameterized by the true ultimate tensile strength and the true uniform strain. The yield stress is defined by cutting off the flow curve at 0.2% strain as illustrated in FIG. 20.

The material elastic stiffness is characterized by Young's modulus which is primarily determined by atomic binding forces. The elastic modulus is, therefore, quite structure insensitive because the atomic binding forces cannot be significantly altered without modifying the basic nature of the material. Therefore, the Young's modulus can be determined to sufficient accuracy by testing a uniaxial specimen at temperature in the unirradiated condition. If a uniaxial test cannot be done, it is trivial to run an elastic finite element solution to determine Young's modulus. A pre-irradiation uniaxial test at temperature is advisable since the stress/strain curve generated, in general, provides a lower bound to the post-irradiation mechanical behavior.

To recapitulate, in the present invention the mechanical behavior determining typically comprises:

e. computing the load/deflection function corresponding to at least one trial stress/strain function, and f. comparing the computed load/deflection function with the measured load/deflection function.

The mechanical behavior determining typically comprises also:

g. repeating steps e and f for new trial stress/strain functions until a trial stress/strain function provides a computed load/deflection function that differs from the measured load/deflection function in the opposite direction from that of another computed load/deflection function, h. repeating steps e and f for a trial stress/strain function interpolated between the trial stress/strain functions for which the computed load/deflection functions differ the least from the measured load/deflection function and in opposite directions therefrom, and i. repeating step h until a stress strain function is determined for which the computed load/deflection function is within a selected range of tolerance from the measured load/deflection function.

Alternatively, (instead of by the above steps h and i), the steps e, f, and g may be followed by:

j. determining the stress/strain function for the measured load/deflection function by interpolation between the trial stress/strain functions for which the computed load/deflection functions differ the least from the measured load/deflection function and in opposite directions therefrom. The interpolation typically is carried out point by point and/or with an empirically determined algorithm.

Either way the computing step e typically is carried out using the ABAQUS finite element computer code and the finite element friction-gap boundary condition model subroutine. Other appropriate finite element computer codes capable of modelling the relevant material, constitutive, and boundary conditions may also be used.

In general, the most effective strategy is to use trial stress/strain functions that are expressible as mathematical relations. In this way, the shape of the trial stress/strain functions can be limited to a narrow class of shapes. The analyst must, of necessity, take care in his choice of mathematical representation to ensure that the material being tested actually performs in accordance with the choice of the shape function. Where the trial stress/strain functions are expressible as power law relations, each power law relation typically has the general form $$\sigma = K\epsilon^n,$$

wherein the terms are as defined above.

Where convenient and appropriate, the trial stress/strain functions may be expressed as a power series, typically having the general form $$\sigma = a_0 + a_1\epsilon + a_2\epsilon^2 + \cdots + a_n\epsilon^n,$$

where each $a_i$ is a constant.

Typically, the trial stress/strain function in step e is related to known behavior of the material or of a material having similar relevant characteristics. Where the matrial is an alloy, the known behavior typically is that of another alloy having the same base. Where the material has been irradiated, the known behavior typically is that of similar material that has not been irradiated or of a similar material that has been irradiated.

A variety of materials in the post-irradiated condition were tested for irradiation experiments carried out in the High Flux Isotope Reactor (HFIR) at Oak Ridge National Laboratory (ORNL). The calculated irradiation parameters are listed in Table II. ORNL has reported a potential error in the in-core temperatures for the CRT-32 experiment. Direct temperature measurements are not currently possible since HFIR was not initially designed for instrumented experiments. The temperatures reported were based on gamma-heating calculations. The gamma-heating rates in HFIR are quite high and the temperature gradients are rather steep. As a result, the temperatures reported previously by ORNL for HFIR may be about 50°–75° C. too high. However, the specimens were tested at the originally reported irradiation temperatures.

TABLE II

HFIR CTR-32 Calculated Irradiation Parameters

| In-Core Position | Temp. (°C.) | Fast Fluence (0.1 mev neutrons/m$^2$) | Thermal Fluence (neutrons/m$^2$) | Total Fluence (neutrons/m$^2$) | dpa (316 SS) | (12.4% ni) (at. ppm) |
|---|---|---|---|---|---|---|
| 4 | 600 | 1.1 × 10$^{26}$ | 2.1 × 10$^{26}$ | 4.4 × 10$^{26}$ | 8.5 | 360 |

TABLE II-continued

| | | HFIR CTR-32 Calculated Irradiation Parameters | | | | |
|---|---|---|---|---|---|---|
| In-Core Position | Temp. (°C.) | Fast Fluence (0.1 mev neutrons/m²) | Thermal Fluence (neutrons/m²) | Total Fluence (neutrons/m²) | dpa (316 SS) | (12.4% ni) (at. ppm) |
| 9 | 500 | $1.1 \times 10^{26}$ | $2.1 \times 10^{26}$ | $4.4 \times 10^{26}$ | 8.5 | 360 |

Figure 18:
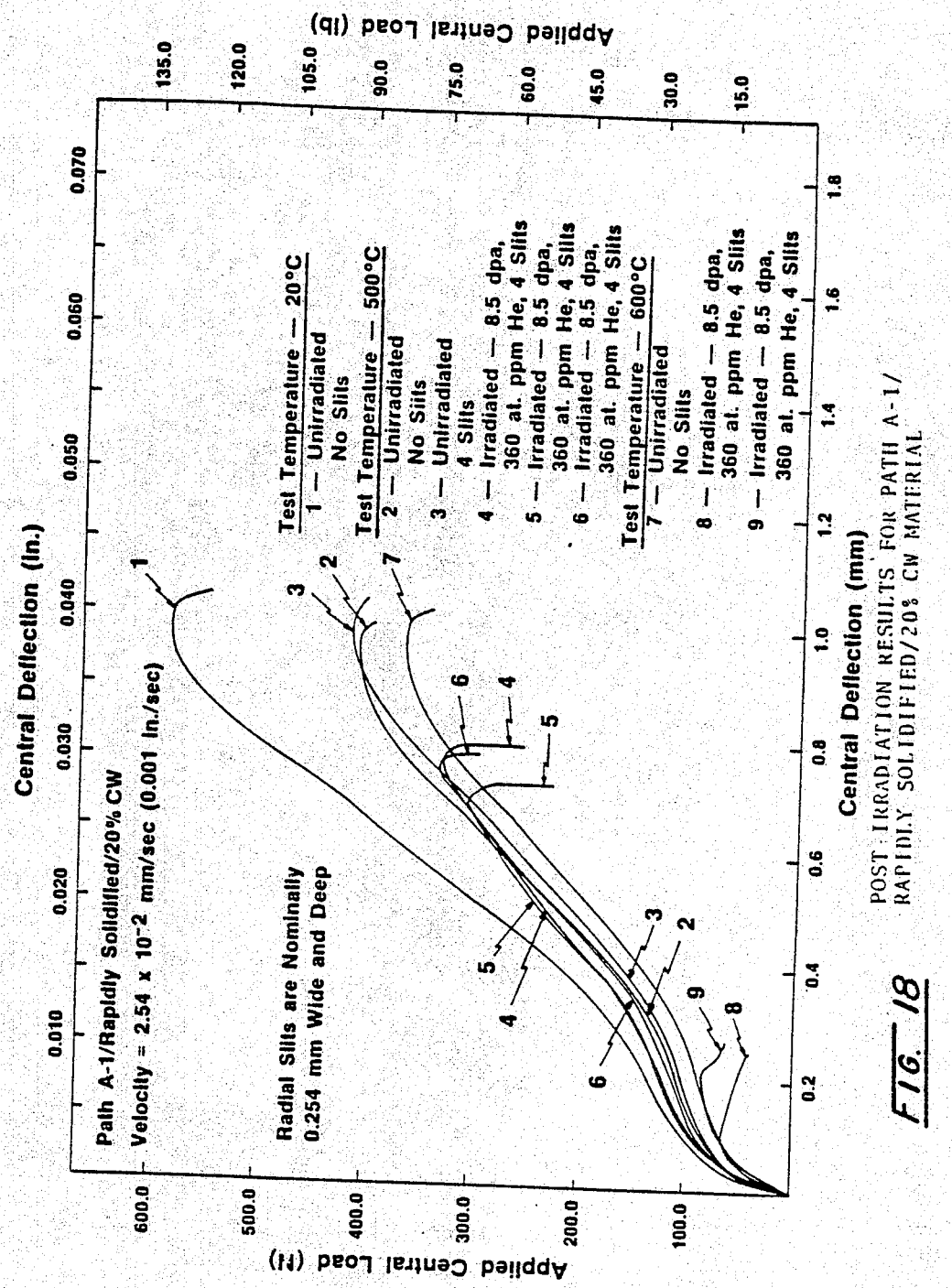
Figure 19:
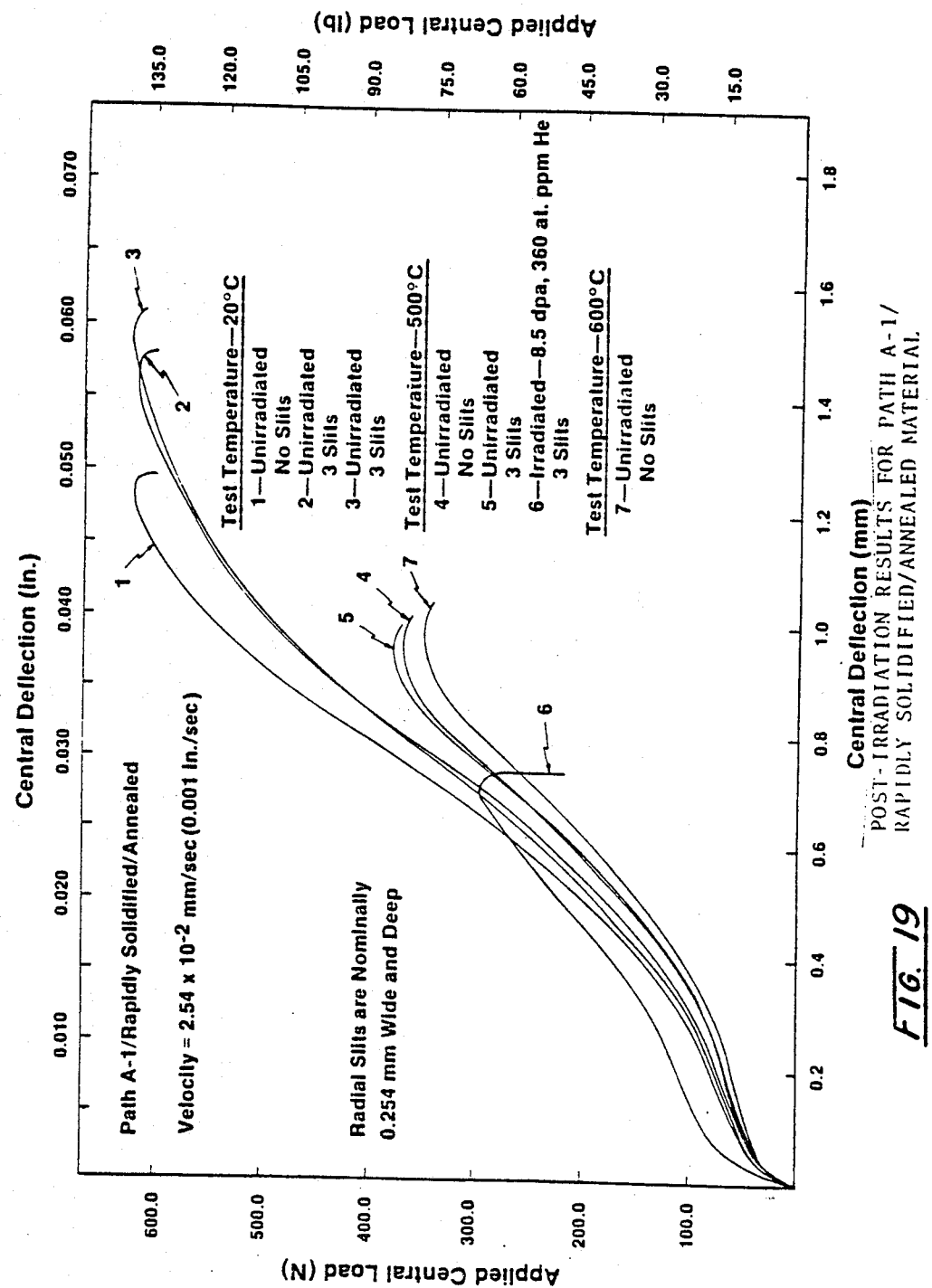

The pre- and post-irradiation results for the Path A-1 rapidly solidified material is shown in FIGS. 18 and 19. The Path A-1 material is identical to primary candidate alloy of the national fusion alloy development program which consists of titanium modification of nuclear grade 316 SS.

Radial slitting can produce significant errors in the central load/deflection response. Therefore, pre-irradiation tests on slitted specimens were performed for comparison. Examination of FIGS. 18 and 19 indicates that for the materials tested the slits can produce significant effects on the central load/deflection response at room temperature as expected. However, the effects are not as dramatic at elevated temperatures where the material flows more readily. Therefore, although not exact, the elevated temperature data for the post-irradiated samples is fairly close to the response obtained for samples without radial slits.

Figure 21:
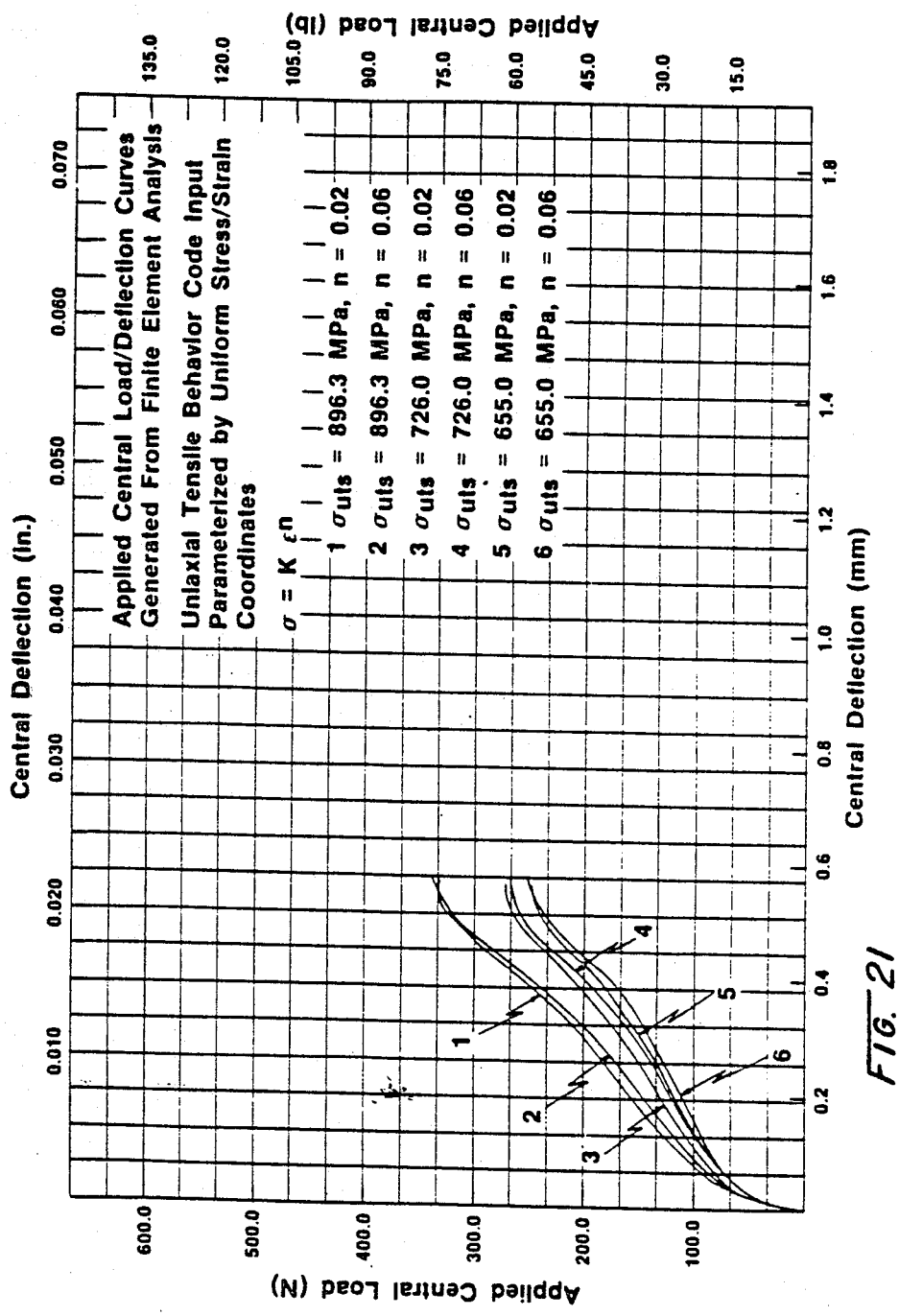
Figure 22:
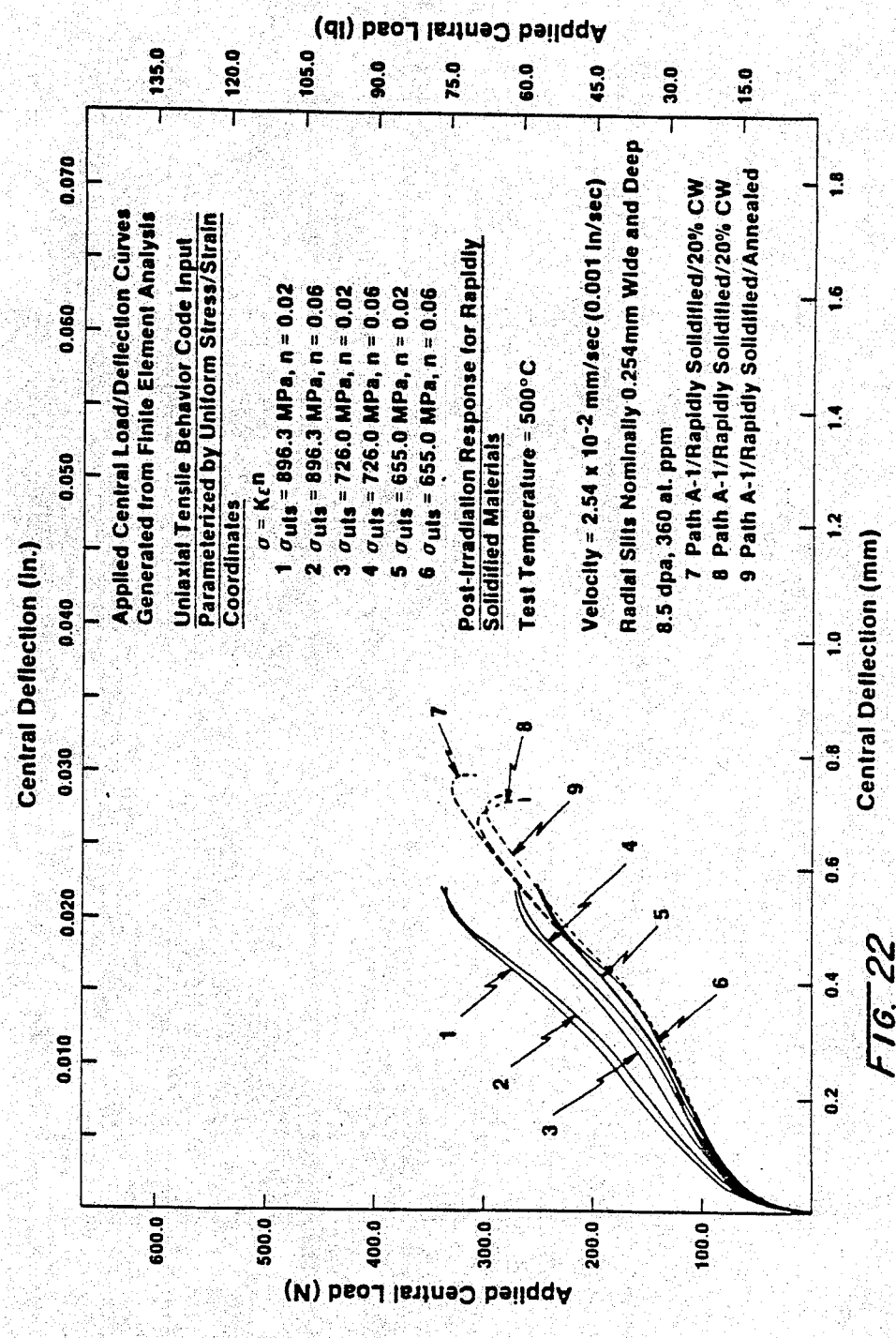

The parameterized spectrum of flow curves analyzed are shown in FIG. 20. The resulting central load/deflection curves generated using the various flow curves are presented in FIG. 21 and Table III. FIG. 21 is repeated in FIG. 22 with the post-irradiation Path A-1/RS experimental curves superimposed. The Path A-1/RS/20% CW experimental data is best matched by curve 5 in FIG. 22 and the Path A-1/RS/Annealed experimental data is best matched by curve 6 in FIG. 22. However, these results are only approximate because of inherent experimental inaccuracies (such as specimen slitting) present in the experimental data for this group of post-irradiated specimens.

Figure 23:
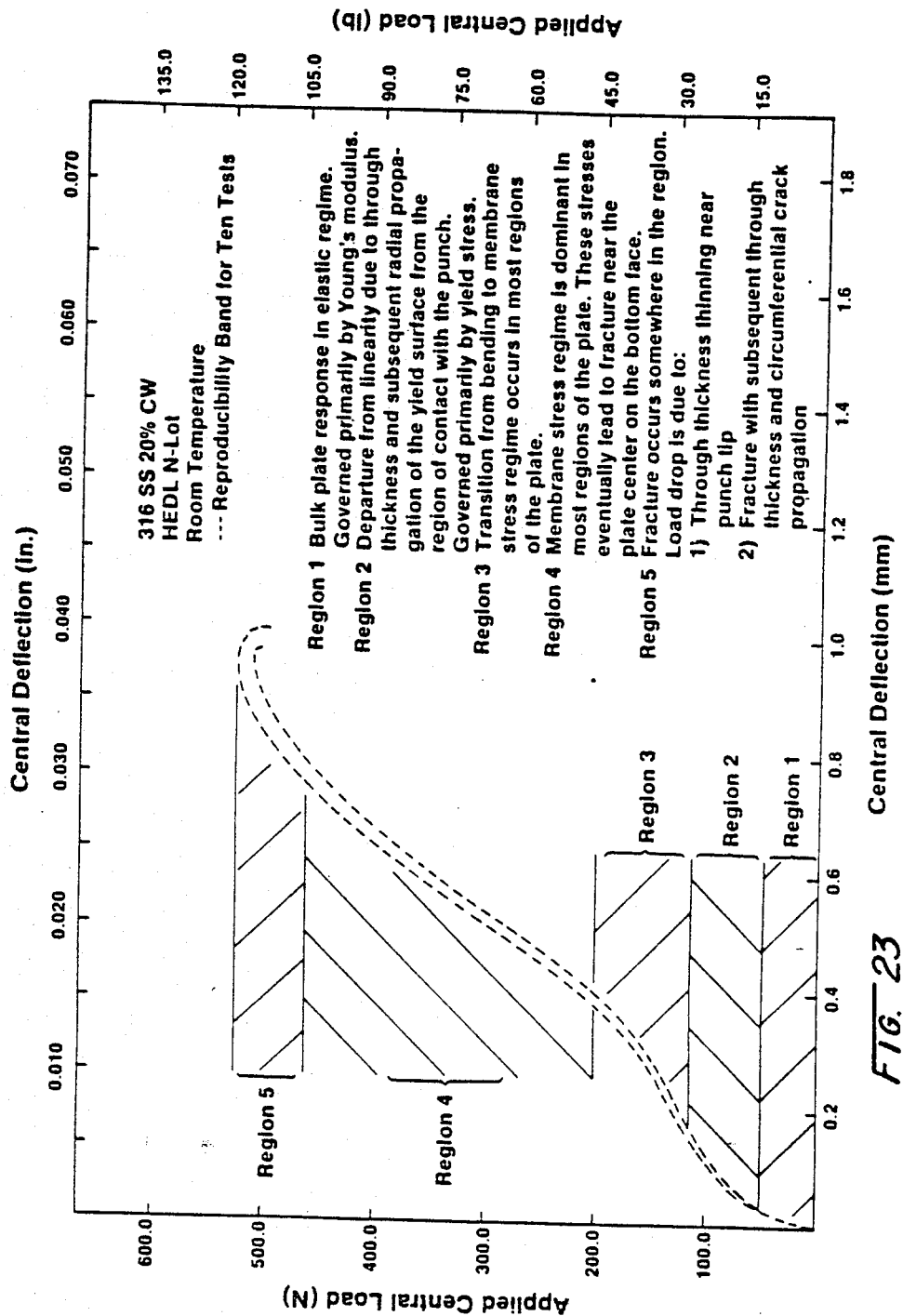

Analyses were performed to provide a fundamental interpretation of the applied central load/deflection curves. As illustrated in FIG. 23, the central load deflection curve can be divided into five distinct regions each of which is primarily governed by widely differing modes of deformation and phenomena.

Examination of the strain contours such as those in FIG. 11 reveals that the plate yields upon contact with the punch in a localized region near the punch tip. However, over the initial linear portion of the load/deflection curve, which spans the first 0.0381 mm of deflection, the bulk of the plate response is in the elastic regime. This has been verified in the finite element analyses and also experimentally by loading and unloading several times up to the point of departure from linearity. During these experiments, the linear portion of the curve was retraced until bulk plate yielding occurred at the point of departure from linearity. Also, a small plastic indentation at the center of the plate where the punch made contact was observed for all loading in the bulk plate elastic range.

During the deformation in Region 1, the yield surface in the plate propagates through the thickness from the punch contact zone and radially outward over a cylindrical plate region of approximately 0.18 mm in diameter. The Region 2 departure from linearity is due to continued propagation of the yield surface in the plate

TABLE III

Twenty Element Mesh Finite Element Prediction of Central Load/Deflection Response from Parameterized Uniaxial Flow Curves

| | Central Load (N) | | | | | |
|---|---|---|---|---|---|---|
| | $\sigma_{uts} = 655.0$ MPa | | $\sigma_{uts} = 726.0$ MPa | | $\sigma_{uts} = 896.3$ MPa | |
| Central Deflection (mm) | n = 0.02 | n = 0.06 | n = 0.02 | n = 0.06 | n = 0.02 | n = 0.06 |
| 0.0127 | 19.06 | 18.93 | 19.24 | 18.90 | 19.51 | 19.34 |
| 0.0254 | 47.46 | 44.46 | 49.42 | 46.88 | 53.02 | 51.15 |
| 0.0381 | 56.40 | 52.66 | 60.63 | 57.16 | 70.68 | 66.28 |
| 0.0508 | 56.40 | 54.71 | 62.49 | 59.87 | 75.66 | 72.19 |
| 0.0762 | 79.22 | 74.10 | 85.85 | 79.71 | 99.72 | 92.96 |
| 0.1016 | 81.98 | 78.15 | 89.72 | 85.00 | 108.53 | 102.93 |
| 0.1270 | 83.00 | 80.02 | 90.43 | 86.02 | 108.93 | 106.13 |
| 0.1524 | 104.31 | 95.01 | 113.07 | 103.86 | 131.66 | 116.18 |
| 0.1178 | 109.47 | 101.24 | 123.08 | 111.87 | 144.87 | 136.02 |
| 0.2032 | 118.05 | 112.27 | 130.86 | 128.50 | 160.35 | 152.66 |
| 0.2286 | 121.43 | 117.16 | 134.33 | 130.99 | 164.66 | 158.17 |
| 0.2540 | 123.34 | 121.34 | 139.76 | 139.00 | 169.25 | 163.82 |
| 0.2794 | 145.18 | 135.09 | 158.22 | 146.07 | 192.11 | 173.56 |
| 0.3048 | 149.36 | 143.67 | 169.78 | 161.28 | 204.52 | 196.51 |
| 0.3302 | 157.15 | 150.52 | 174.01 | 169.02 | 213.33 | 205.10 |
| 0.3556 | 159.91 | 160.80 | 181.97 | 178.68 | 223.73 | 217.60 |
| 0.3810 | 169.96 | 169.16 | 188.91 | 186.64 | 233.08 | 227.92 |
| 0.4064 | 190.24 | 176.72 | 200.52 | 205.76 | 256.87 | 239.12 |
| 0.4318 | 206.52 | 201.67 | 228.67 | 224.09 | 280.45 | 282.36 |
| 0.4572 | 217.82 | 214.48 | 244.11 | 237.70 | 295.61 | 290.45 |
| 0.4826 | 227.20 | 225.11 | 252.25 | 249.49 | 308.56 | 305.27 |
| 0.5080 | 240.90 | 238.19 | 267.01 | 261.72 | 324.79 | 322.30 |
| 0.5344 | 241.44 | 242.37 | 269.06 | 267.77 | 330.75 | 330.04 |
| 0.5588 | 244.20 | 244.11 | 272.13 | 270.79 | 332.18 | 333.38 |
| 0.5842 | 271.64 | 271.19 | 302.33 | 313.67 | 371.19 | 372.70 |
| 0.6096 | 281.91 | 290.59 | 312.29 | 331.11 | 380.53 | 392.18 |
| 0.6350 | 250.20 | 282.51 | 292.86 | 320.97 | 372.37 | 373.72 | radially outward but over much larger portions of the plate. In essence, the bulk of the plate is yielding and thus Region 2 is governed primarily by the yield stress of the material.

Figure 24:
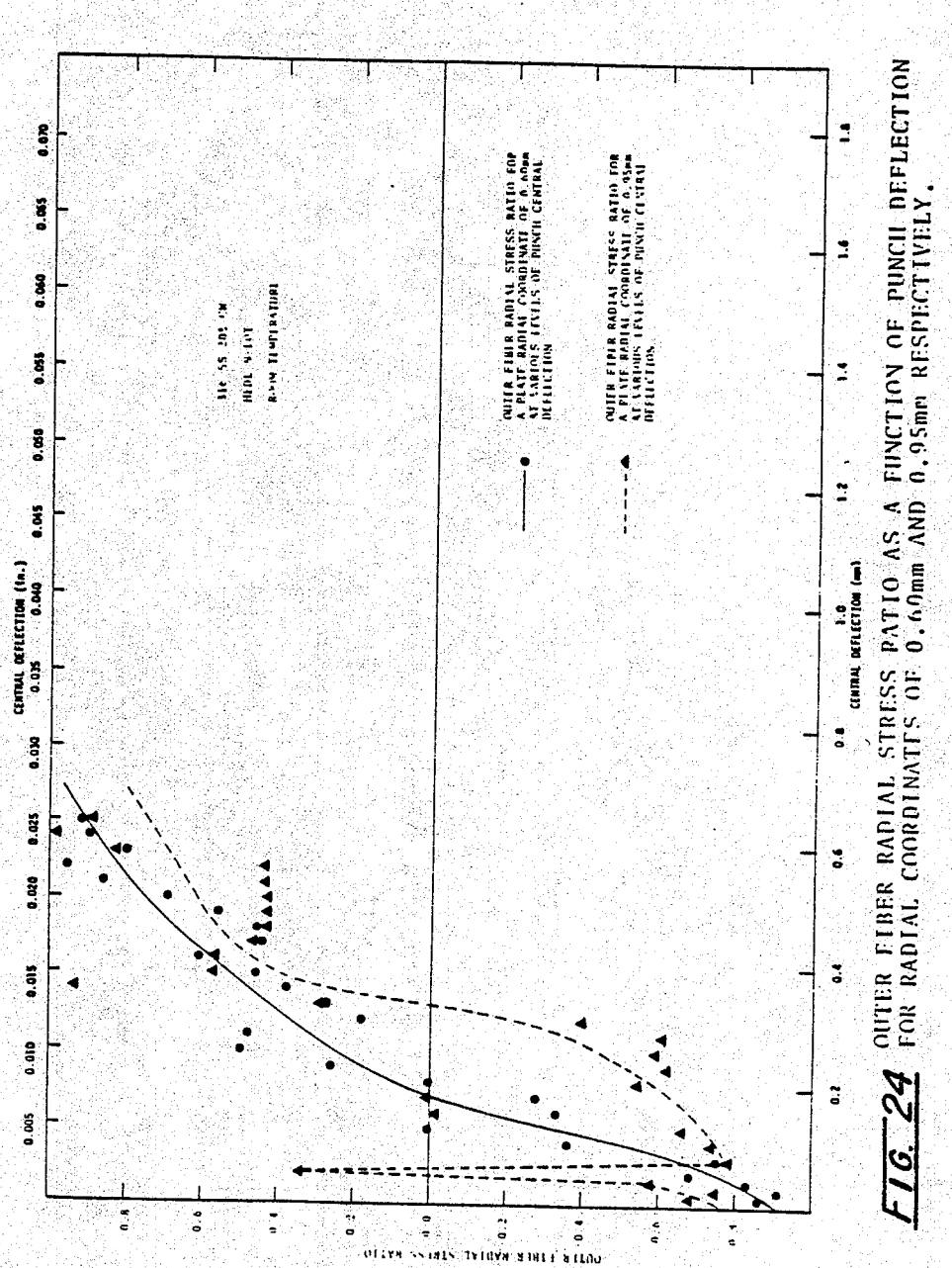

The ratio of the outermost fiber radial stress components on the plate top and bottom surfaces for two radial locations as a function of the punch central deflection was plotted to assess the range of central deflections over which the transition from bending to membrane stretching regime occurs. As shown in FIG. 24, the transition occurs for central deflections between approximately 0.18 mm and 0.38 mm. Thus Region 3 illustrates the portion of the central load/deflection curve where the transition from bending to membrane stretching regime occurs in most regions of the plate. In Region 4, the membrane stretching regime is dominant in most regions of the plate. These stresses eventually lead to fracture in Region 5 on the bottom of the plate at a radial location of approximately 0.254 mm.

Figure 25:
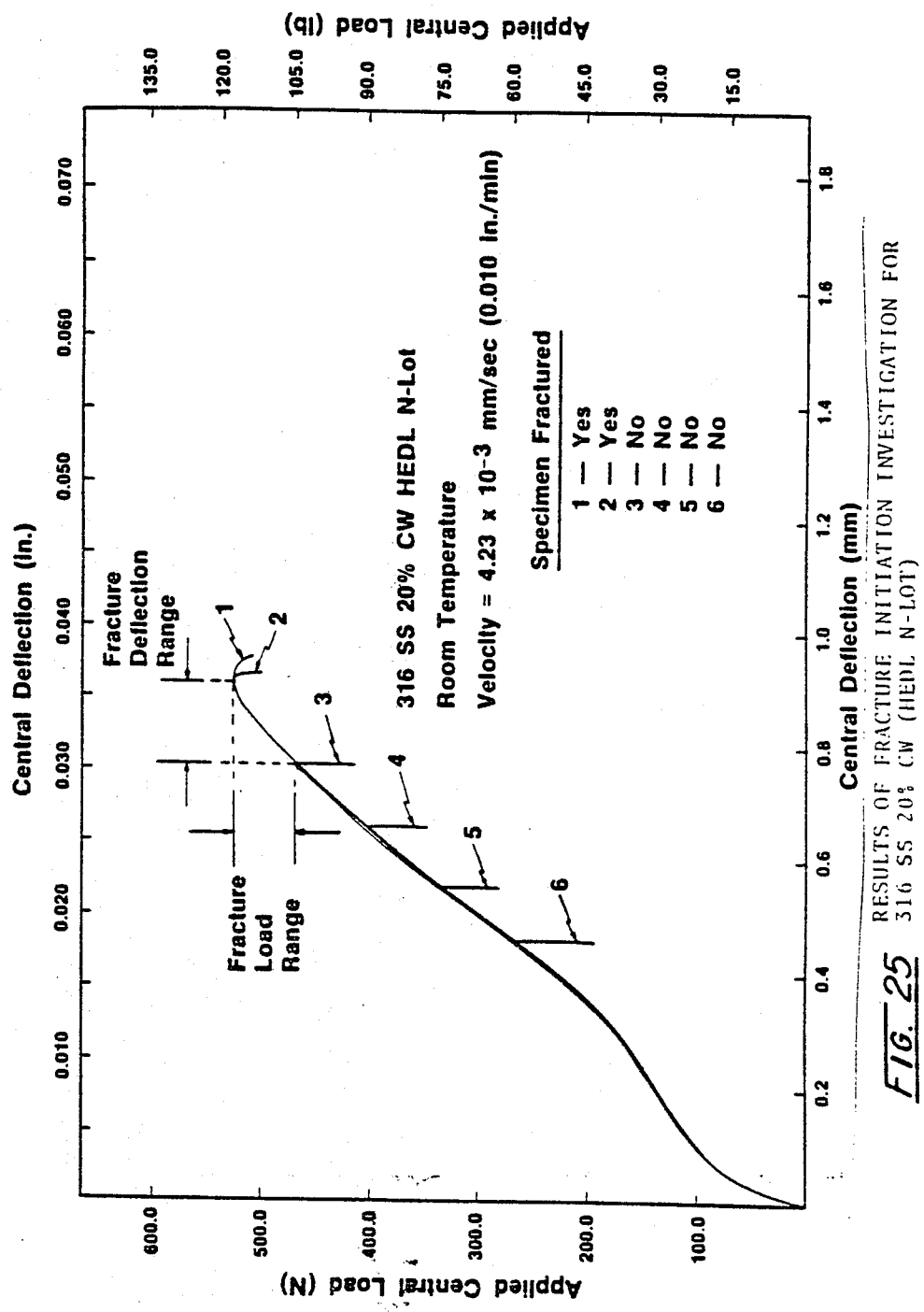
Figure 34:
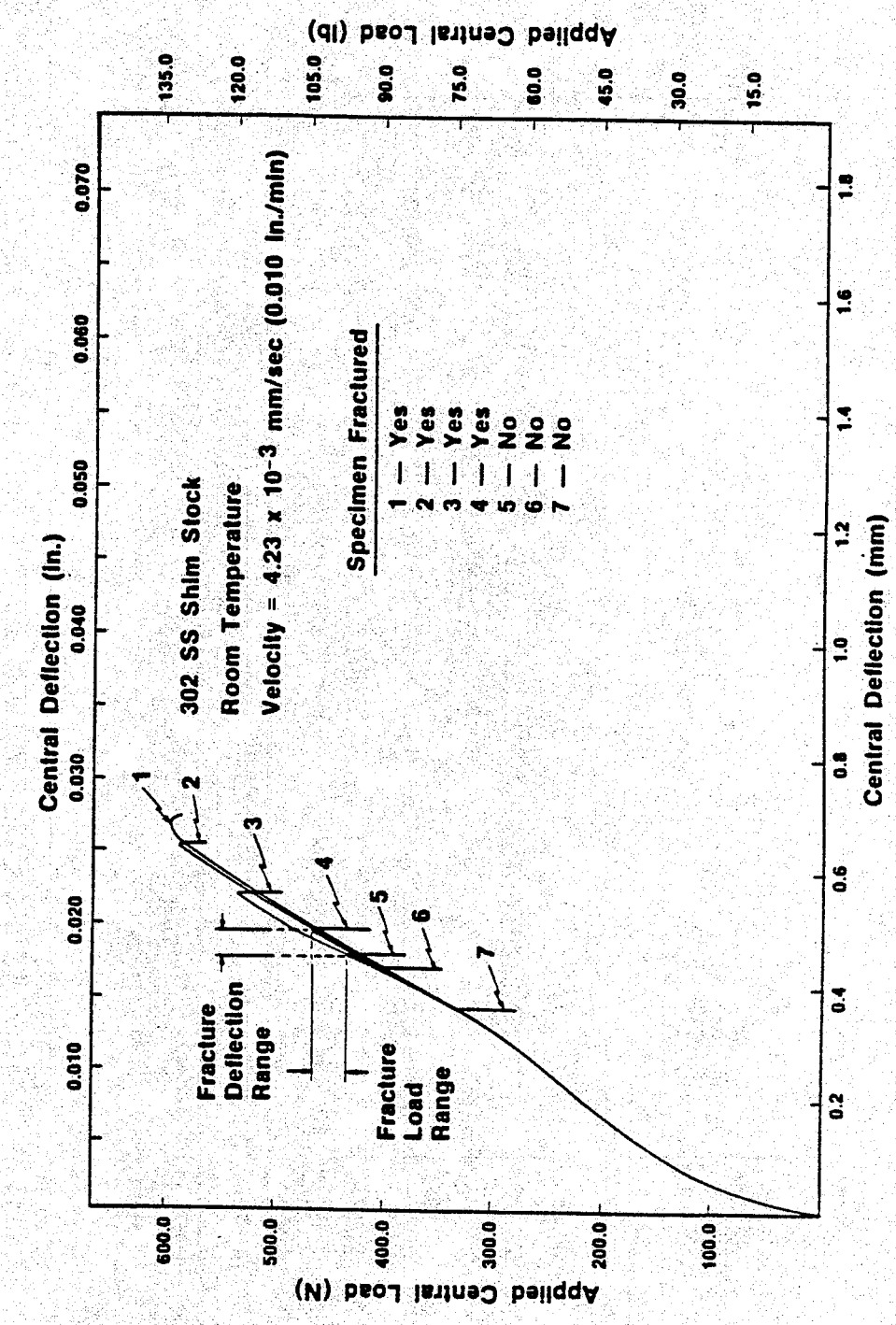
FIG. 34 shows the results of the fracture initiation investigation for 302 SS shim stock.

An investigation to determine approximately where on the central load/deflection curve fracture initiates for 302 SS and 316 SS HEDL N-LOT is shown in FIGS. 25 and 34, respectively. For both materials, the fracture initiates prior to the load peak. Fracture has been observed to occur at a radial location of approximately 0.254 mm for the 302 ss shim stock specimens. The fracture load range for the N-Lot material occurs somewhat closer to the load peak in comparison with the 302 SS shim stock data because of the larger ductility of the N-LOT material.

The load drop in the MBT is actually due to two causes. The first is through thickness reduction of the plate near the punch which decreases the load carrying capacity. The second is fracture with subsequent through thickness and circumferential crack propagation.

A new finite element friction-gap boundary condition model according to the present invention is applicable to a wide variety of non-linear boundary value problems. In particular, this model is essential in the analysis of the MBT data for the conversion of the experimentally determined central load/deflection curves to stress/strain information. Unlike uniaxial tensile testing where the strain distribution is fairly uniform across the specimen gage section prior to necking for a given axial deflection, the MBT specimens experience large strain gradients which are heavily dependent on the punch and die geometry and friction coefficient.

The derivation of the equations will be presented in the context of the MBT experiment, but the theory is of general applicability. In order to accurately analyze this highly non-linear boundary value problem with shifting contacts, a model to reproduce the frictional contact has been developed for the support and a similar model with the additional boundary condition of punch velocity has also been developed.

Figure 26:
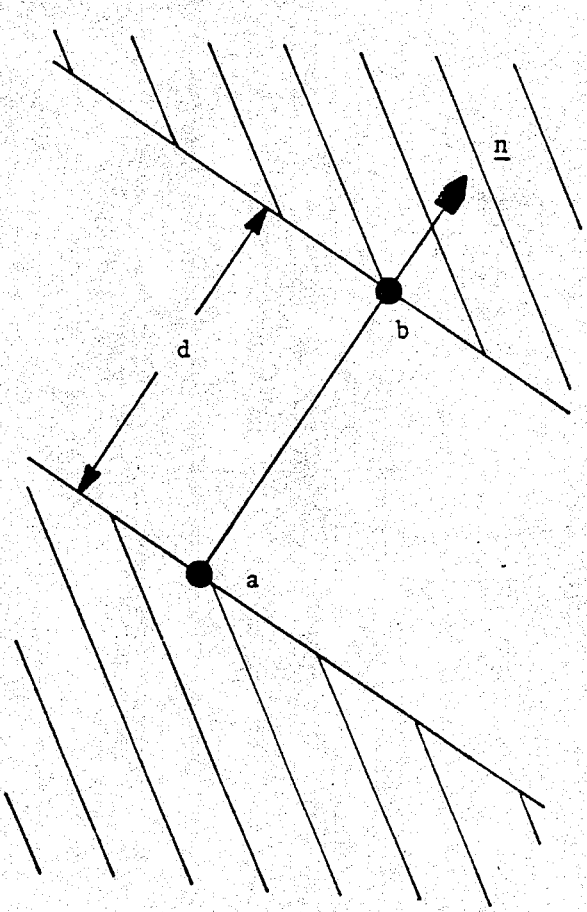
FIG. 26 is a schematic representation of the ABAQUS code unidirectional gap geometry for two body dual node friction model.

The ABAQUS code contains a two body dual node friction model with a gap option. This simple model can handle problems such as a box sliding down on an inclined plane, for example. In this model with gap option, the code monitors the relative displacement of the two gap nodes, as depicted in FIG. 26. The relative displacement is defined as:

$$u_r = (u_a - u_b) \cdot n$$

where
$u_r$ = relative displacement
$u_a$ = node a displacement vector
$u_b$ = node b displacement vector
n = direction cosines of vector from node a to node b When the relative displacement attempts to exceed the closure distance d, the gap is closed and the friction constraint is imposed. Obviously, opening or closing the gap results in a non-linear analysis, and iteration is needed to determine if friction node pairs are in contact. Thus, the code monitors the force when in contact or the relative displacement when not in contact.

The code uses classical Coulomb friction with a stiffness in stick (SIS) method to aid convergence. The SIS is the elastic stiffness which will transmit shear forces across the element when these forces are below the friction limit. The SIS value is defined as:

$$SIS = \mu N / \delta$$

where
$\mu$ = coefficient of friction
N = expected normal force
$\delta$ = relative displacement allowed before slip occurs The SIS value should be as small as is reasonable to optimize convergence.

Figure 27:
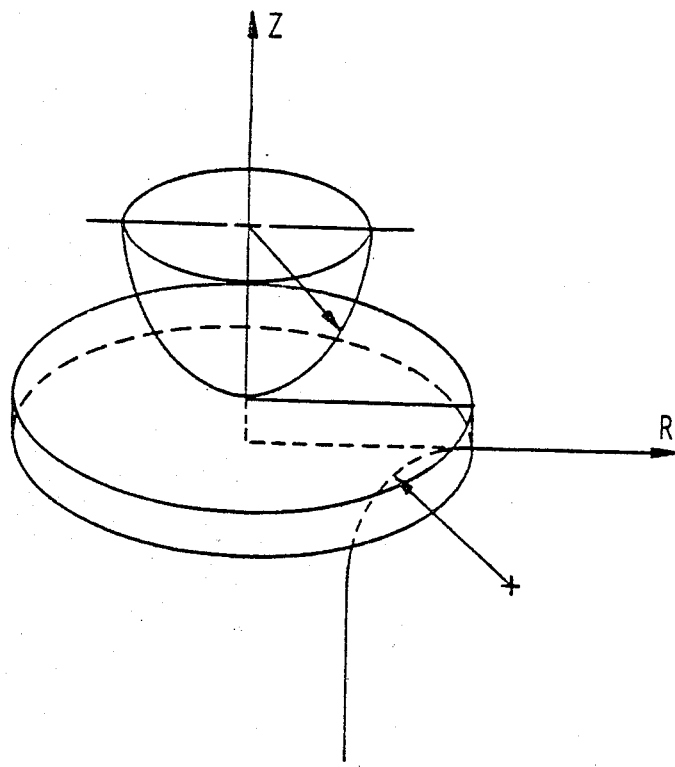
FIG. 27 is a schematic representation of the miniaturized disk bend test boundary value problem. The three dimensional problem is idealized as two dimensional axisymetric problem.

In the MBT it is readily possible to align the punch, die, and specimen to within 0.02 mm and thus obtain good experimental reproducibility. Therefore, the computing time can be greatly reduced by taking advantage of axisymetry. As shown schematically in FIGS. 27 and 28, the plate response is calculated in cylindrical coordinates, whereas, the friction model operates in a Cartesian system. This difficulty is circumvented by introduction of the shadow node concept. This concept is implemented by introducing two ficticious shadow nodes somewhere in cartesian space for each physical potential friction node in cylindrical space. In this fashion, the friction-gap problem is effectively mapped from two dimensional cylindrical space to two dimensional Cartesian space where the code can model two body dual node friction.

Figure 28:
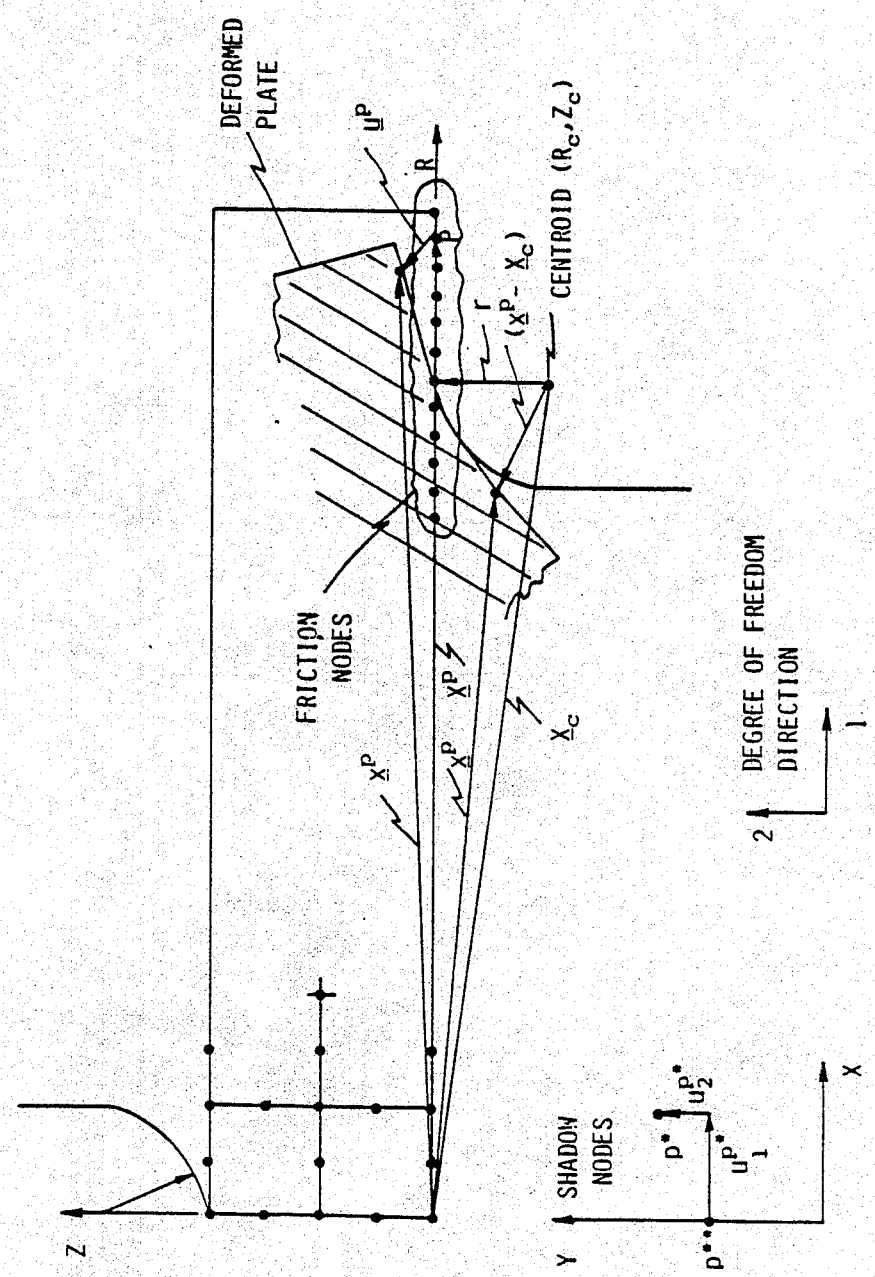
FIG. 28 is a friction-gap boundary condition model schematic for the miniaturized disk bend test support. The potential physical friction nodes in two dimensional cylindrical space are modelled using shadow node pairs in two dimensional Cartesian space.

FIG. 28 illustrates the shadow node mapping schematically for the support. Potential physical friction nodes, such as the p node in FIG. 28, are identified at the start of the analysis. The p* and p nodes are associated with the p node. The p shadow node is fixed and models the support while the p* node displaces subject to proper kinematics as the p node is displaced. Therefore, it is necessary to write multi-point constraint equations to eliminate the degrees of freedom (dof) associated with node p* in favor of the dof of the physical node p.

In this modeling application, the punch and the support were taken to be infinitely rigid. Since the MBT has been principally designed to test metallic materials at elevated temperature, this is a reasonable assumption. However, equations can be written to relax this assumption.

There are no kinematic assumptions on the boundary condition model other than the fact that a plate node cannot penetrate the punch or support region. There are also no interfacial elements necessary and therefore the method can be termed a direct boundary condition model since it operates directly on the plate. Referring to FIG. 28 once again, it is obvious that constraint equations are necessary to eliminate the dof associated with the p* node in favor of the dof of the physical mode p, and then to constrain the p* displacements in such a way that the physical node p cannot enter the support region. The relative displacement of the p* and p** nodes from the yz plane will then be monitored during each iteration of a time step. If this relative displacement attempts to exceed the initial separation distance of node p from the support, then the constraint is imposed and friction implemented. It is necessary to monitor the slip distance. This is done by letting $u^{p*}_2$ be the projected lateral displacement of the physical mode p onto the support surface directed radially through the support centroid. The support centroid is defined as the point in the support where the radius of curvature initiates. A similar definition applies to the punch centroid. It is important to realize that this shadow node mapping concept is compatible with the ABAQUS code because essentially all the friction information is contained in the normal forces (which the code calculates in cylindrical geometry), and by utilizing multi-point constraints, the code correctly applies the normal force component in cartesian space. In summary, at each iteration of a static time step, all possible physical friction node multi-point constraint equations are applied, each pair of shadow nodes are quizzed to see if contact has been made, and if so the support constraint is imposed and friction invoked. If contact is not made, the code continues to monitor the separation distance of the p* and p** nodes.

In essence, then, utilizing the above stated theory, the friction-gap model for the MBT support reduces to writing a subroutine to eliminate the mobile shadow node dof in favor of the physical node dof. The constraint function can, in general, be of the form:

$$f(u_1, u_2, \ldots, u_n, \text{geometry}) = 0$$

Each call to the subroutine eliminates one degree of freedom. In order to impose the constraint equation the following information must be calculated in the subroutine:

1. A list of dof directions for each dof in the constraint equation.
2. The array of derivatives of the constraint function $$\partial f/\partial u_1, \ldots, \partial f/\partial u_n$$

to eliminate the dof and redistribute the loads
3. The constraint function

Figure 29:
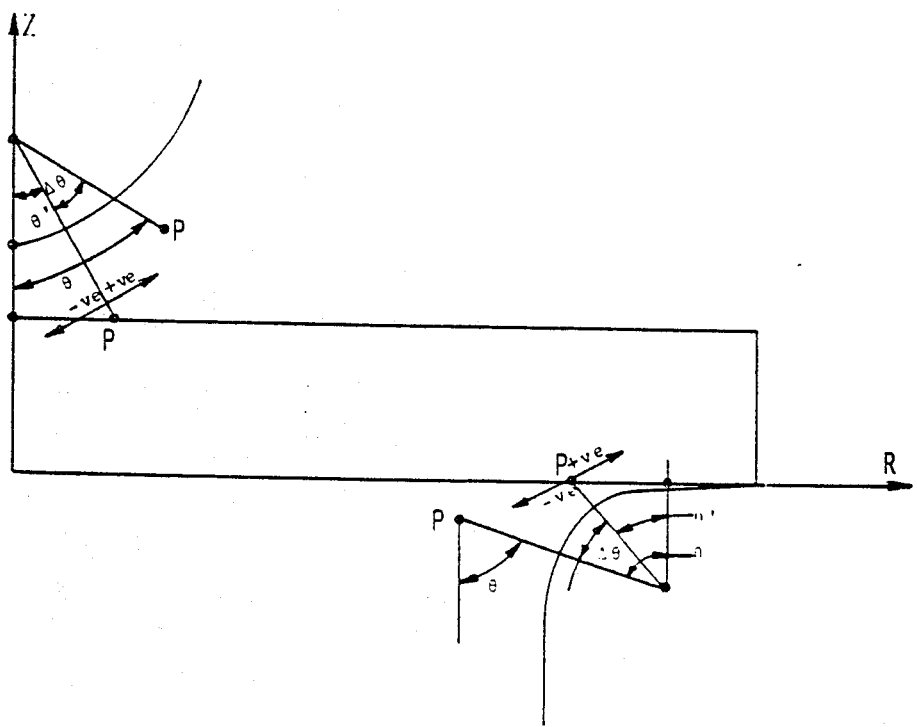
FIG. 29 is a schematic illustration of the sign convention and angle definitions used in the multi-point constraint equation derivations.

The following information is available in the code for use in the subroutine calculation and therefore all equations must be cast in a form that utilizes this information:
1. N—number of dof in the constraint function
2. JTYPE—user defined equation type flag
3. X(6,N)—array of original coordinates of the nodes in the constraint function
4. U(6,N)—array of total displacement at the nodes involved in the constraint function In the derivation of the constraint equations, two cases must be considered:

Case A—the physical node is originally located to the right of the centroid
Case B—the physical node is originally located to the left of the centroid
Each of these cases reduces to two subcases;
Subcase I—the final location of the physical node is to the right of the centroid
Subcase II—the final location of the physical node is to the left of the centroid
The notation used in the derivation of the constraint equations is as follows:
subscripts—dof direction
superscripts—node identification
X—original nodal coordinate vector
X—current nodal coordinate vector
u—total nodal displacement vector
r—support radius of curvature
$R^c$—centroid radial coordinate
$Z^c$—centroid axial coordinate
$e$—$1.0 \times 10^{-6}$ The sign convention and angle definitions used in the equation derivations are shown in FIG. 29. Referring to this figure as well as FIG. 28, the following vector and angle relationships are apparent:

$d^o \equiv$ initial separation distance $= |\underline{X}^c - \underline{X}^p| - r$ $d \equiv$ current separation distance $= |\underline{X}^c - \underline{x}^p| - r$ $$\tan \theta = \frac{R^c - x_r^p}{r - x_z^p}$$

$$\tan \theta' = \frac{R^c - X_r^p}{r}$$

Using the above stated notation and definitions, the following multi-point constraint equations for the support were derived:

<u>Case A $X_r^p \geq R^c$</u>

$x_r^p \equiv X_r^p + u_1^p \geq R^c$      Subcase I $u_1^{p*} = u_2^p - e$ $u_2^{p*} = u_1^p$ $x_r^p \equiv X_r^p + u_1^p < R^c$      Subcase II $u_1^{p*} = \sqrt{(R^c - X_r^p - u_1^p)^2 + (X_z^p + u_2^p - Z^c)^2} - r - e$ $u_2^{p*} = R^c - X_r^p - r \tan^{-1}\left[\dfrac{R^c - X_r^p - u_1^p}{X_z^p + u_2^p - Z^c}\right]$ <u>Case B $X_r^p < R^c$</u>

Figure 30:
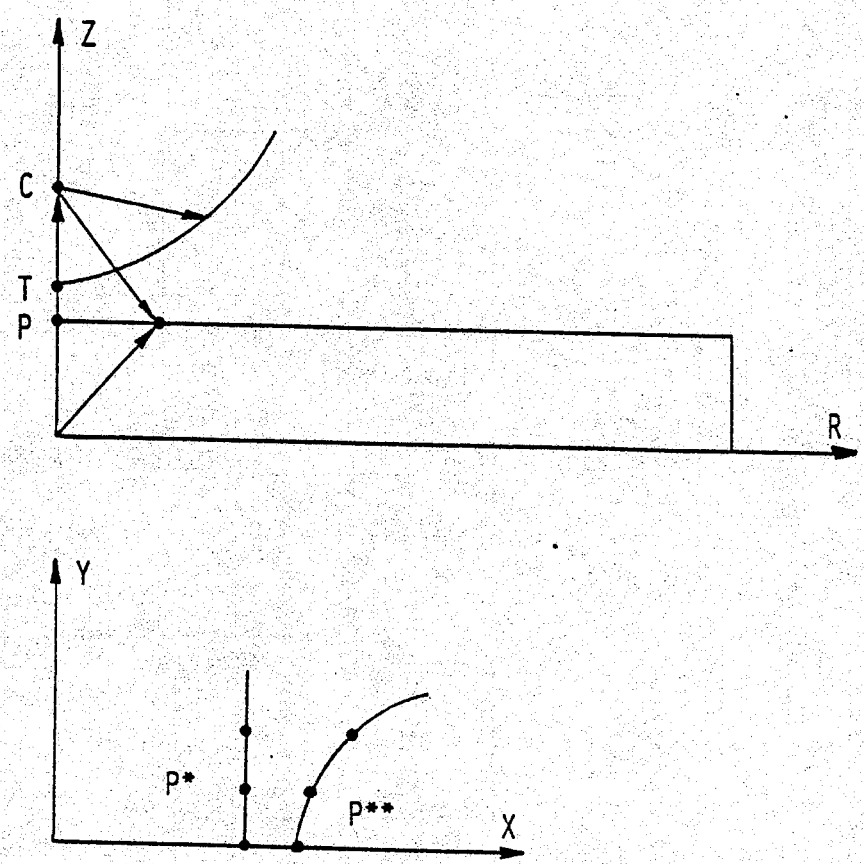
FIG. 30 is a friction-gap boundary condition model schematic for the miniaturized disk bend test punch. The velocity boundary condition is modelled by introducing dynamic centroid.

$x_r^p \equiv X_r^p + u_1^p \geq R^c$      Subcase I $u_1^{p*} = u_2^p + r - \sqrt{(R^c - X_r^p)^2 + (X_z^p - Z^c)^2}$ $u_2^{p*} = r \tan^{-1}\left[\dfrac{R^c - X_r^p}{r}\right] + X_r^p + u_1^p - R^c$ $x_r^p \equiv X_r^p + u_1^p < R^c$      Subcase II $u_1^{p*} = \sqrt{(R^c - X_r^p - u_1^p)^2 + (X_z^p + u_2^p - Z^c)^2} -$ $\sqrt{(R^c - X_r^p)^2 + (X_z^p - Z^c)^2}$ $u_2^{p*} = r\left\{\tan^{-1}\left[\dfrac{R^c - X_r^p}{r}\right] - \tan^{-1}\left[\dfrac{R^c - X_r^p - u_1^p}{X_z^p + u_2^p - Z^c}\right]\right\}$ The punch model is more complicated than the support model since the additional velocity boundary condition must be taken into account. This can be easily done by introducing a new node T which drives the plate as shown in FIG. 30. This driver node defines a dynamic centroid by the following relation:

$$X_z^c = X_z^T + RPUN$$

where

RPUN=punch tip radius

The same notation was used to derive the punch multi-point constraints. The sign convention and angle definitions used in the punch equation derivations are shown in FIG. 29. The following vector and angle relationships apply for the punch:

$$d^o = |\underline{X}^p - \underline{X}^c| - r$$

$$d = |\underline{x}^p - \underline{x}^c| - r$$

$$\tan\theta = \frac{x_r^p}{|x_z^c - x_z^p|}$$

$$\tan\theta' = \frac{X_r^p}{X_z^c - X_z^p}$$

The following multi-point constraint equations for the punch were derived:

$$u_1^{p*} = \sqrt{(X_r^p)^2 + (X_z^T + RPUN - X_z^p)^2} -$$

$$\sqrt{(X_r^p + u_1^p)^2 + (X_z^p + u_2^p - X_z^T - RPUN - u_2^T)^2}$$

$$u_2^{p*} = RPUN\left\{ \tan^{-1}\left[\frac{X_r^p + u_1^p}{X_z^T + u_2^T + RPUN - X_z^p - u_2^p}\right] - \tan^{-1}\left[\frac{X_r^p}{X_z^T + RPUN - X_z^p}\right] \right\}$$

A listing of the finite element friction gap boundary condition model subroutine follows:

```
      SUBROUTINE MPC(UE,A,JDOF,N,JTYPE,X,U)
      IMPLICIT REAL*8(A-H,O-Z)
      DIMENSION A(N),JDOF(N),X(6,N),U(6,N)
C
C
C JTYPE FLAGS THE PORTION OF THE STRUCTURE
C REQUIRING DOF CONDENSATION AS WELL AS THE
C DOF TO BE CONDENSED FOR A GIVEN NODE:
C
C    JTYPE=1 : SUPPORT B.C.; DOF 1
C    JTYPE=2 : SUPPORT B.C.; DOF 2
C    JTYPE=3 : PUNCH   B.C.; DOF 1
C    JTYPE=4 : PUNCH   B.C.; DOF 2
C
C
C HARD WIRE CENTROID PARAMETERS FOR SUPPORT
C
      EPS=.000001
      RC=.0485
      ZC=-.012
      R=.012
C
C HARDWIRE CENTROID PARAMETERS FOR PUNCH
C
      RPUN=0.02
C
C CHOOSE APPROPRIATE JTYPE ANALYSIS
C
      GO TO (100,200,300,400),JTYPE
C
C
C
C
C
C SUPPORT DOF CONDENSATION *****************************
C
C
C
```

```
C
C         CONDENSE DOF 1 FOR SUPPORT SHADOW NODE
C
    100 CONTINUE
        XRP=X(1,2)+U(1,2)
C
C         QUIZ INITIAL LOCATION OF PHYSICAL NODE
C
        XFAC=X(1,2)
        IF(XFAC.LT.RC)GO TO 101
C
C         INITIAL LOCATION .GE. RC
C
C         CASE A
C
C         QUIZ FINAL LOCATION OF PHYSICAL NODE
C
        IF(XRP.LT.RC)GO TO 102
C
C         FINAL LOCATION .GE. RC
C         CASE A 1
C
        UE=U(2,2)-EPS
        A(1)=1.0
        A(2)=0.0
        A(3)=-1.0
        JDOF(1)=1
        JDOF(2)=1
        JDOF(3)=2
        GO TO 999
    102 CONTINUE
C
C         FINAL LOCATION .LT. RC
C
C         CASE A 2
C
        XRP1=RC-XRP
        XRP2=X(2,2)+U(2,2)-ZC
        A1=XRP1*XRP1
        A2=XRP2*XRP2
        A3=A1+A2
        A4=DSQRT(A3)
        UE=A4-R-EPS
        A(1)=1.0
        A(2)=XRP1/A4
        A(3)=-XRP2/A4
        JDOF(1)=1
        JDOF(2)=1
        JDOF(3)=2
        GO TO 999
    101 CONTINUE
C
C         INITIAL LOCATION .LT. RC
C
C         QUIZ FINAL LOCATION OF PHYSICAL NODE
C
        IF(XRP.LT.RC)GO TO 103
```

```
C
C       FINAL LOCATION .GE. RC
C
C       CASE B 1
C
        A1=RC-X(1,2)
        A2=X(2,2)-ZC
        A3=A1*A1
        A4=A2*A2
        A5=A3+A4
        A6=DSQRT(A5)
        UE=U(2,2)+R-A6
        A(1)=1.0
        A(2)=0.0
        A(3)=-1.0
        JDOF(1)=1
        JDOF(2)=1
        JDOF(3)=2
        GO TO 999
    103 CONTINUE
C
C
C       FINAL LOCATION .LT. RC
C       CASE B 2
C
        XRP1=RC-XRP
        XRP2=X(2,2)+U(2,2)-ZC
        A1=XRP1*XRP1
        A2=XRP2*XRP2
        A3=A1+A2
        A4=DSQRT(A3)
        B1=RC-X(1,2)
        B2=X(2,2)-ZC
        B3=B1*B1
        B4=B2*B2
        B5=B3+B4
        B6=DSQRT(B5)
        UE=A4-B6
        A(1)=1.0
        A(2)=XRP1/A4
        A(3)=-XRP2/A4
        JDOF(1)=1
        JDOF(2)=1
        JDOF(3)=2
        GO TO 999
    200 CONTINUE
C
C
C
C
C
C
C       CONDENSE DOF 2 FOR SUPPORT SHADOW NODE
C
        XFAC=X(1,2)
        XRP=U(1,2)+X(1,2)
C
```

```
C       QUIZ INITIAL LOCATION OF PHYSICAL NODE
C
        IF(XFAC.LT.RC)GO TO 201
C
C       INITIAL LOCATION .GE. RC
C       CASE A
C
        IF(XRP.LT.RC)GO TO 202
C
C       FINAL LOCATION .GE. RC
C       CASE A 1
C
        UE=U(1,2)
        A(1)=1.0
        A(2)=-1.0
        A(3)=0.0
        JDOF(1)=2
        JDOF(2)=1
        JDOF(3)=2
        GO TO 999
    202 CONTINUE
C
C       FINAL LOCATION .LT. RC
C       CASE A 2
C
        XRP1=RC-XRP
        XRP2=X(2,2)+U(2,2)-ZC
        IF(XRP2.LE.0.0)GO TO 203
        ANG=XRP1/XRP2
        THETA=DATAN(ANG)
        GO TO 204
    203 CONTINUE
        THETA=1.57079633
    204 CONTINUE
        UE=RC-X(1,2)-(R*THETA)
        A(1)=1.0
        A1=XRP1*XRP1
        A2=XRP2*XRP2
        A3=A1+A2
        A(2)=-(R*XRP2)/A3
        A(3)=-(R*XRP1)/A3
        JDOF(1)=2
        JDOF(2)=1
        JDOF(3)=2
        GO TO 999
C
C       INITIAL LOCATION .LT. RC
C       CASE B
C
    201 CONTINUE
        IF(XRP.LT.RC)GO TO 207
C
C       FINAL LOCATION .GE.RC
C       CASE B 1
C
        ANG=(RC-X(1,2))/R
        THETA=DATAN(ANG)
```

```
      UE=(R*THETA)+X(1,2)+U(1,2)-RC
      A(1)=1.0
      A(2)=-1.0
      A(3)=0.0
      JDOF(1)=2
      JDOF(2)=1
      JDOF(3)=2
      GO TO 999
  207 CONTINUE
C
C     FINAL LOCATION .LT. RC
C     CASE B 2
C
      XRP1=RC-XRP
      XRP2=X(2,2)+U(2,2)-ZC
      IF(XRP2.LE.0.0)GO TO 209
      ANG=XRP1/XRP2
      THETA=DATAN(ANG)
      GO TO 210
  209 CONTINUE
      THETA=1.57079633
  210 CONTINUE
      ANG1=(RC-X(1,2))/R
      THETA1=DATAN(ANG1)
      UE=R*(THETA1-THETA)
      A(1)=1.0
      A1=XRP1*XRP1
      A2=XRP2*XRP2
      A3=A1+A2
      A(2)=-(R*XRP2)/A3
      A(3)=-(R*XRP1)/A3
      JDOF(1)=2
      JDOF(2)=1
      JDOF(3)=1
      GO TO 999
C
C
C
C
C
C PUNCH DOF CONDENSATION ******************************
C
C
C
C
C
C
  300 CONTINUE
C
C     CONDENSE DOF 1 FOR PUNCH SHADOW NODE
C
      A1=X(1,2)*X(1,2)
      ZCOMP=X(2,4)+RPUN-X(2,2)
      A2=ZCOMP*ZCOMP
      A3=A1+A2
      A4=DSQRT(A3)
      XRP=X(1,2)+U(1,2)
      B1=XRP*XRP
      XZPC=X(2,2)+U(2,2)-X(2,4)-RPUN-U(2,4)
```

```
      B2=XZPC*XZPC
      B3=B1+B2
      B4=DSQRT(B3)
      UE=A4-B4
      A(1)=1.0
      A(2)=XRP/B4
      A(3)=XZPC/B4
      A(4)=-A(3)
      JDOF(1)=1
      JDOF(2)=1
      JDOF(3)=2
      JDOF(4)=2
      GO TO 999
  400 CONTINUE
C
C     CONDENSE DOF 2 FOR PUNCH SHADOW NODE
C
      XRP=X(1,2)+U(1,2)
      XZCP=X(2,4)+U(2,4)+RPUN-X(2,2)-U(2,2)
      IF(XZCP.LE.0.0)GO TO 401
      ANG=XRP/XZCP
      THETA=DATAN(ANG)
      GO TO 402
  401 CONTINUE
      THETA=1.57079633
  402 CONTINUE
      XZCPO=X(2,4)+RPUN-X(2,2)
      ANG1=X(1,2)/XZCPO
      THETA1=DATAN(ANG1)
      UE=RPUN*(THETA-THETA1)
      A(1)=1.0
      A1=XZCP*XZCP
      A2=XRP*XRP
      A3=A1+A2
      A(2)=-(RPUN*XZCP)/A3
      A(3)=-(RPUN*XRP)/A3
      A(4)=-A(3)
      JDOF(1)=2
      JDOF(2)=1
      JDOF(3)=2
      JDOF(4)=2
      GO TO 999
  999 CONTINUE
      RETURN
      END
```

```
*HEADING
ELASTIC/PLASTIC;PUNCH & SUPPORT B.C.
100 ELEMENT MESH/HEDL-N LOT MATERIAL
482.3 DEGREE C MECHANICAL BEHAVIOR
*NODE
1,
39,.0475
801,,.01
839,.0475,.01
40,.0480
```

Herein is a listing of the Abaqus code input for the 100-element mesh used

```
240,.0480,.0025
440,.0480,.005
640,.0480,.0075
840,.0480,.01
41,.0485
841,.0485,.01
51,.059
851,.059,.01
100,,.010001
903,.01,1.25E-3
904,1.003878492E-2,1.25E-3
905,.01,2.50E-2
906,1.015663665E-2,2.50E-3
907,.01,3.75E-3
908,1.034950862E-2,3.75E-3
909,.01,5.00E-3
910,1.061649827E-2,5.00E-3
911,.01,6.25E-3
912,1.095477275E-2,6.25E-3
913,.01,7.50E-3
914,1.13609457E-2,7.50E-3
915,.01,8.75E-3
916,1.18312277E-2,8.75E-3
917,.01,1.00E-2
918,1.23615742E-2,1.00E-2
919,.01,1.125E-2
920,1.29478213E-2,1.125E-2
921,.01,1.25E-2
922,1.35858008E-2,1.25E-2
923,.01,1.375E-2
924,1.42714339E-2,1.375E-2
925,.01,1.50E-2
926,1.5008E-2,1.50E-2
927,.01,1.625E-2
928,1.57701863E-2,1.625E-2
929,.01,1.75E-2
930,1.65761171E-2,1.75E-2
931,.01,1.875E-2
932,1.74153698E-2,1.875E-2
933,.01,2.00E-2
934,1.82849784E-2,2.00E-2
951,0.0,.0485
952,-2.7054411E-3,.0485
953,0.0,.04853
954,-2.0200748E-3,.0485
955,0.0,.0485
956,-1.4164078E-3,.0485
957,0.0,.0485
958,-9.0590950E-4,.0485
959,0.0,.0485
960,-5.0000000E-4,.0485
961,0.0,.0485
962,-2.0911545E-4,.0485
963,0.0,.0485
964,-4.1594580E-5,.0485
965,0.0,.0485
966,-1.0412150E-5,.0485
``` to demonstrate the feasibility of the MBT methodology.

```
967,0.0,.0485
968,-1.0E-6,.0485
969,0.0,.0485
970,-1.0E-6,.0485
971,0.0,.0485
972,-1.0E-6,.0485
973,0.0,.0485
974,-1.0E-6,.0485
975,0.0,.0485
976,-1.0E-6,.0485
*NGEN
1,39,1
1,801,100
39,839,100
101,139,1
201,239,1
301,339,1
401,439,1
501,539,1
601,639,1
701,739,1
801,839,1
41,841,100
51,851,100
41,51,1
141,151,1
241,251,1
341,351,1
441,451,1
541,551,1
641,651,1
741,751,1
841,851,1
*ELEMENT,TYPE=CAX8R
1,601,603,803,801,602,703,802,701
77,639,641,841,839,640,741,840,739
81,641,643,843,841,642,743,842,741
*ELGEN,ELSET=ALL
1,4,-200,1
1,19,2,4
2,19,2,4
3,19,2,4
4,19,2,4
77,4,-200,1
81,4,-200,1
81,5,2,4
82,5,2,4
83,5,2,4
84,5,2,4
*NSET,NSET=FIXD
904,906,908,910,912,914,916,918,
920,922,924,926,928,930,932,934,
952,954,956,958,960,962,964,966,
968,970,972,974,976
*NSET,NSET=BCEN
1,101,201,301,401,501,601,701,801
*ELSET,ELSET=HAF
```

```
4,8,12,16,20,24,28,32,36,40,44,48
*MATERIAL,ELSET=ALL
*ELASTIC
2.02E7,.3009
*PLASTIC
8.267E4,0.0
9.47E4,.006
1.05E5,.053
1.0628E5,.091
*BOUNDARY
BCEN,1
FIXD,1,2
100,1
*FRICTION,PLANAR
903,904,.4,1.E7,3.8784920E-5
1.0,0.0,0.0,0.0,1.0,0.0
905,906,.4,1.E7,1.5663665E-4
1.0,0.0,0.0,0.0,1.0,0.0
907,908,.4,1.E7,3.4950862E-4
1.0,0.0,0.0,0.0,1.0,0.0
909,910,.4,1.E7,6.1649827E-4
1.0,0.0,0.0,0.0,1.0,0.0
911,912,.4,1.E7,9.5477275E-4
1.0,0.0,0.0,0.0,1.0,0.0
913,914,.4,1.E7,1.3609457E-3
1.0,0.0,0.0,0.0,1.0,0.0
915,916,.4,1.E7,1.8312277E-3
1.0,0.0,0.0,0.0,1.0,0.0
917,918,.4,1.E7,2.3615742E-3
1.0,0.0,0.0,0.0,1.0,0.0
919,920,.4,1.E7,2.9478213E-3
1.0,0.0,0.0,0.0,1.0,0.0
921,922,.4,1.E7,3.5858008E-3
1.0,0.0,0.0,0.0,1.0,0.0
923,924,.4,1.E7,4.2714339E-3
1.0,0.0,0.0,0.0,1.0,0.0
925,926,.4,1.E7,5.0008E-3
1.0,0.0,0.0,0.0,1.0,0.0
927,928,.4,1.E7,5.7701863E-3
1.0,0.0,0.0,0.0,1.0,0.0
929,930,.4,1.E7,6.5761171E-3
1.0,0.0,0.0,0.0,1.0,0.0
931,932,.4,1.E7,7.4153698E-3
1.0,0.0,0.0,0.0,1.0,0.0
933,934,.4,1.E7,8.2849784E-3
1.0,0.0,0.0,0.0,1.0,0.0
951,952,.4,1.E7,2.7054411E-3
-1.0,0.0,0.0,0.0,1.0,0.0
953,954,.4,1.E7,2.0200748E-3
-1.0,0.0,0.0,0.0,1.0,0.0
955,956,.4,1.E7,1.4164078E-3
-1.0,0.0,0.0,0.0,1.0,0.0
957,958,.4,1.E7,9.0590950E-4
-1.0,0.0,0.0,0.0,1.0,0.0
959,960,.4,1.E7,5.0000000E-4
-1.0,0.0,0.0,0.0,1.0,0.0
961,962,.4,1.E7,2.0911545E-4
```

```
-1.0,0.0,0.0,0.0,1.0,0.0
963,964,.4,1.E7,4.1594580E-5
-1.0,0.0,0.0,0.0,1.0,0.0
965,966,.4,1.E7,1.0412150E-5
-1.0,0.0,0.0,0.0,1.0,0.0
967,968,.4,1.E7,1.0E-6
-1.0,0.0,0.0,0.0,1.0,0.0
969,970,.4,1.E7,1.0E-6
-1.0,0.0,0.0,0.0,1.0,0.0
971,972,.4,1.E7,1.0E-6
-1.0,0.0,0.0,0.0,1.0,0.0
973,974,.4,1.E7,1.0E-6
-1.0,0.0,0.0,0.0,1.0,0.0
975,976,.4,1.E7,1.0E-6
-1.0,0.0,0.0,0.0,1.0,0.0
*GAP,TYPE=UNI
100,801,.000001,0.0,-1.0,0.0
*MPC,USER
3,903,802,802,100
4,903,802,802,100
3,905,803,803,100
4,905,803,803,100
3,907,804,804,100
4,907,804,804,100
3,909,805,805,100
4,909,805,805,100
3,911,806,806,100
4,911,806,806,100
3,913,807,807,100
4,913,807,807,100
3,915,808,808,100
4,915,808,808,100
3,917,809,809,100
4,917,809,809,100
3,919,810,810,100
4,919,810,810,100
3,921,811,811,100
4,921,811,811,100
3,923,812,812,100
4,923,812,812,100
3,925,813,813,100
4,925,813,813,100
3,927,814,814,100
4,927,814,814,100
3,929,815,815,100
4,929,815,815,100
3,931,816,816,100
4,931,816,816,100
3,933,817,817,100
4,933,817,817,100
1,951,33,33
2,951,33,33
1,953,34,34
2,953,34,34
1,955,35,35
2,955,35,35
1,957,36,36
```

```
2,957,36,36
1,959,37,37
2,959,37,37
1,961,38,38
2,961,38,38
1,963,39,39
2,963,39,39
1,965,40,40
2,965,40,40
1,967,41,41
2,967,41,41
1,969,42,42
2,969,42,42
1,971,43,43
2,971,43,43
1,973,44,44
2,973,44,44
1,975,45,45
2,975,45,45
*PLOT
UNDEFORMED MESH AT 100X WITH ELEMENT/NODAL NUMBERING
,,7.86666,7.86666,,5.,
*DRAW,ELNUM,NODENUM
*ELSET,ELSET=FST
1,2,3,4,5,6,7,8,9,10,11,12,13,14,15,
16,17,18,19,20,
21,22,23,24,25,26,27,28,29,30,31,32,
33,34,35,36,37,38,39,40,41,42,43,44,
45,46,47,48,49,50
*ELSET,ELSET=SEC
51,52,53,54,55,56,57,58,59,60,61,62,
63,64,65,66,67,68,69,70,71,72,73,74,
75,76,77,78,79,80,81,82,83,84,85,86,
87,88,89,90,91,92,93,94,95,96,97,98,
99,100
*PLOT
UNDEFORMED MESH NODAL/ELEMENT NUMBERING DETAIL
,,7.86666,7.86666,,5.,
*DETAIL,ELSET=FST
*DRAW,ELNUM,NODENUM
*DETAIL,ELSET=SEC
*DRAW,ELNUM,NODENUM
*RESTART,WRITE,FREQUENCY=500
*STEP,NLGEOM=ROT,INC=100
ELASTIC/PLASTIC ANALYSIS
*STATIC,PTOL=.5,NUMBER=1,CUTMAX=10
*BOUNDARY
100,2,,-.000001
*PRINT,ENERGY,FREQ=500
*EL PRINT,COORDS,ELSET=HAF
2,2,1,2,2
2,2,2,2
*LIST PRINT
2
*NODE PRINT
2,2,1,1,2,2,2
```

```
*PLOT,FREQUENCY=500
DEFORMED CONFIGURATION AT 100X
,,7.86666,7.86666,,3.5,
*DISPLACED
1,1.0
*PLOT ,FREQUENCY=500
STRESS CONTOUR IN UNDEFORMED CONFIGURATION
,,7.86666,7.86666,,3.5,
*CONTOUR
1,15,,,,,1
3,15,,,,,1
9,15,1.0E-10,1.1E5,,,1
*PLOT,FREQUENCY=500
STRAIN CONTOUR IN UNDEFORMED CONFIGURATION
,,7.86666,7.86666,,3.5,
*CONTOUR
31,15,,,,,1
33,15,,,,,1
37,15,1.0E-10,.5,,,1
*END STEP
*STEP,NLGEOM=ROT,INC=100
*STATIC,PTOL=.2,NUMBER=1,CUTMAX=10
*BOUNDARY
100,2,,-.000501
*END STEP
*STEP,NLGEOM=ROT,INC=100
*STATIC,PTOL=.35,NUMBER=1,CUTMAX=10
*BOUNDARY
100,2,,-.001001
*END STEP
*STEP,NLGEOM=ROT,INC=100
*STATIC,PTOL=.6,NUMBER=1,CUTMAX=10
*BOUNDARY
100,2,,-.001501
*END STEP
*STEP,NLGEOM=ROT,INC=100
*STATIC,PTOL=.675,NUMBER=1,CUTMAX=10
*BOUNDARY
100,2,,-.002001
*END STEP
*STEP,NLGEOM=ROT,INC=100
*STATIC,PTOL=.85,NUMBER=1,CUTMAX=10
*BOUNDARY
100,2,,-.003001
*END STEP
*STEP,NLGEOM=ROT,INC=100
*STATIC,PTOL=.9875,NUMBER=1,CUTMAX=10
*BOUNDARY
100,2,,-.004001
*END STEP
*STEP,NLGEOM=ROT,INC=100
*STATIC,PTOL=1.125,NUMBER=1,CUTMAX=10
*BOUNDARY
100,2,,-.005001
*END STEP
*STEP,NLGEOM=ROT,INC=100
*STATIC,PTOL=1.25,NUMBER=1,CUTMAX=10
```

```
*BOUNDARY
100,2,,-.006001
*END STEP
*STEP,NLGEOM=ROT,INC=100
*STATIC,PTOL=1.325,NUMBER=1,CUTMAX=10
*BOUNDARY
100,2,,-.007001
*END STEP
*STEP,NLGEOM=ROT,INC=100
*STATIC,PTOL=1.4,NUMBER=1,CUTMAX=10
*BOUNDARY
100,2,,-.008001
*END STEP
*STEP,NLGEOM=ROT,INC=100
*STATIC,PTOL=1.45,NUMBER=1,CUTMAX=10
*BOUNDARY
100,2,,-.009001
*END STEP
*STEP,NLGEOM=ROT,INC=100
*STATIC,PTOL=1.54,NUMBER=1,CUTMAX=10
*BOUNDARY
100,2,,-.010001
*END STEP
*STEP,NLGEOM=ROT,INC=100
*STATIC,PTOL=1.6,NUMBER=1,CUTMAX=10
*BOUNDARY
100,2,,-.011001
*END STEP
*STEP,NLGEOM=ROT,INC=100
*STATIC,PTOL=1.7,NUMBER=1,CUTMAX=10
*BOUNDARY
100,2,,-.012001
*END STEP
*STEP,NLGEOM=ROT,INC=100
*STATIC,PTOL=1.8,NUMBER=1,CUTMAX=10
*BOUNDARY
100,2,,-.013001
*END STEP
*STEP,NLGEOM=ROT,INC=100
*STATIC,PTOL=1.95,NUMBER=1,CUTMAX=10
*BOUNDARY
100,2,,-.014001
*END STEP
*STEP,NLGEOM=ROT,INC=100
*STATIC,PTOL=2.08,NUMBER=1,CUTMAX=10
*BOUNDARY
100,2,,-.015001
*END STEP
*STEP,NLGEOM=ROT,INC=100
*STATIC,PTOL=2.25,NUMBER=1,CUTMAX=10
*BOUNDARY
100,2,,-.016001
*END STEP
*STEP,NLGEOM=ROT,INC=100
*STATIC,PTOL=2.43,NUMBER=1,CUTMAX=10
*BOUNDARY
100,2,,-.017001
*END STEP
```

```
*STEP,NLGEOM=ROT,INC=100
*STATIC,PTOL=2.63,NUMBER=1,CUTMAX=10
*BOUNDARY
100,2,,-.018001
*END STEP
*STEP,NLGEOM=ROT,INC=100
*STATIC,PTOL=2.83,NUMBER=1,CUTMAX=10
*BOUNDARY
100,2,,-.019001
*END STEP
*STEP,NLGEOM=ROT,INC=100
*STATIC,PTOL=3.0,NUMBER=1,CUTMAX=10
*BOUNDARY
100,2,,-.020001
*END STEP
*STEP,NLGEOM=ROT,INC=100
*STATIC,PTOL=3.2,NUMBER=1,CUTMAX=10
*BOUNDARY
100,2,,-.021001
*END STEP
*STEP,NLGEOM=ROT,INC=100
*STATIC,PTOL=3.38,NUMBER=1,CUTMAX=10
*BOUNDARY
100,2,,-.022001
*END STEP
*STEP,NLGEOM=ROT,INC=100
*STATIC,PTOL=3.63,NUMBER=1,CUTMAX=10
*BOUNDARY
100,2,,-.023001
*END STEP
*STEP,NLGEOM=ROT,INC=100
*STATIC,PTOL=3.75,NUMBER=1,CUTMAX=10
*BOUNDARY
100,2,,-.024001
*END STEP
*STEP,NLGEOM=ROT,INC=100
*STATIC,PTOL=3.90,NUMBER=1,CUTMAX=10
*BOUNDARY
100,2,,-.025001
*END STEP
```

Various kinds of loadings can be applied as shown in FIGS. 3–7 to provide mechanical behavior information for miniature specimens. These specimens may be provided as a part of the initial processing of a material product or they may be provided by trepanning a specimen 25' from an inservice material 60 by means of a tool 61 (FIG. 8). The inservice material 60 may be a component of a nuclear reactor, a structural element such as a bridge girder, or a building column, wing strut in a space vehicle, etc.

The specimen 25' may be reshaped and provided as a specimen 25 in the apparatus of FIG. 1 or the apparatus of FIGS. 3–7. The selection of the particular apparatus and method that is used depends on the type of mechanical behavior determination to be made and the type of service that the inservice material 60 has been prior to the determination.

Referring to FIG. 3, the process is practiced in apparatus wherein the specimen is loosely supported between upper dies 65 and lower dies 66 and centered by side restraints 67. An upper punch 40' and a lower punch 68 alternately supply pressure to repeatedly bend the specimen 25 in opposite directions. Because the ends are unrestrained, fatigue life behavior can be determined for inservice situations where the end restraints have not been a factor in the service life that a material 60 has seen.

Referring to FIG. 4, the process is practiced in an apparatus wherein the specimen is tightly supported or clamped between upper dies 70 and lower dies 71 while centered by side restraints 72. An upper punch 40' and a lower punch 68' alternately supply a load to faces 26 and 27, respectively of the specimen 25. In the event that the inservice situation of the specimen was of the restrained end character use of the method in the apparatus of FIG. 4 is preferred.

Referring to FIG. 5, a specimen 25 is either loosely or tightly supported between upper dies 65' and lower dies 66' while centered by restraints 67'. An annular punch 75 provides loads at annular pressure positions 76 with the annulus substantially coaxial with the disk specimen 25. In some circumstances the application of the loads in this arrangement is more representative of the kind of inservice life that the specimen has been. As an alternative, another annular punch 78 may be positioned in contact with the opposite face of the disk 25 and a method of alternately applying loads from punches 75 and 78 is carried in a fatigue test.

In some circumstances, a better correlation with the inservice history of a specimen 25 may be determined in an apparatus as shown in FIG. 6, wherein a uniformly applied load, such as from fluid pressure, is applied to the upper face 26. The specimen 25 is held either loosely or tightly in an upper die 80 and a lower die 81 and sealed by elastic O-ring 82 or other appropriate seals, at least at the lower die 81. Alternatively, fluid pressure may be uniformly applied to the other face 27 of the specimen 25 with suitable clamping and seals 82 as described at both dies 80, 81. By this means alternately pulsating uniform loads can be applied to the specimen in a fatigue type test.

In still other circumstances, cantilevered loading on a specimen 25 may provide the best correlation for the practice of the invention with the inservice prior use of the specimen. Referring to FIG. 7, a specimen 25 is clamped at one side 87 between dies 85, 86. In one instance the load is applied on one face 26 by a punch 40' at a position 88 spaced from the clamped side 87 either once or repeatedly; or alternately between upper punch 40 and lower punch 68' to determine the mechanical behavior in fatigue.

A load relaxation experiment was performed on a 316 SS 20% CW sample at 600° C. The experiment was conducted in apparatus according to FIG. 1.

Two steel specimens were fatigued at room temperature under displacement control. The load range versus number of cycles is shown in FIG. 35 of four separate tests. The mean load level for the tests was 35.58 n and the loading for the bulk weight response was kept elastic. Care was taken to insure that the spcimen did not fully unload during the cycling. The rapid drop in load range indicates fatigue crack initiation and some degree of propagation to significantly reduce the load carrying capacity of the specimen. The average number of cycles to rapid load drop was found to be approximately $2.7 \times 10^4$ cycles for the tool steel at room temperature. In these studies it is concluded that fatigue studies for elastic cycling can be conducted without any modification of the MBT process.

Another problem addressed by this invention is the pressing need to determine the mechanical response of various materials which have been irradiated to very high doses (typically several hundred displacements per atom [dpa]), particularly in breeder reactor and fusion first wall materials research. In these reactors, a large portion of the damage to the material is due to fast neutrons and increases with fluence. Even with high flux rates, two to four year irradiations would be necessary to obtain design fluences of interest in breeder reactor cores and much longer for fusion reactor first wall studies.

Ion bombardment is very useful as a substitute because it can compress the time scale for irradiation by several orders of magnitude. Ion irradiation displacement rates on the order of $10^{-3}$ dpa per second can be achieved. Therefore, the damage produced in nuetron irradiation lasting several years can be achieved in several hours in an ion irradiation.

Although ion irradiation is faster, depth of penetration in a specimen is much less. Therefore, a specimen will have an irradiated portion near one face and an unirradiated portion remaining on the opposite side. However, with MBT, the specimen can be thinned down by shaving off the unirradiated side so taht the irradiated side becomes significantly thicker relative to the unirradiated side, and the results of the MBT will significantly approximate the mechanical behavior of the irradiated specimen.

It is a common practice in the determination of service life of material to follow a procedure of extracting an inverted pyramid portion from the surface of the inservice material and determining the behavior of the material as it passes from the inservice position to the extracted status. This determination of the changing status is accomplished by attaching strain gages to the surface of the inservice material before the pyramid is extracted. With the strain gage bridges in balance position the material is removed and the change in the bridge balance is measured. The relaxation of the material in transition from the inservice status to the removed status is an indication of the properties of the material.

In this practice, it can be determined whether or not the material has been carried beyond the yield point in service. By comparing the change in measurements from one status to the other with a predicted and expected stress/strain curve, it can be determined when a material has gone beyond the yield point. However, the further shape of the stress/strain curve cannot be predicted from this methodology.

However, by the finite element method and the practice of the MBT process of this invention the measured load deflection curve can be superimposed over the calculated load deflection curve and the residual plastic stresses can be approximately determined.

Any of the following determinations may be made using the process of this invention:

(a) uniaxial tensile behavior
(b) stress relaxation behavior
(c) creep response/ductility
(d) S-N fatigue response
(e) fatigue crack initiation/propagation
(f) ductile/brittle transition temperature
(g) fracture modes
(h) fracture stress and strain
(i) multi-layered specimens
(j) in-service testing
(i) residual plastic stress and strain
(l) multi-axial stress and strain
(m) isotropic/anisotropic material response
(n) in pile irradiation testing Stress Relaxation Behavior—A load relaxation experiment was performed on a 316 SS 20% CW sample at 600° C. The experiment was conducted in apparatus according to FIG. 1. The load as a function of time was recorded for a constant displacement magnitude. Finite element analyses are performed to provide the time dependent stress information. The data can be recorded in an apparatus such as those shown in FIGS. 1-7.

Creep Response/Ductility—The displacement as a function of time under constant applied load can be measured in an apparatus such as those shown in FIGS.

1-7. From this data, the steady state creep rate and creep ductility can be determined. Finite element analyses are performed to provide the time dependent strain information.

S-N Fatigue Response—Fatigue life is a mechanical behavior that is a statistical quantity. Each component put into service has a unique fatigue life which is a function of the material variability, fabrication techniques, environmental effects, and load history. With the MBT of this invention, mechanical behavior information for fatigue can be provided that is currently very difficult or impossible to obtain any other way.

Two steel specimens were fatigued at room temperature under displacement control in the apparatus shown in FIGS. 1 and 2. The load range versus number of cycles is shown in FIG. 35 for four separate tests. The mean load level for the tests was 35.58 n and the loading for the bulk weight response was kept elastic. Care was taken to insure that the specimen did not fully unload during the cycling. The rapid drop in load range indicates fatigue crack initiation and some degree of propagation to significantly reduce the load carrying capacity of the specimen. The average number of cycles to rapid load drop was found to be approximately $2.7 \times 10^4$ cycles for the tool steel at room temperature.

Fatigue testing can be done in any of the apparatus shown in FIGS. 1-7.

In general, miniaturized disk-, beam-, constant stress cantilever- and cruciform-shaped specimens as shown in FIGS. 1-7 and FIGS. 36-37, could be used to characterize fatigue behavior. Specimens of this size scale would enable a significant savings in testing time since the load and deflection ranges required in the test are greatly reduced. These specimens can be tested at a cycle rate of at least 20 Hz, which is approximately 7 times faster than the cycle rates currently in use with the large samples. Also, the test rig for these specimens can be adapted for multi-specimen testing, as shown in FIGS. 38, 39 and 40, to accommodate five or ten samples. These features can result in fatigue testing times which are up to 70 times shorter than the test times achieveable using large samples.

In addition, the effects of grain orientation on fatigue life can be easily investigated using the miniaturized beam- or cruciform-shaped specimens since samples can be cut to study, for example, the short transverse direction or any other grain orientation desired. Also, the fatigue strength of a forging through the thickness can be studied by cutting samples at several radial locations for a given grain orientation. Since antisotropy as well as grain boundary effects can have a significant impact on fatigue strength, miniaturized sample technology may prove to be an important tool for optimizing the fatigue characteristics of forged products.

With regard to the clamped constant stress beam shown in FIG. 36, in order to determine the specimen end deflection necessary to obtain a desired stress in the sample, it is possible to perform two uniaxial tensile tests in the long grain direction to determine the uniaxial tensile behavior of the material. This stress/strain curve can be used in conjunction with a strain gage mounted on the sample to determine the stress in the beam. Failure can be defined as complete through thickness fracture.

The cyclic softening behavior of the material can be accounted for during the test by periodically adjusting the displacement control to approximately keep the applied load constant.

The specimens in a multi-specimen test can be tested in displacement control. Failure in these specimens can be defined as a decrease of 5 percent in the measured strain. Load can also be monitored and used to define specimen failure in the unlikely event of a failure in the strain gage.

Fatigue Crack Initiation/Propagation-Fatigue crack initiation and propagation data can be determined using adherent crack gage technology and miniaturized specimens U.S. patent application, Ser. No. 48,550 now U.S. Pat. No. 4,255,974 has been filed on this development. While the gage has been successfully applied to larger uniaxial specimens, the current patent application is for use with miniaturized bend specimens. The concept will work for any of the specimens and loadings shown in FIGS. 1-7 and FIGS. 36-40. The following discussion will be limited to miniaturized disks that are pressure loaded.

The experimental configuration can consist of a simply supported or clamped pressure loaded disk. In order to determine the pressure necessary to obtain a required stress in the sample, it is necessary to perform a nonlinear finite element solution. In this way, the test pressure as a function of specimen stress and strain can be readily determined. The test is then controlled to the pressure range which will provide the prescribed maximum stress in the sample and stress ratio. Uniaxial tensile tests can be performed to determine the material stress/strain curve.

Some alloys exhibit cyclic hardening or softening due to plastic deformation. This effect can be accounted for in fatigue testing to ensure that the requird stresses in the test are maintained. The incremental step test can be performed to determine the cyclic deformation response of the material. If the stabilized cyclic material response is significantly different from the initial monotonic response, then the results can be incorporated into the computer control of the applied pressure. In general, the stabilized cyclic response is obtained early in the fatigue test. If this is the case, the computer control can be eliminated early in the experiment. This is advantageous since the computer often limits the test frequency.

The initiation and progression of the crack tip(s) can be monitored using an adherent crack gauge. The gauge works on the principle of the crack tip successively fracturing the individual bars in an array of bars located ahead of the crack tip. As the specific bars fracture, the resulting change in resistance is indicative of the location of the crack tip. Since the cracks will form and advance in any direction because of the symmetry in the experiment, a crack gauge consisting of an array of bars in the form of concentric circles can be employed. The radial spacing between circles for the first 1 cm (0.39) can be 0.25 mm (0.0098 in) so that changes in total crack length of 0.5 mm (0.020 in) can be detected. The spacing can be doubled between 1 cm (0.39 in) and 2 cm (0.79 in).

Because of the need for the close spacing of the detection bars and the circular array to allow for various crack directions, the gauges can be applied by vacuum sputtering and formed by photoetching techniques. An insulating layer of aluminum oxide can be sputtered on the tension side of the specimen, followed by an evaporated conducting layer of copper or manganin. The process can be controlled so that the total thickness is less than 2 microns (0.00008 in) to minimize the influence on the specimen. The gauge pattern can then be photoetched to the configuration of choice and electrical leads will be attached. This technique has been used to measure crack propagation.

The surface crack length measurement can be used to define failure. The surface crack length can be correlated with through specimen thickness crack height. In this way failure can be defined in several ways such as crack initiation, a specified crack height, or complete through thickness fracture. Several samples can be used for this calibration. Each sample can be cycled to a different crack size.

An additional advantage derived in using the adherent crack gauge is that crack propagation information can be reported. Plots of the fatigue crack growth rate as a function of the square root of the crack size can be readily reported using this technique. Finite element analyses can be performed to determine $\Delta K$.

Each of the calibration samples can be sectioned through the thickness and polished. Micrographs can be taken at each cut. This will enable the characterization of the crack height as a function of surface crack length. Failure could then be defined by a specified crack height. For example, the crack height which is just detectable for an in-service component using a nondestuctive evaluation test could be specified as the failure condition. The test could be terminated when the surface crack length corresponding to the crack height is attained.

Ductile/Brittle Transition Temperature (DBTT) Determination—Several commercial nuclear reactors are approaching the end of their design lives. Questions about the remaining ductility of the pressure vessel have recently arisen. In many cases, there are only a few impact samples left. Miniaturized DBTT samples could be fabricated and thus expand the available number of specimens by 1–3 orders of magnitude.

The primary difference between the mechanical behavior of austenitic and ferritic steels is, of course, that the ferritic steels become brittle at low temperatures. Austenitic steels remain ductile to temperatures as low as is readily attainable in uniaxial tensile testing. Brittleness, which is defined as the degree of ductility, it reltated to the strain at fracture for uniaxial tensile testing. For brittle materials, the fracture stress continually decreases and eventually coincides with the onset of yielding as the testing temperature is reduced. Therefore, one method to characterize the DBTT using the MBT is simply to plot the difference between central deflection to fracture and central deflection to departure from linearity versus temperature. For brittle materials, the onset of fracture is evidenced by a sharp load drop.

Toughness is defined by the area under the uniaxial tensile stress/strain curve up to the point of fracture, and is a measure of the energy per unit volume which is required to induce fracture. It is, in essence, a quantitative measure of the ability of a metal to deform plastically prior to fracture. In general, for pre-irradiation DBTT studies, impact testing is used because the generation of uniaxial tensile data, data inversion, and subsequent integration of the entire stress/strain curve is somewhat tedious. However, for post-irradiation studies, this method of generating toughness may be attractive for several reasons. The finite element information base for central load/deflection data inversions may already exist for standardized specimen geometries. The large cost and time investment of irradiating the samples may warrant the determination of additional tensile information. If the finite element data base did indeed exist beforehand, the process could be greatly streamlined by using mass measurement techniques for stress/strain curve integration. In essence, the toughness data could then be generated entirely in the laboratory in a very short time.

Figure 41:
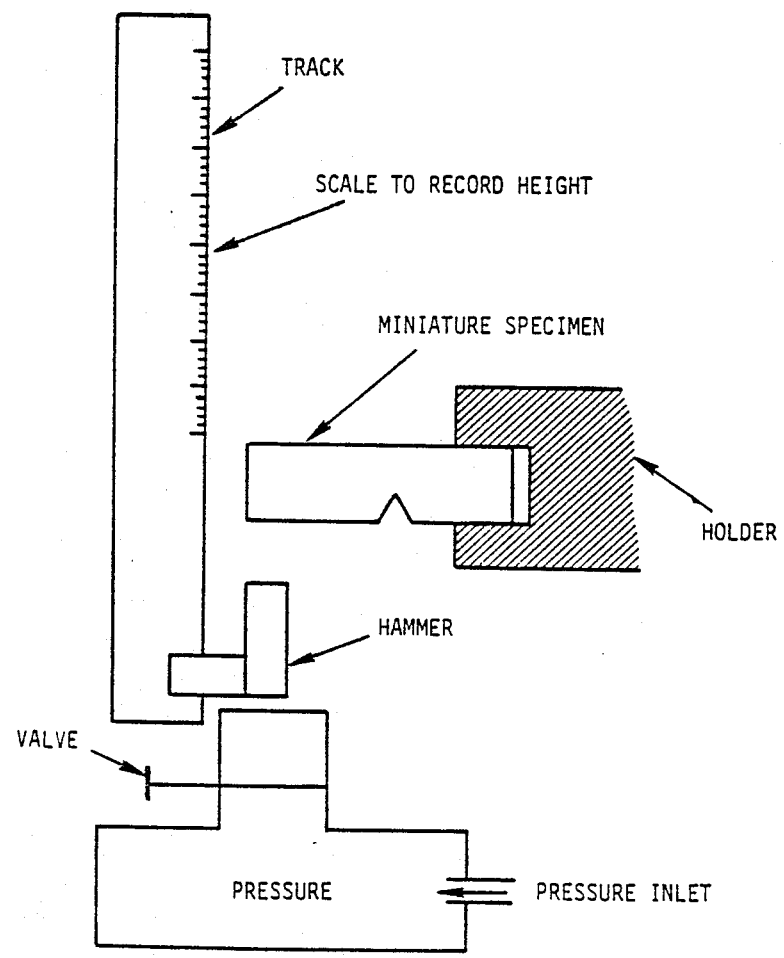
FIG. 41 is an elevational view of a fixture to test and determine ductile/brittle transition temperature information for use in another embodiment of the process of this invention.

Comparative test methods could also be pursued by building a special device to provide impact loads for pre-notched miniaturized samples. A device is shown in FIG. 41. These tests may provide an accurate measure of the true energy of fracture. However, such tests could quickly and reproducibly indicate the effects of such variables as temperature and irradiation on the alteration of brittle characteristics of ferritic steels. Scaled down versions of the Charpy V-notch or drop weight test can be implemented.

Fracture Modes—One of the objectives of the MBT is to be able to perform fracture mechanism studies for brittle as well as ductile materials. The capability to perform Scanning Electron Microscopy (SEM) using the MBT specimens has been demonstrated.

No difficulties in SEM examination, such as charging inside the crack cavity, were encountered for specimens that were properly mounted and grounded. Thus the capability of using the MBTT for crack mechanism studies has been demonstrated.

Fracture Stress and Strain determination—The results of the fracture initiation investigations for 302 SS shim stock and 316 SS are shown in FIGS. 34 and 35, respectively. In both cases, the fracture initiates prior to the load peak. As shown in FIG. 25, fracture has been observed to occur at a radial location of approximately 0.254 mm for the 302 SS shim stock specimens. This is due to the fact that the punch tip is of finite radius and causes an abrupt change in specimen curvature at this location. The fracture load range for the 316 SS material occurs somewhat closer to the load peak in comparison with the 302 SS shim stock data because of the larger ductility of the 316 SS material. Ultimately, the load drop is attributed to both a through thickness thinning of the specimen near the punch tip and the initiation and through thickness/circumferential propagation of the crack which both lead to a loss of load carrying capacity. Eventually, the load carrying capacity of the specimen is reduced to a point where the load drops for increased central deflection.

Multi-Layered Specimens—Mechanical behavior can be determined for specimens consisting of several layers of material each of which exhibit a different mechanical behavior is possible using the MBT methodology. Examples of conditions where this is useful would be ion irradiated samples as well as samples coated via physical/chemical vapor deposition. The case of ion irradiated samples will be discussed in detail.

Another problem addressed by this invention is the pressing need to determine the mechanical response of various materials which have been irradiated to very high doses (typically several hundred displacements per atom [dpa]), particularly in breeder reactor and fusion first wall materials research. In these reactors, a large portion of the damage to the material is due to fast neutrons and increases with fluence. Even with high flux rates, two to four year irradiations would be necessary to obtain design fluences of interest in breeder reactor cores and much longer for fusion reactor first wall studies.

Ion bombardment is very useful as a substitute because it can compress the time scale for irradiation by several orders of magnitude. Ion irradiation displacement rates on the order of $10^{-3}$ dpa per second can be achieved. Therefore, the damage produced in neutron irradiation lasting several years can be achieved in several hours in an ion irradiation.

Although ion irradiation is faster, depth of penetration in a specimen is much less. Therefore, a specimen will have an irradiated portion near one face and an unirradiated portion remaining on the opposite side. However, with MBT, the specimen can be thinned down by shaving off the unirradiated side to that the irradiated side becomes significantly thicker relative to the unirradiated side, and the results of the MBT will significantly approximate the mechanical behavior of the irradiated specimen. This is possible since in the finite element method it is possible to analyze a structure consisting of different materials, each exhibiting a different stress/strain law.

In Service Testing—Fatigue life is a statistical quantity. Each component put into service has a unique fatigue life which is a function of material variability, fabrication techniques, environmental effects, load history, etc. Therefore, a technique that would provide experimental fatigue data for inservice components to estimate residual/extended life is desirable. Components that are conservatively designed for fatigue may experience significantly different loading histories than anticipated during design. An inservice test methodology would be useful in estimating residual/extended component life in these situations. Therefore, a potential savings in human life as well as capital investment may be realized. Mechanical behavior information can be provided that is currently very difficult or impossible to obtain any other way. Also, additional data can be obtained from components to be studied that have been removed from service since many miniature samples can be cut from large components.

The MBT is designed to provide mechanical behavior information using a small volume of material. Therefore, the basic methodology can be used effectively as a semidestructive test technique for relatively thick components.

A specimen 25' can be trepanned out of in-service components as shown in FIG. 8 and machined to nominal dimensions. The miniature specimens can be used to determine mechanical behavior. Since fatigue behavior is of primary interest for inservice components, it will be discussed in some detail. Any of the loading configurations shown in FIGS. 1-7 or FIGS. 36-40 can be used.

Finite element analysis of the specimens would be done to determine the stress and strain distribution in the specimen for a given loading condition and material.

Fatigue life and fatigue limit are statistical quantities. A basic method for presenting fatigue data is by means of an S-N curve, which consists of a plot of stress measure versus the log of the number of cycles to failure. Several stress measures have been used such as:

$$\sigma_{mean} = (\sigma_{max} + \sigma_{min})/2$$

$$\sigma_{alternate} = \sigma_{max} - \sigma_{min}/2$$

$$R = \sigma_{max}/\sigma_{min}$$

$$A = \sigma_{alternate}/\sigma_{mean}$$

where $\sigma$ = stress.

Figure 42:
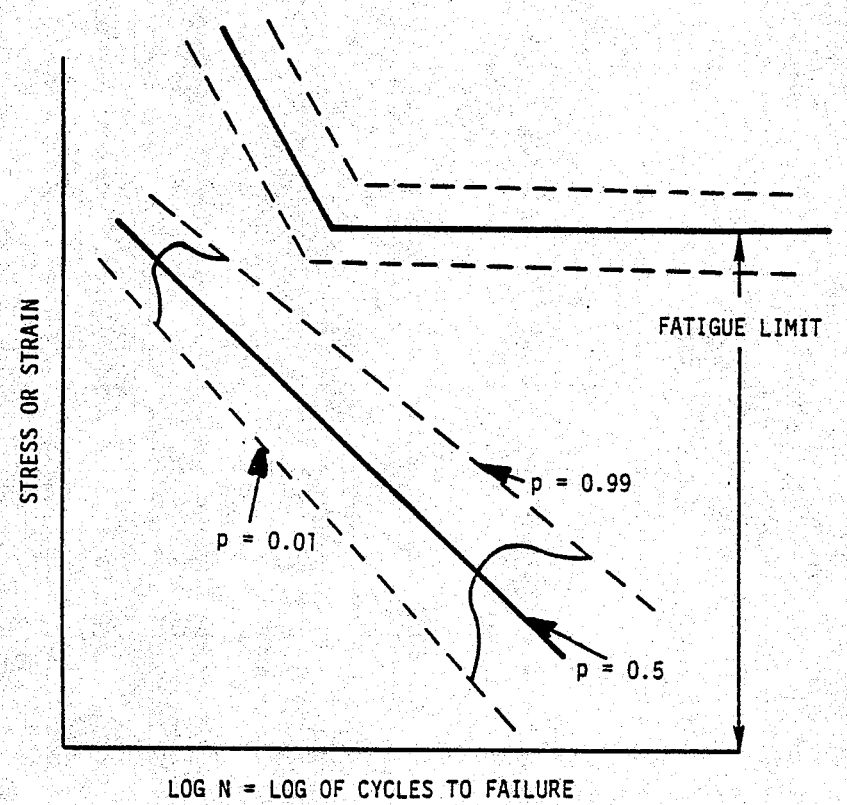
FIG. 42 is a graph showing typical results of a residual/extended fatigue life determination by the MBT process.

A sample S-N plot illustrating the statistical nature of fatigue is shown in FIG. 42.

Care must be exercised in interpretation of the results of small specimen data used to predict large component fatigue life. A proposed method is as follows:

(1) Obtain S-N data using large components with prototypical loading. Use enough samples to obtain reasonable good statistics (i.e., estimate of the mean and confidence internal) (~10-15 samples).

Figure 43:
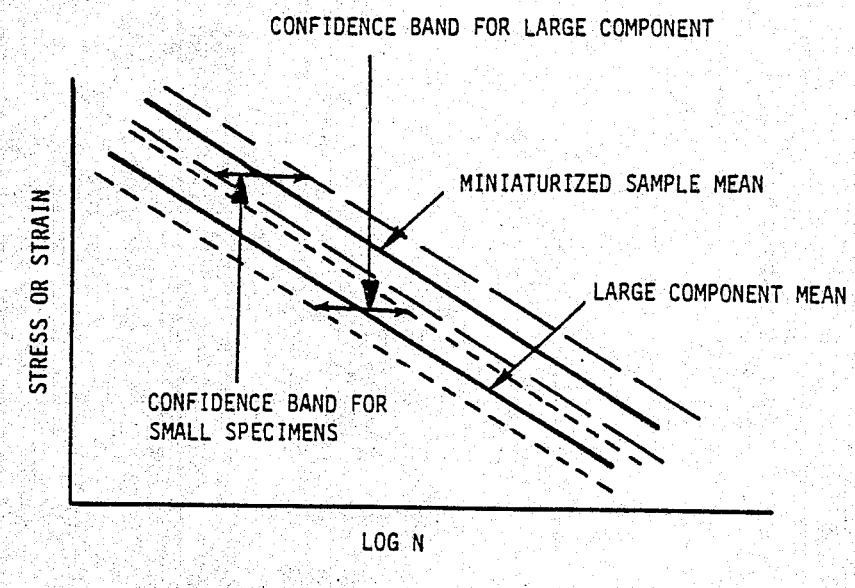
FIG. 43 is a graph showing other typical results of another residual/extended fatigue life determination by the MBT process.

(2) Using same heat of material, test miniaturized samples and obtain S-N data for chosen loading configuration for correlation with large component data. In many cases a size effect is observed and the fatigue strength of large members is lower than that of small specimens. (use typically 10-20 samples). A plot similar to FIG. 43 might be obtained.

(3) After a specified service life N, specimens would be trepanned from the in-service component at a specified interval n, machined, and tested to failure. Samples would be chosen from the most highly stressed region of the in-service component. Several samples would be taken at each n interval to provide good statistics (typically 5-10 samples).

Figure 44:
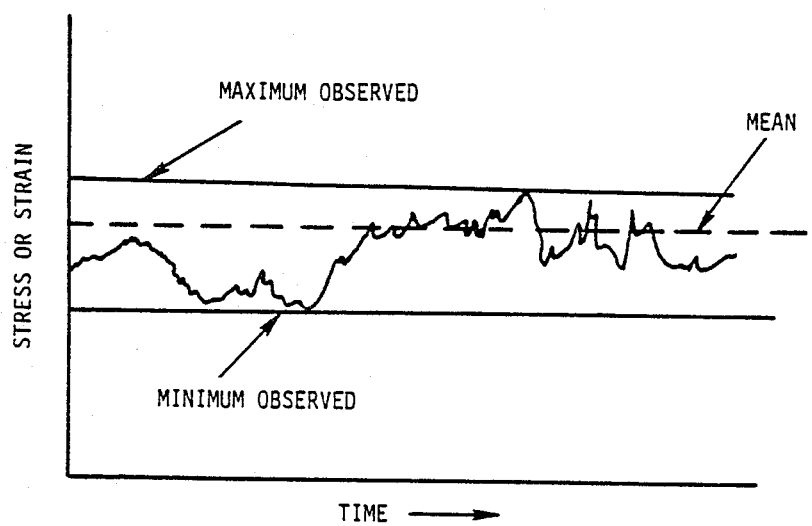
FIG. 44 is a graph of typical random loading of material.

A representative component could be instrumented with strain gages and put into service to determine the region and magnitude of highest stress. The load history would be recorded. The miniaturized samples could be tested at the highest stress or at a representative random distrubtion of stress in the measured range. The stress history may be as shown in FIG. 44.

Figure 45:
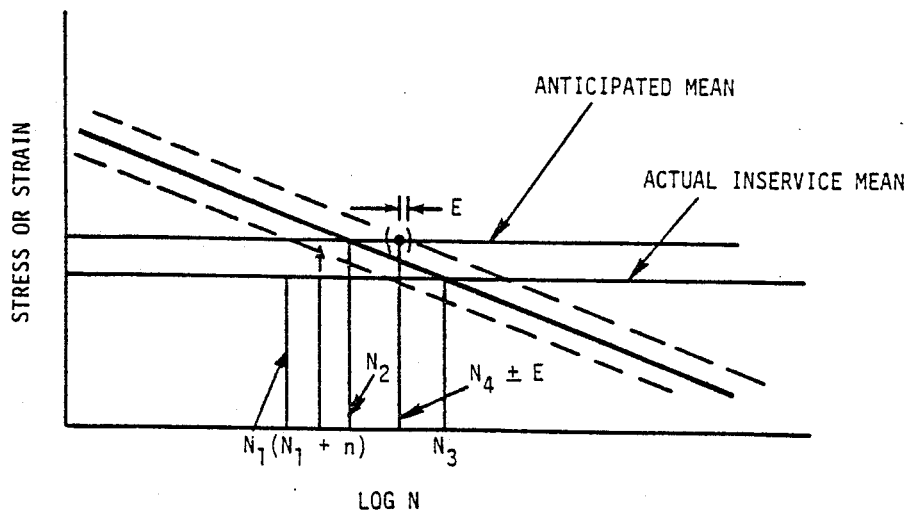
FIG. 45 is a typical graph of S-N fatigue results for the MBT process.

The results for a hypothetical case where the mean inservice loads were lower than anticipated is shown schematically in FIG. 45. The miniaturized samples in this case removed at ($N_1 + n$) cycles indicated longer residual life than anticipated. The remaining life for this measurement is now estimated to be $N_4$ (with a confidence interval E) which is larger than $N_2$. In this hypothetical case, on extended life may save premature replacement cost. On the other hand, the opposite result may have obtained yielding a shorter component life than expected. If this life turned out to be less than the design life, then in-service failure could be averted using the technique.

Care must be taken not to reduce component life by extracting samples from highly stressed component region. Shot peening, grinding, etc. could be considered. A favored approach would be to attach a "fatigue gage". This would consist of attaching (welding or fabricating) a flange of the same heat of material to the most highly stressed portion of the in-service component.

A vacuum deposited adherent crack gauge is the subject of a U.S. patent application Ser. No. 48,550, and is assigned to the same assignee as this application. In the gage, physical vapor deposition of small conducting rings on lines on the miniature fatigue sample surface enables the determination of fatigue crack initiation and propagation information. These data are also useful in defining failure for S-N determination. For example, several samples could be fatigued to progressively higher numbers of cycles. Each sample could then be sectioned and studied to determine the crack depth profile. In this way, a correlation between the surface crack length and depth could be determined for a given material. In this way, failure in an S-N test could be defined as crack initiation, or crack propagation to a specified crack depth.

Also these data can be used in conjunction with probalistic fracture mechanics (PFM) codes to optimize in-service component testing intervals, repair time, and component removal from service. Samples could be cut from inservice components periodically and tested to see if the crack propagation law for the material has changed significantly. If so, then the law would be updated in the PFM analysis.

The miniaturized specimen experimental data can be used as input to the PFM models to calculate the time dependent probability of in-service component failure. However, such a calculation performed at the beginning of the component's service life can result in errors which increase with time due to inaccurate load information, changing material properties, etc. After a time interval $\Delta t_i$, the structure can be inspected and tested to update this information. FIG. 46 illustrates possible results obtained using the methodology. After the time interval $\Delta t_i$, miniature samples are removed and tested. Based on these experimental results the PFM model parameters are adjusted and a new failure probability prediction as a function of time made. Early in the service life of the structure relatively few inspections are required since the defect growth rate is small. As the defects grow in size, a subsequent increase in the failure probability will occur requiring more frequent inspections to insure structural integrity. Eventually, as shown it time $T_4$ in FIG. 46, the probability of failure has reached a level that requires these inspections to be made so frequently that it is more cost effective to repair or replace the component. Therefore, if the component is repaired at this time, the probability of failure will actually decrease since the larger defects will have been removed.

Residual Plastic Stress and Strain Determination—It is a common practice in the determination residual elastic stress/strain to follow a procedure of extracting an inverted pyramid portion from the surface of the component material. This determination of the residual elastic stress/strain is accomplished by attaching strain gages to the surface of the component material before the pyramid is extracted. With the strain gage bridges in balance, the material is removed and the change in the bridge balance is measured. The relaxation of the material in transition from the inservice status to the removed status is an indication of the residual elastic stress/strain in the material.

In this practice, it can be determined whether or not the material has been carried beyond the yield point in service. By comparing the change in measurements from one status to the other with a predicted and expected stress/strain curve, it can be determined when a material has gone beyond the yield point. However, the further shape (plastic portion) of the stress/strain curve cannot be predicted from this methodology.

If the residual elastic stresses determined using the chip removal method indicate that the component was stressed beyond the yield, the residual plastic stresses can be determined using the MBT process. The pyramid of material removed to determine the residual elastic stresses can be machined into a miniaturized disk or other appropriate shape. The disk will then be tested in the usual way to determine the tensile behavior of the material. Since the tensile stress/strain curve for the material is known, the load/deflection response can be calculated using the finite element method. The measured load deflection curve can be superimposed over the calculated load deflection curve and the residual plastic stresses can be approximately determined. The process is illustrated in FIGS. 47-51.

Multi-Axial Stress and Strain—In the MBT, multi axial stress and strain components can be reported since the finite element code calculates them. Also the stress field in the miniature disk and the miniature cruciform specimen are substantially biaxial.

Isotropic/Anisotropic Material Response—Materials which behave substantially as isotropic and materials which behave substantially as anisotropic can be tested using the MBT methodology since the finite element code allows material behavior curves which are isotropic, orthotropic, and fully anistropic.

In-Pile Irradiation Testing—Since the MBT uses small specimens and small test rigs, the experiments can be carried out in a nuclear reactor or other irradiation device. An experiment utilizing the MBT methodology to study synergistic effects of helium bombardment and stress cycling can be performed. A simple test rig and a small accelerator capable of delivering 150 keV alpha particles with a flux of $10^{12}-10^{13}/(cm^2 sec)$ could be used to cycle the stress while simultaneously irradiating the sample at various temperatures and environmental conditions. In this fashion, S-N fatigue data for ion irradiated samples could be compared to unirradiated sample data for a variety of materials.

It is herein understood that although the present invention has been specifically disclosed with the preferred embodiment and examples, modification and variation of the concepts herein disclosed may be resorted to by those skilled in the art. Such modifications and variations are considered to be within the scope of the invention and the appended claims.

The following references are incorporated herein:
(1) Manahan, Michael Peter, "The Development of a Miniatureized Disk Bend Test for the Determination of Post-Irradiation Mechanical Behavior", submitted to the Department of Nuclear Engineering in Partial Fulfillment of the Requirements for the Degree of Doctor of Science at Massachusetts Institute of Technology, May, 1982.
(2) Herbert, Von H., "Ueber den Zusammenhang der Biegungselastizitat des Guesseisens mit seiner Zug- and Druckelastizitat", Mitt. u Forschungsarb, *Ver. deut. Ing.*, 89, 1910.
(3) Crocker, W. H., "Obtaining a Stress/Strain Relationship from a Rotary Three-Point Bend Test with Large Plastic Displacement", submitted in partial fulfillment of the requirements for the M.S. Degree at M.I.T., August, 1979.
(4) Stelson, K. A., and Gossard, D. C., "An Adaptive Pressbrake Control Using an Elastic-Plastic Material Model", Proceedings of the 1982 Joint Automatic Control Conference, 11, June 17-19, 1981, Charlottesville, Va.
(5) Fan Hsiung Huang, Margaret L. Hamilton, and Gary L. Wire, "Bend Testing for Miniature Disks", Hanford Engineering Development Laboratory, P.O. Box 1970, Richland, Wash. 99352, Nov. 9, 1981.
(6) ABAQUS, developed by Hibbitt and Karlsson, Inc., Providence, R.I.
(7) Bathe, K. J., "Automatic Dynamic Nonlinear Incremental Analysis (ADINA)", MIT Report No. 82448-1, December, 1978.
(8) Nagamatsu, A., Murota, T., and Jimma, T., Bull. J. SME, 15, 1339 (1972).
(9) Nagamatsu, A., Murota, T., and Jimma, T., Bull. J. SME, 14, 322 (1971).
(10) Gordon, J. L., and Weinstein, A. S., Proc. 2nd NAMRC Conf. Wisconsin (1974).
(11) Iwata, K., Osakada, K., and Fujino, S., J. Engng Ind. 94, 697 (1972).
(12) Odell, E. J., J. Engng Ind. 100, 31 (1978).

(13) Shah, S. N., and Kobayashi, S., Proc. 15th Int. M.T.D.R. Conf., Birmingham (1974).

(14) Matsumoto, H., Oh, S. I., and Kobayashi, S., Proc. 18th Int M.T.D.R. Conf., Imperial College, London (1977).

(15) Sharman, F. W., Electricity Council Report R581 (1975).

(16) Zienkiewicz, O. C., Jian, P. C., and Onate, E., Int J. Solids Structures 14, 15 (1978).

(17) Hartley, P., Sturgess, C. E. N., and Rowe, G. W., Int J. Mech. Sci, vol 21 pp. 301-311 (1978).

(18) Rodal, J. J. A., "Finite-Element Large-Deflection Finite-Strain Elastic-Plastic Transient Response Analysis of Structures", MIT Ph.D. Thesis, June, 1979.

(19) Private communication, E. Rabinowicz to M. P. Manahan, March, 1981.

(20) Rabinowicz, E., "Friction and Wear of Materials", John Wiley and Sons (1965).

(21) Fish, R. L., Cannon, N. S., and Wire, G. L., "Tensile Property Correlations for Highly Irradiated 20 Percent Cold-Worked Type 316 Stainless Steel", ASTM STP 683, (1979).

(22) Paxton, M. M., "Mechanical Properties of Prototype FTR Cladding—20% CW 316 Stainless Steel Tubing", HEDL-TME 71-59 (April 1971).

(23) Manahan, M. P., and Argon, A. S., "Design of Mechanical Property Tests and Establishment of Associated Testing Systems", in "Annual Report on Alloy Development for Irradiation Performance in Fusion Reactors", September 1979–September 1980, Report No. MITNRL-006 and DOE/ER-10107-1, December 1980.

(24) M. P. Manahan, A. S. Argon and O. K. Harling, "The Development of a Miniaturized Disk Bend Test for the Determination of Postirradiation Mechanical Properties," presented at the *Second Topical Meeting on Fusion Reactor Materials*, Aug. 9-12, 1981, Seattle, Wash., published in a *J. of Nucl. Mater.* 103 and 104 (1981) 1545-1550.

(25) M. P. Manahan, "A New Post-Irradiation Mechanical Behavior Test—The Miniaturized Disk Bend Test", presented at the ANS Winter Meeting, Nov. 17, 1982; published in the Journal of Nuclear Technology, Volume 63, November 1982.

We claim:

1. A process of determining mechanical behavior of solid material, comprising:
   a. providing a specimen of the material having at least a volume and smallest dimension sufficient to satisfy continuum behavior in all directions, and with the volume not more than $10^7$ times said sufficient volume;
   b. deforming the specimen by applying a load on the specimen;
   c. measuring at least one key variable in step b; and
   d. determining the tensile behavior of the material from the measurements taken according to the principles of the finite element method, and/or determining other mechanical behavior of the material from the measurements taken according to the principles of linear or nonlinear material mechanics or both.

2. A process according to claim 1 wherein either the applied load or the displacement of the specimen (or both) is (are) measured as a function of time.

3. A process according to claim 1 wherein the specimen is a disk and the load is applied on a face of the disk.

4. A process according to claim 3 wherein the specimen is supported on a face of the disk.

5. A process according to claim 4 wherein the disk is supported on a face near the edge and the load is applied by a rounded punch on the opposite face substantially at the center of the disk.

6. A process according to claim 5 wherein the load is applied either once or repeatedly.

7. A process according to claim 5 wherein the material is a post-irradiated stainless steel and the process is carried out in an inert atmosphere at a temperature of about $0°$ K. to the melting temperature of the material.

8. A process according to claim 4 wherein the load is applied alternately and oppositely between a rounded punch on each face of the disk, substantially at the center of the disk.

9. A process according to claim 8 wherein the disk is in unconfined support.

10. A process according to claim 8 wherein the disk is supported and clamped on the faces near the edges.

11. A process according to claim 4 wherein the disk is in unconfined support on one face near the edge and the load is applied by a rounded annular punch with the annulus substantially coaxial with the disk.

12. A process according to claim 4 wherein the load is applied alternately and oppositely between rounded annular punches substantially coaxial with the disk on each face.

13. A process according to claim 12 wherein the disk is in unconfined support.

14. A process according to claim 12 wherein the disk is supported and clamped at the faces near the edges.

15. A process according to claim 4 wherein the disk is clamped and sealed on opposite faces near the edge and the load is applied by fluid pressure uniformly distributed across a face of the disk on one side.

16. A process according to claim 4 wherein the disk is sealed near the edge on one face, and the load is applied by fluid pressure uniformly distributed across the exposed face of the disk on the face opposite to the sealed face.

17. A process according to claim 4 wherein the disk is clamped and sealed on opposite faces near the edge and the load is applied by fluid pressure uniformly distributed alternately on opposite faces of the disk.

18. A process according to claim 4 wherein the disk is sealed on opposite faces near the edge and the load is applied by fluid pressure uniformly distributed alternately on opposite sides of the disk.

19. A process according to claim 1 wherein the specimen is a beam and the load is applied on a face of the beam.

20. A process according to claim 19 wherein the specimen is supported on a face of the beam.

21. A process according to claim 20 wherein the specimen is clamped at one side and the load is applied on one or both faces at a position spaced and the clamped side either once or repeatedly, so that the specimen reacts as a cantilever beam.

22. A process according to claim 21 wherein the load is applied by a rounded punch or a substantially cylindrical surface.

23. A process according to claim 20 wherein the specimen is clamped at one side and the load is applied alternately on each face a position spaced from the clamped side repeatedly, so that the specimen reacts as a cantilever beam.

24. A process according to claim 23 wherein the load is applied by a rounded punch or a substantially cylindrical surface.

25. A process according to claim 20 wherein the beam is supported on a face near opposite edges and the load is applied on the opposite face, substantially at the center, by either a rounded punch or a substantially cylindrical surface.

26. A process according to claim 25 wherein the load is applied either once or repeatedly.

27. A process according to claim 20 wherein the load is applied alternately and oppositely between a rounded punch or a substantially cylindrical surface on each face of the beam, substantially at the center of the beam.

28. A process according to claim 27 wherein the beam is in unconfined support.

29. A process according to claim 27 wherein the beam is supported and clamped on the faces near opposite edges.

30. A process according to claim 20 wherein the beam is placed in unconfined support on one face near opposite edges and the load is applied by two substantially cylindrical surfaces, at equal distances from the center of the beam.

31. A process according to claim 20 wherein the load is applied alternately and oppositely between substantially cylindrical surfaces, two on each face, at equal distances from the center of the beam.

32. A process according to claim 31 wherein the beam is in unconfined support.

33. A process according to claim 31 wherein the beam is supported and clamped at the faces near the edges.

34. A process according to claim 1 wherein the specimens are of a cruciform shape.

35. A process according to claim 1 wherein the determining step d for other mechanical behavior is carried out according to the processes of continuum material mechanics and according to the finite element method.

36. A process according to claim 35 wherein boundary condition modelling for the finite element method is carried out using shadow node mapping theory.

37. A process according to claim 1 wherein the specimen comprises an irradiated material.

38. A process according to claim 1 wherein the specimen comprises a plurality of layers of material having different mechanical behavior response in each layer.

39. A process according to claim 38 wherein the specimen comprises an ion-irradiated specimen with a radiation damaged layer of unknown mechanical behavior and a layer of unirradiated material of known mechanical behavior.

40. A process according to claim 1 wherein a plurality of specimens are tested together and simultaneously.

41. A process according to claim 1 wherein the specimen comprises a material that behaves substantially as isotropic, a material that behaves substantially as anisotropic, or a material that behaves substantially as orthotropic.

42. A process according to claim 1 wherein steps b and c are carried out in a nuclear reactor or other appropriate irradiation facility.

43. A process according to claim 1 wherein the process is carried out in a controlled environment at a temperature of about 0° K. to the melting temperature of the material.

44. A process according to claim 1 wherein the specimen is trepanned from an inservice material.

45. A process according to claim 1 wherein the smallest dimension is substantially the continuum mechanics limit of the material.

46. A process according to claim 1 wherein the specimen providing step a comprises:
 a'. providing a strain gage on the surface of a strained inservice material;
 b'. trepanning a pyramidal portion of the inservice material including the strain gage and measuring the relieved strain in the material;
 c'. determining whether the material has been loaded above the yield point stress while in service; and
 d'. furnishing a specimen from the pyramidal portion for the bending, measuring, and behavior determining steps b, c, and d.

47. A process according to claim 46 wherein the mechanical behavior to be determined is the residual plastic stress and strain.

48. A process as in claim 1 wherein the mechanical behavior determining step d comprises:
 e. computing the load/deflection function corresponding to at least one trial stress/strain function, and
 f. comparing the computed load/deflection function with the load/deflection function measured in step c.

49. A process as in claim 48 comprising also:
 g. repeating steps e and f for new trial stress/strain functions until a trail stress/strain function provides a computed load/deflection function that differs from the measured load/deflection function in the opposite direction from that of another computed load/deflection function,
 h. repeating steps e and f for a trial stress/strain function interpolated between the trial stress/strain function for which the computed load/deflection functions differ the least from the measured load/deflection function and in opposite directions therefrom, and
 i. repeating step h until a stress/strain function is determined for which the computed load/deflection function is within a selected range of tolerance from the measured load/deflection function.

50. A process as in claim 49 wherein the computing step e is carried out using an appropriate finite element computer code capable of modelling the non-linear material (constitutive), geometrical, and boundary conditions present during steps b and c.

51. A process as in claim 49 wherein the computing step e is carried out using the ABAQUS finite element computer code and the finite element friction-gap boundary condition model subroutine.

52. A process as in claim 48 comprising also:
 g. repeating steps e and f for new trial stress/strain functions until a trial stress/strain function provides a computed load/deflection function that differs from the measured load/deflection function in the opposite direction from that of another computed load/deflection function, and
 j. determining the stress/strain function for the measured load/deflection function by interpolation between the trial stress/strain functions for which the computed load/deflection functions differ the least from the measured load/deflection function and in opposite directions therefrom.

53. A process as in claim 52 wherein the interpolation is carried out point by point.

54. A process as in claim 52 wherein the interpolation is carried out with an empirically determined algorithm.

55. A process as in claim 52 wherein the computing step e is carried out using an appropriate finite element computer code capable of modelling the non-linear material (constitutive), geometrical, and boundary conditions present during steps b and c.

56. A process as in claim 52 wherein the computing step e is carried out using the ABAQUS finite element computer code and the finite element friction-gap boundary condition model subroutine.

57. A process as in claim 48 wherein the trial stress/-strain functions are expressible as mathematical relations.

58. A process as in claim 48 wherein the trial stress/-strain functions are expressible as power law relations.

59. A process as in claim 58 wherein each power law relation has the general form $$\sigma = K\epsilon^n$$

where
$\sigma$ = true stress
$\epsilon$ = true strain
n = strain-hardening exponent
$K = \sigma_{uts}/n^n$ = strength coefficient,
$\sigma_{uts}$ = true ultimate tensile strength.

60. A process as in claim 48 wherein the trial stress/-strain functions are expressed as a power series.

61. A process as in claim 60 wherein the power series has the general form $$\sigma = a_0 + a_1\epsilon + a_2\epsilon^2 + \cdots + a_n\epsilon^n,$$

where each $a_i$ is a constant.

62. A process as in claim 48 wherein the trial stress/-strain function in step e is related to known behavior of the material or of a material having similar relevant characteristics.

63. A process as in claim 62 wherein the material is an alloy, and the known behavior is that of another alloy having the same base; or wherein the material has been irradiated, and the known behavior is that of similar material that has not been irradiated; or wherein the material has been irradiated, and the known behavior is that of similar material that has been irradiated.

Figure 31:
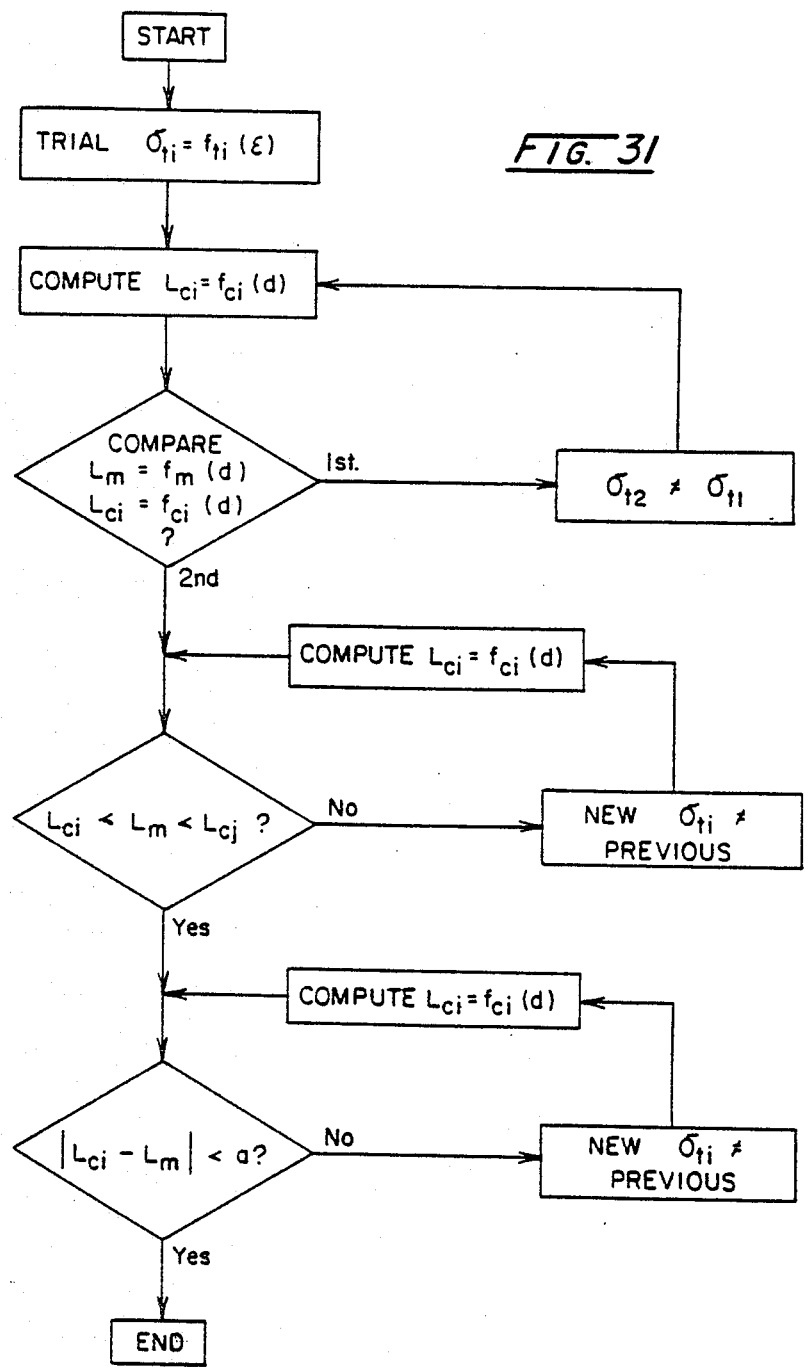
FIG. 31 is a flow diagram for determining the stress/strain function for a measured load/deflection function.

64. A process as in claim 48 wherein the mechanical behavior determining step d is carried out substantially in accordance with FIG. 31 of the drawings hereof, and the description relating thereto in the foregoing specification.

* * * * *